(12) United States Patent
Schraga

(10) Patent No.: US 8,303,545 B2
(45) Date of Patent: Nov. 6, 2012

(54) INFUSION DEVICE AND METHOD OF USING AND MAKING THE SAME

(75) Inventor: Steven Schraga, Surfside, FL (US)

(73) Assignee: Stat Medical Devices, Inc., North Miami, FL (US)

( * ) Notice: Subject to any disclaimer, the term of this patent is extended or adjusted under 35 U.S.C. 154(b) by 751 days.

(21) Appl. No.: 11/851,742

(22) Filed: Sep. 7, 2007

(65) Prior Publication Data

US 2009/0069750 A1     Mar. 12, 2009

(51) Int. Cl.
*A61M 31/00* (2006.01)
(52) U.S. Cl. .............. 604/167.02; 604/86; 604/117; 604/264; 604/272; 604/539
(58) Field of Classification Search .......... 604/19, 604/21, 46–48, 86, 93.01, 115, 117, 130, 604/137, 148, 158, 181, 187, 200, 206, 220, 604/264, 272, 288.02, 167.02; 606/167, 606/184–185
See application file for complete search history.

(56) References Cited

U.S. PATENT DOCUMENTS

| | | | |
|---|---|---|---|
| 4,747,831 A | 5/1988 | Kulli | |
| 4,755,173 A | 7/1988 | Konopka et al. | |
| 5,954,643 A | 9/1999 | VanAntwerp et al. | |
| 6,093,172 A * | 7/2000 | Funderburk et al. | 604/135 |
| 6,096,011 A | 8/2000 | Trombley, III et al. | |
| 6,302,866 B1 | 10/2001 | Marggi | |
| 6,332,875 B2 | 12/2001 | Inkpen et al. | |
| 6,368,141 B1 | 4/2002 | VanAntwerp et al. | |
| 6,884,230 B1 | 4/2005 | Epstein et al. | |
| 6,949,084 B2 | 9/2005 | Marggi et al. | |
| 6,960,192 B1 | 11/2005 | Flaherty et al. | |
| 6,997,907 B2 | 2/2006 | Safabash et al. | |
| 7,052,483 B2 | 5/2006 | Wojcil | |
| 7,083,626 B2 | 8/2006 | Hart et al. | |
| 2002/0072720 A1 | 6/2002 | Hague et al. | |
| 2004/0158207 A1 * | 8/2004 | Hunn et al. | 604/164.01 |
| 2005/0101932 A1 * | 5/2005 | Cote et al. | 604/506 |
| 2005/0101933 A1 * | 5/2005 | Marrs et al. | 604/506 |
| 2007/0135774 A1 * | 6/2007 | Turner et al. | 604/288 |

OTHER PUBLICATIONS

Simple Choice Press Release entitled CSII Insulin Delivery with an Intradermal Patch Infusion Set Compared to Standard Infusion Set by Leigh Steed et at. Dated Nov. 8, 2003.

* cited by examiner

*Primary Examiner* — Quynh-Nhu H Vu
(74) *Attorney, Agent, or Firm* — Greenblum & Bernstein, P.L.C.

(57) ABSTRACT

Fluid delivery device includes a body, a cannula adapted to extend into subcutaneous tissue, and a septum member adapted to allow a needle to puncture the septum member and to reseal the puncture once the needle is withdrawn from the puncture. The septum member is at least one of; a cap-shaped member, a member having at least two non-parallel walls that can each be punctured by a needle, and a member having a generally planar wall and a generally cylindrical wall which can each be punctured by a needle.

33 Claims, 60 Drawing Sheets

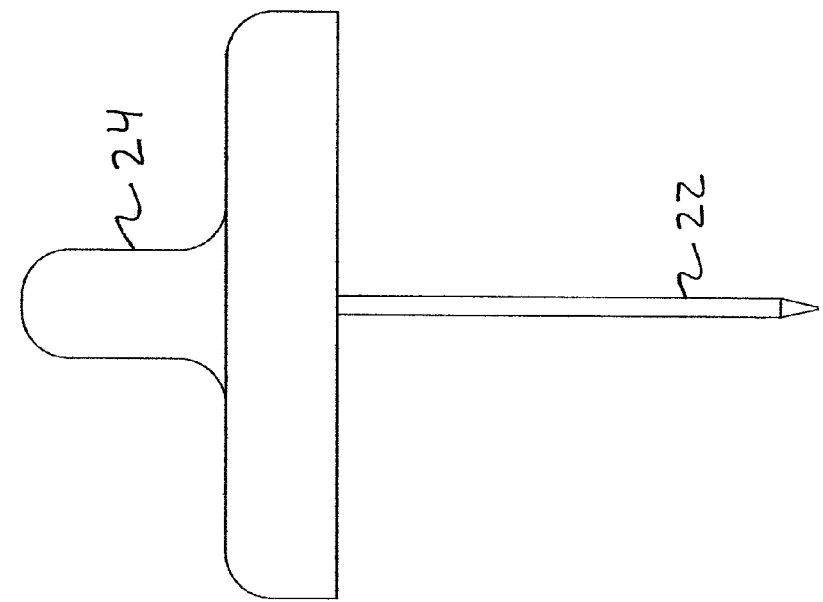
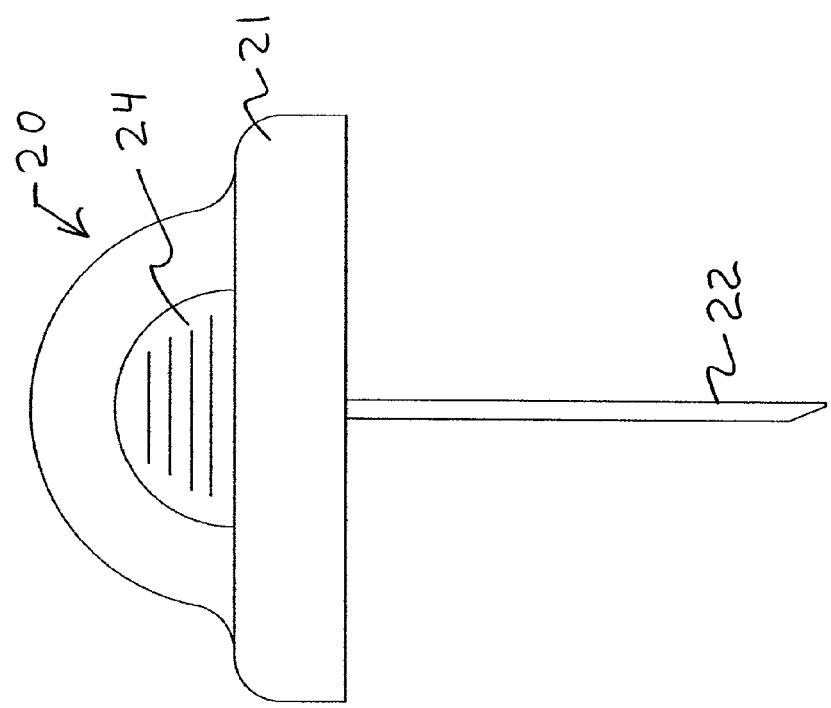

Fig. 19
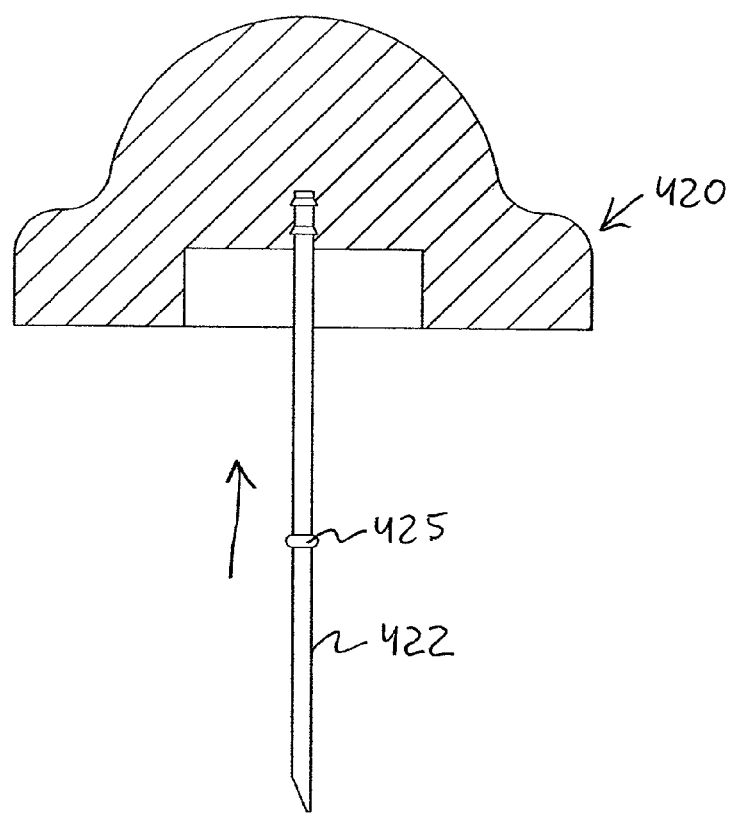
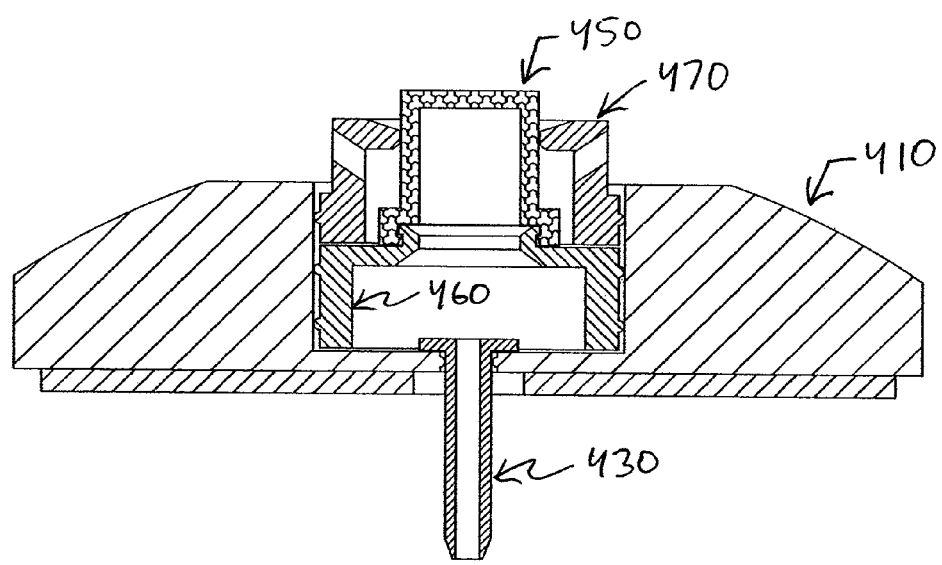

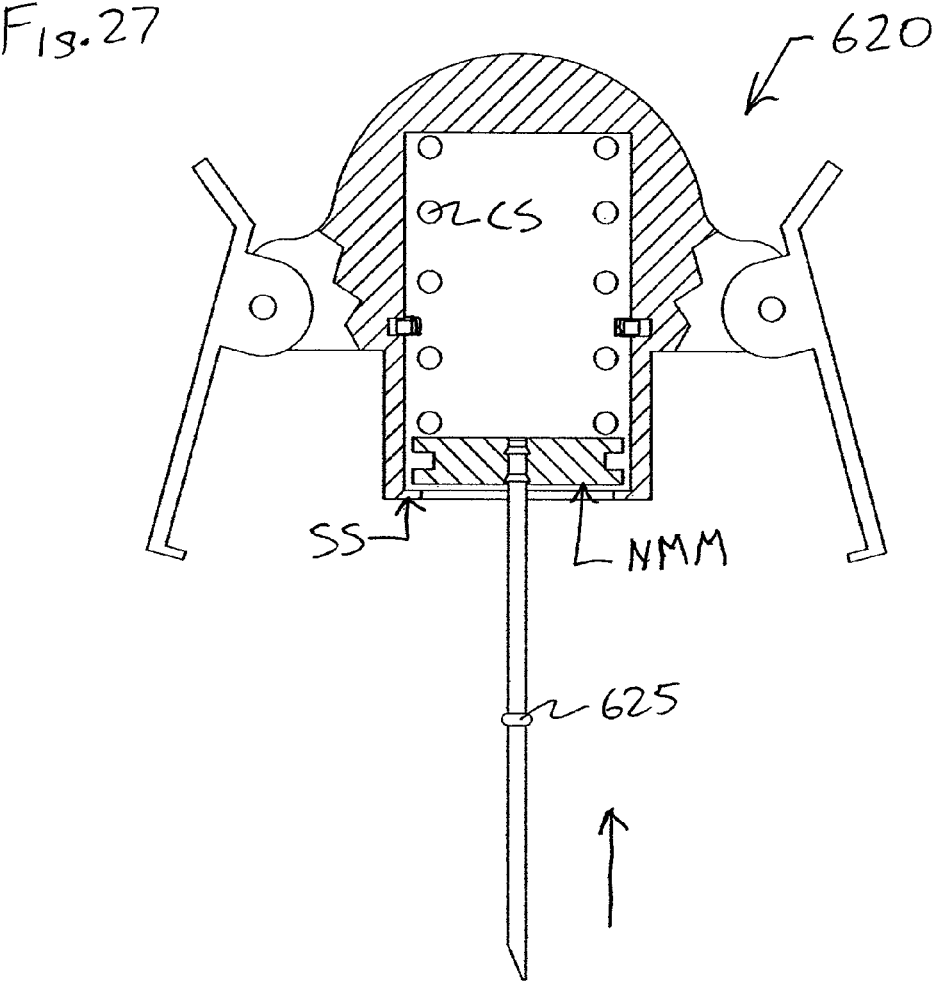
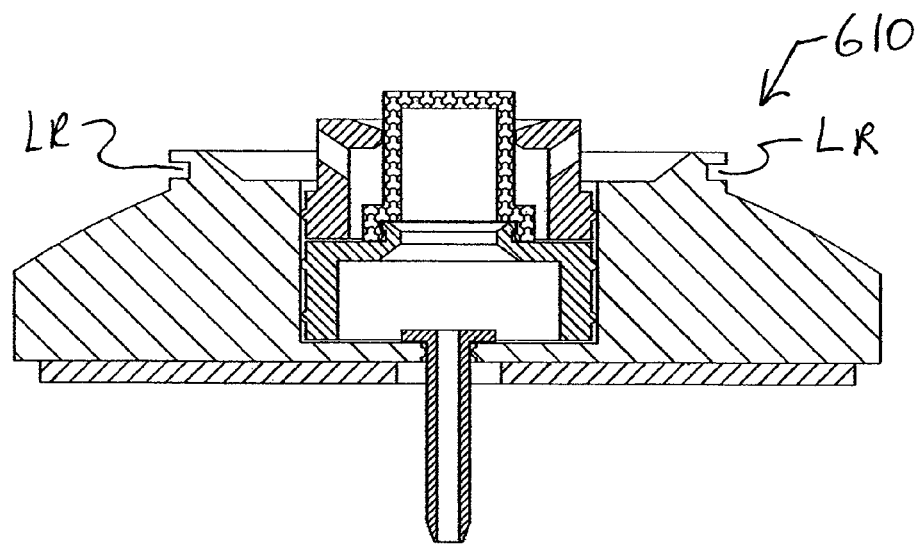
Fig. 27

Fig. 31
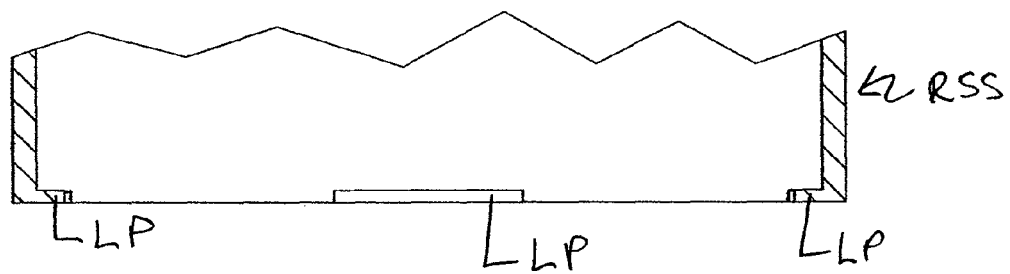
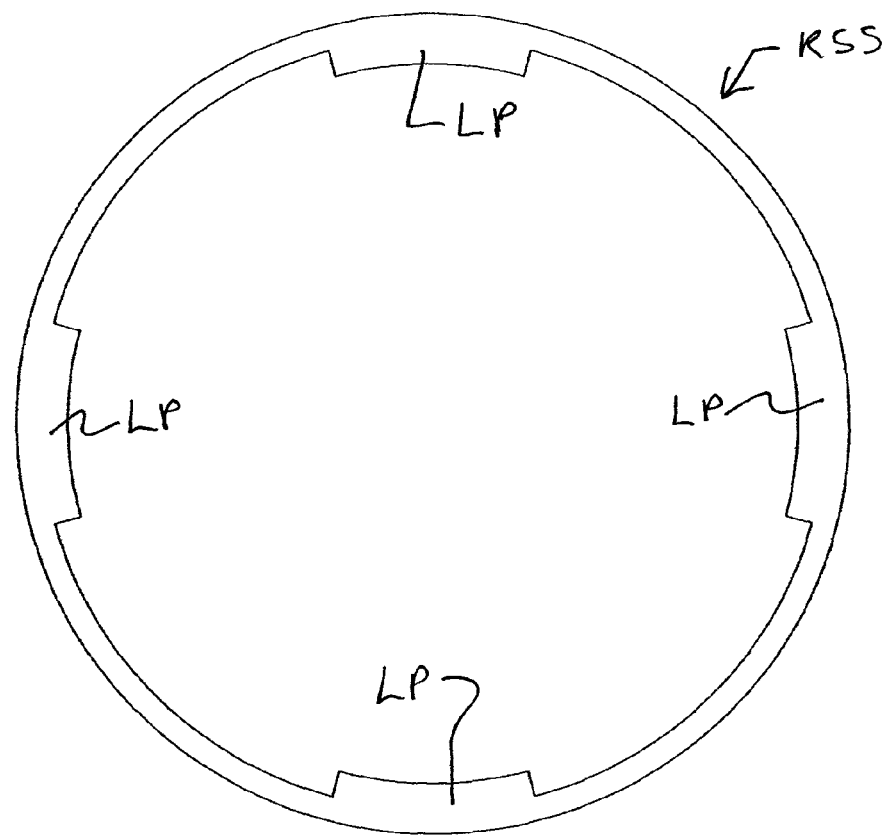
Fig. 32

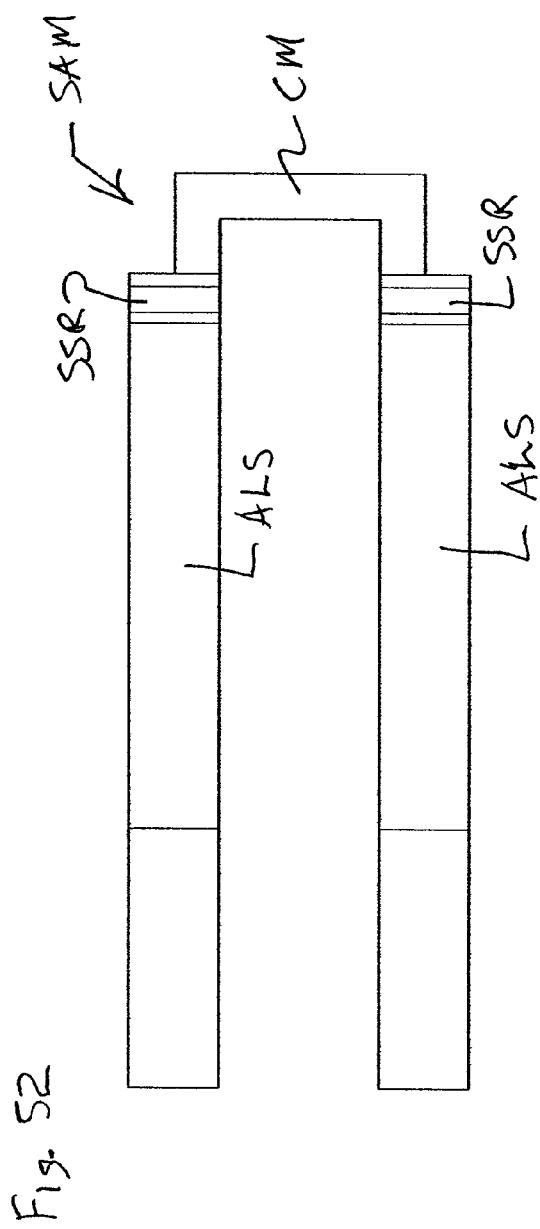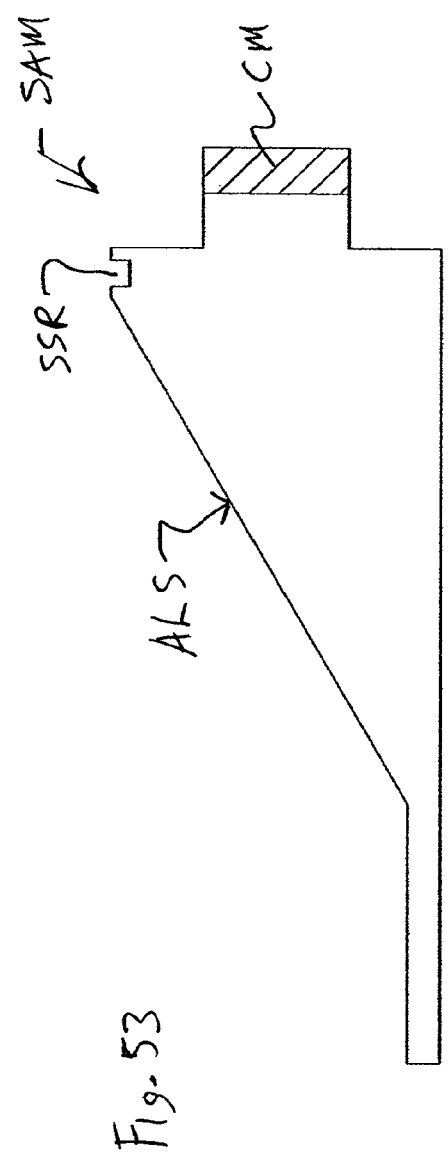
Fig. 52
Fig. 53

INFUSION DEVICE AND METHOD OF USING AND MAKING THE SAME

BACKGROUND OF THE INVENTION

1. Field of the Invention

The invention generally relates to devices that can be inserted in and/or coupled to humans or animals in order to facilitate fluid introduction through a skin surface. The fluid may be, e.g., medications. The invention also relates to systems and/or methods for introducing such fluids using such devices.

2. Description of Related Art

Examples of devices that can be used to deliver fluids to a living being include: U.S. Pat. No. 4,755,173; U.S. Pat. No. 5,954,643; U.S. Pat. No. 6,302,866; U.S. Pat. No. 6,368,141; U.S. Pat. No. 6,884,230; U.S. Pat. No. 6,949,084; U.S. Pat. No. 6,960,192; U.S. Pat. No. 6,997,907; U.S. Pat. No. 7,052,483; and U.S. Patent Application Publication 2007/0135774. The entire disclosure of each of these documents is hereby expressly incorporated by reference.

SUMMARY OF THE INVENTION

According to one non-limiting aspect of the invention, there is provided a fluid delivery device comprising a body, a cannula adapted to extend into subcutaneous tissue, and a septum member adapted to allow a needle to puncture the septum member and to reseal the puncture once the needle is withdrawn from the puncture. The septum member comprises at least one of; a cap-shaped member, a member having at least two non-parallel walls that can each be punctured by a needle, and a member having a generally planar wall and a generally cylindrical wall which can each be punctured by a needle.

The body may comprise an adhesive layer structured and arranged to at least temporarily secure the device to a user's skin.

The device may further comprise a removable needle insertion mechanism having a portion which extends through the cannula and another portion which can be gripped by a user.

The device may further comprise a support member comprising a first opening arranged over a one portion of the septum member and at least one second opening arranged over a different portion of the septum member. At least one of; the first opening comprises an axial opening and the at least one second opening comprises a generally circumferential opening or slot, the first opening comprises an axial opening and the at least one second opening comprises a opening whose center axis is oriented at an angle between an axis of the first opening and a radial plane perpendicular to the axis of the first opening, and the first opening comprises an axial opening and the at least one second opening comprises at least two equally angularly spaced openings.

The cannula may comprise a center axis that is oriented at an angle between a vertical center axis of the body and a radial plane perpendicular to the vertical center axis of the body. The cannula may be oriented at an angle that is not perpendicular to a bottom surface of the body.

The device may further comprise a needle insertion mechanism configured to cause movement of the cannula from a first position to a second position. The cannula may be movable from an initial retracted position to a puncturing position. The cannula may be movable from an initial retracted position within the body to an extended position wherein a puncturing portion of the cannula is arranged outside the body.

The device may further comprise a removable safety device structured and arranged to prevent movement of the cannula from a first position to a second position.

The device may further comprise a manually activated needle insertion mechanism configured to cause movement of the cannula from a first position to a second position.

The device may further comprise a trigger activated needle insertion mechanism configured to cause movement of the cannula from a first position to a second position.

The device may further comprise a needle insertion mechanism configured to automatically cause movement of the cannula from a first position to a second position.

The device may further comprise a needle insertion mechanism comprising a biasing mechanism for causing movement of the cannula from a first position to a second position.

The device may be adapted to function with a removable needle insertion mechanism and a tool comprising a biasing mechanism for causing movement of the cannula from a first position to a second position. The device may be adapted to function with a removable needle insertion mechanism and a trigger activated tool comprising a biasing mechanism and a movable member for causing movement of the cannula from a first position to a second position.

The device may further comprise a system for causing movement of the cannula from a first position to a second position.

The device may further comprise a system for causing movement of the cannula from an extended position to a retracted position and/or an arrangement or system for adjusting a cannula penetrating depth.

The device may further comprise a removable cannula insertion mechanism adapted to move the cannula to a puncturing position.

The device may further comprise at least one of; an adjustable septum support member adapted to move the septum between at least two angular positions, and a swivel mounted septum support member adapted to move the septum between at least two angular positions.

The invention also provides for a fluid delivery device comprising a body, a cannula adapted to extend into subcutaneous tissue, an insertion mechanism adapted to be gripped by a user and adapted to facilitate insertion of the cannula into the subcutaneous tissue, a septum member adapted to allow a needle to puncture the septum member and to reseal the puncture once the needle is withdrawn from the puncture. The septum member may comprise at least one of a cap-shaped member, a member having at least two non-parallel walls that can each be punctured by a needle, and a member having a generally planar wall and a generally cylindrical wall which can each be punctured by a needle.

The invention also provides for a fluid delivery device comprising a body, a cannula adapted to extend into subcutaneous tissue, an insertion mechanism adapted to be gripped by a user and comprising a needle portion adapted to facilitate insertion of the cannula into the subcutaneous tissue, a septum member adapted to allow a needle to puncture the septum member and to reseal the puncture once the needle is withdrawn from the puncture. The septum member may comprise at least one of a cap-shaped member, a member having at least two non-parallel walls that can each be punctured by a needle, and a member having a generally planar wall and a generally cylindrical wall which can each be punctured by a needle.

The invention also provides for a method of making the fluid delivery device of the type described above, wherein the method comprises mounting a cannula and a septum to a body.

The invention also provides for a method of using the fluid delivery device of the type described above, wherein the method comprises attaching the device to a user's skin and inserting a portion of the cannula into the subcutaneous tissue.

In non-limiting embodiments of the present fluid delivery devices, systems and methods, such embodiments may be used to deliver fluid such as insulin to users such as humans with, e.g., diabetes. In non-limiting embodiments of the present fluid delivery devices, the devices may be configured to be worn for an extended period of time (e.g., multiple days) and allow a user to inject a fluid (such as a physician-prescribed drug) into the user's body without the need to repeatedly puncture the user's skin with a needle. The present fluid delivery devices, systems and methods include many different features that distinguish them from prior devices, and certain of those features are different in many ways from the features of prior devices. Different embodiments of the present fluid delivery devices, systems and methods include one or more of these features, which are interchangeable between embodiments to the extent that they are not inconsistent with the other features of a given embodiment.

Non-limiting embodiments of the present fluid delivery devices include, broadly, a body, a cannula, a needle guide, and a septum. The body may be made from a one-piece member or alternatively one or more pieces, such as, e.g., two pieces. The body may include one or more fluid delivery passageways. One or more of the fluid delivery passageways may be oriented at a non-parallel angle to the normal direction of installation of the device. In some embodiments that include two or more fluid delivery passageways, one the of the passageways may extend into and be angled with respect to another. In non-limiting multi-fluid delivery passageway embodiments, some or all of the fluid delivery passageways may be defined in part by a fitting adapted to be releasably coupled to an infusion pump connector fitting. In non-limiting embodiments, the device may allow for fluid delivery from a pump and fluid delivery from another structure, such as a syringe.

By way of non-limiting example, the cannula and the body of the devices may be integrally formed, such that the cannula comprises a tube-like structure that extends outwardly from the body (e.g., from the bottom surface of the body). The devices also may include an insertion device that is coupled to the body and that may be used to aid in insertion of the device, and a needle guard that is coupled to the body and that may be used to protect users from inadvertent needle sticks. In some embodiments of the present fluid delivery devices, a rigid cannula may be used instead of a needle guide and a soft cannula.

Non-limiting embodiments of the present systems (which may be characterized as fluid delivery systems) include one or more of the present fluid delivery devices that have been sterilized and enclosed in a package, with or without instructions for use contained within the package.

Non-limiting embodiments of the present methods (which may be characterized as fluid delivery methods) include installing one of the present fluid delivery devices on a user, and delivering fluid through the device and into the user.

BRIEF DESCRIPTION OF THE DRAWINGS

The present invention is further described in the detailed description which follows, in reference to the noted plurality of drawings by way of non-limiting examples of exemplary embodiments of the present invention, in which like reference numerals represent similar parts throughout the several views of the drawings, and wherein:

FIGS. 6 and 7 show front and right-side views of the insertion mechanism used in the embodiment of FIG. 1;

FIG. 19 shows the device of FIG. 17 with the insertion mechanism in a removed position;

FIG. 27 shows the device of FIG. 23 with the insertion mechanism in a removed position;

FIG. 31 shows a side cross-section view of a bottom portion of the insertion mechanism shown in FIG. 29;

FIG. 32 shows a bottom view of FIG. 31;

FIG. 33 shows the triggering system in an initial un-triggered position;

FIG. 52 shows a top view of the safety actuator mechanism used in the device of FIG. 49;

FIG. 53 shows a side cross-section view of FIG. 52;

DETAILED DESCRIPTION OF THE INVENTION

Figure 1:
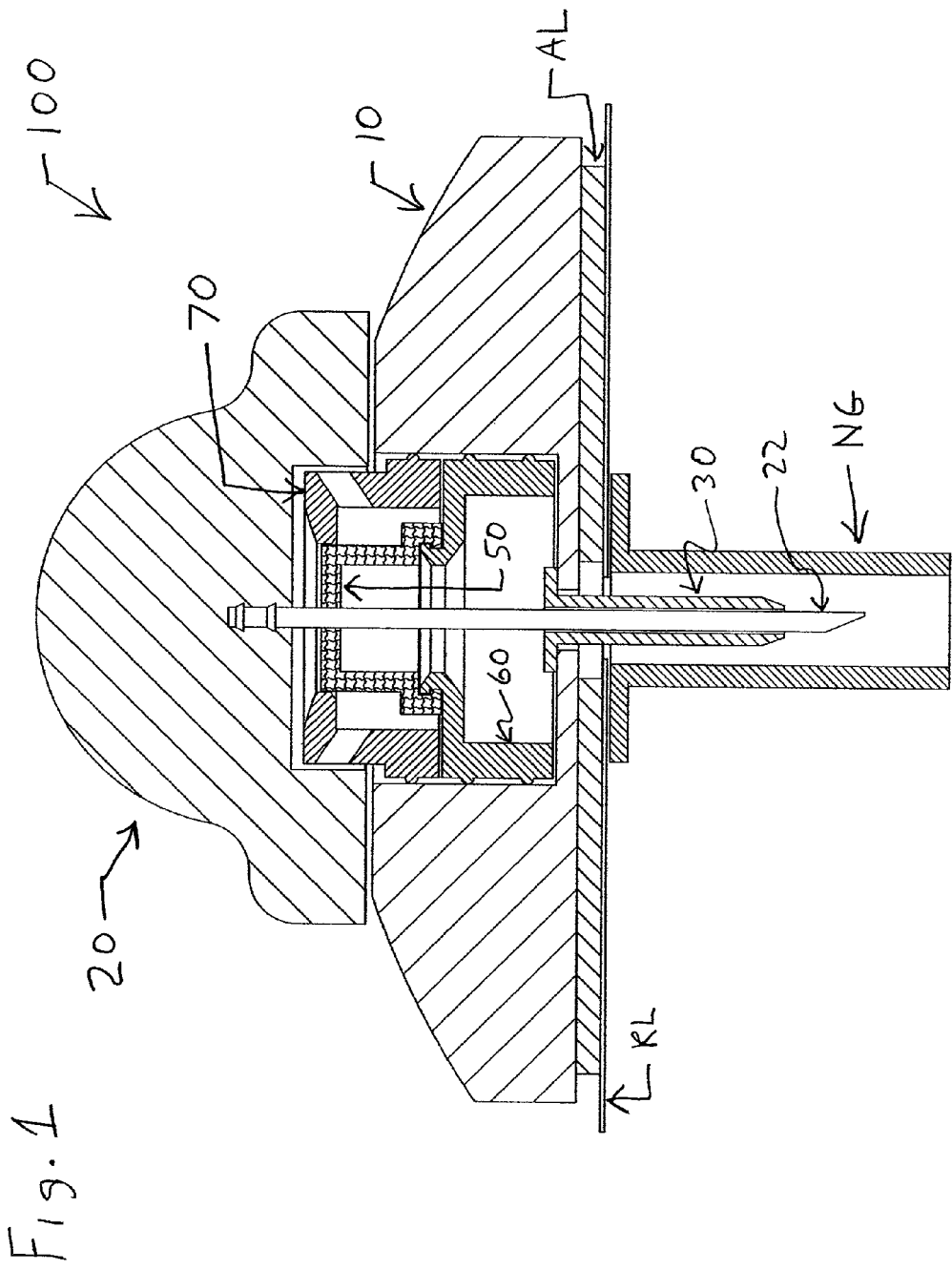
FIG. 1 shows a cross-section view of a first non-limiting embodiment of the fluid delivery device according to the invention. The insertion needle is not shown in cross-section.

The figures illustrate by way of example and not limitation. Identical reference numbers generally indicate an identical structure. Reference numbers which are different by increments of 100, e.g., 10 and 110, may be used to indicate a similar feature or a feature with similar functionality, as may non-identical reference numbers. Every feature of each embodiment is not always labeled in every figure in which that embodiment appears, for purposes of clarity. The figures are drawn to scale, meaning the sizes of the depicted elements are accurate relative to each other for each of the disclosed embodiments of the present fluid delivery devices.

The terms "comprise" (and any form of comprise, such as "comprises" and "comprising"), "have" (and any form of have, such as "has" and "having"), "contain" (and any form of contain, such as "contains" and "containing"), and "include" (and any form of include, such as "includes" and "including") are open-ended linking verbs. As a result, a device, a system and/or a method that "comprises," "has," "contains," or "includes" one or more recited elements or steps possesses those recited elements or steps, but is not limited to possessing only those elements or steps; it may possess elements or steps that are not recited. Likewise, an element of a device, system and/or method that "comprises," "has," "contains," or "includes" one or more recited features possesses those features, but is not limited to possessing only those features; it may possess features that are not recited. Furthermore, a structure that is configured in a certain way is preferably configured in at least that way, but also may be configured in a way or ways that are not specified.

Thus, and by way of example, a fluid delivery device comprising a body having a first inlet, a first fluid delivery passageway extending from the first inlet, and a second fluid delivery passageway, a cannula having a portion that is coaxial with a portion of one of the first and second fluid delivery passageways, and a septum member comprises at least one of a cap-shaped member, a member having at least two non-parallel walls that can each be punctured by a needle, and a member having a generally planar wall and a generally cylindrical wall which can each be punctured by a needle, but is not limited to possessing only the recited elements (thus, other non-recited elements are not excluded). For example, the fluid delivery device also may include a septum member having more than one layer and/or more that one septum members.

In any of the claims, the term "consisting of" or "consisting essentially of" may be substituted for any of the open-ended linking verbs recited above, in order to change the scope of a given claim from what it would otherwise be using the open-ended linking verb.

The terms "a" and "an" are defined as one or more than one unless the disclosure and/or claim explicitly requires otherwise. The terms "substantially" is defined as at least close to (and includes) a given value or state (preferably within 10% of, more preferably within 1% of, and most preferably within 0.1% of).

The fluid delivery devices according to the invention may be used to deliver fluid to a living being for any of a variety of reasons. For example, some embodiments of the present fluid delivery devices may be used to deliver insulin to the subcutaneous tissue of a person with diabetes. However, embodiments of the present fluid delivery devices also may be used to deliver other fluids, such as saline, medication other than insulin, chemicals, enzymes, antigens, hormones, vitamins or the like, into subcutaneous tissue, subcutaneous fat tissue, or other types of tissue, such as the epidermis, dermis, and different types of sub-dermal tissue such as muscle. The embodiments of the present fluid delivery devices shown in the figures are adapted for use with humans; however, those of ordinary skill in the art will, in light of this disclosure, understand that other embodiments may be adapted for use with animals.

The fluid delivery devices according to the invention may be characterized as ports, fluid delivery ports, injection ports, injection aides, infusion ports or infusion devices. The fluid delivery systems may be characterized as injection systems or infusion systems.

FIGS. 1-13 show a first non-limiting embodiment of the fluid delivery device according to the invention. With reference to FIG. 1, fluid delivery device 100 includes a one-piece body 10. However, it may also be multi-piece body. Device 100 also includes removable insertion device 20 that has needle portion 22 that is inserted into body 10, and a needle guard NG that is coupled to a bottom portion of the body 10. The needle guard NG may be coupled to the body 10 in any desired way such as, e.g., a friction fit, or any other suitable system of releasable attachment or engagement. Device 100 also includes a generically-depicted adhesive layer AL, which preferably includes a protective backing sheet or release layer RL. Adhesive layer AL may have the form of a circular pad having two opposing, adhesive-coated sides, one of which is attached to the relevant portion of the bottom surface of body 10 and the other of which will be attached to a user's body (e.g., once a backing sheet has been removed). Alternatively, one of the two opposing sides may be welded (e.g., ultrasonically welded) to the bottom surface of body 10 instead of being attached via an adhesive. As opposed to using an adhesive layer AL, a portion (e.g., all) of the bottom surface of body 10 may be configured to adhere directly to a living being's skin, such as by making the bottom surface material from a material that chemically reacts with and adheres to skin. Adhesive layer AL is one example of an adhesive portion (of a fluid delivery device) that is configured to adhere directly to a living being's skin. Device 100 also includes a cannula 30 which has one portion extending out past from the adhesive layer AL and another portion arranged within the body 10. Device 100 additionally includes a bottom support 60, a septum cap 50 coupled to the bottom support 60 and an upper support 70. The term "septum" as used herein is intended to refer to a material having one or more layers which can be punctured and which is self-sealing such that fluid can pass through the material via a puncturing device that has penetrated the material, but cannot pass through the material after the device causing the puncture is removed.

With reference to FIGS. 6 and 7, insertion device 20 comprises an insertion needle 22 connected to an insertion device hub 21. As shown in FIG. 1, a portion of insertion needle 22 extends out past the bottom end of the cannula 30 and is exposed when insertion device 20 is fully inserted in body 10. One manner in which this exposure is accomplished is by providing insertion device hub 21 with a recess sized to accommodate the upper end of upper support 70 (see FIG. 1) when insertion device 20 is fully inserted in body 10. The insertion needle can be a solid needle as in known in the art and can have its upper end press-fit or otherwise non-removably secured to the hub 21.

Body 10 and insertion device 20 may be configured such that insertion device 20 cannot rotate with respect to body 10 when fully inserted in body 10. One manner of achieving this configuration comprises providing hub 21 with rotation-restricting protrusions (not shown), which extend in a downstream or downward direction from the hub 21 and which extends into corresponding recesses in the body 10 (not shown). In this way, when insertion device 20 is fully inserted in body 10, at least a portion of each protrusion would extend into each recess such that the recess side walls interfere with the protrusions to prevent rotation of the insertion device 20 relative to body 10. Although the embodiment shown in FIGS. 1-13 shows no protrusions and recesses, a system of the type disclosed in US 2007/0135774 can be utilized on one or more of the embodiments disclosed herein.

Figure 2:
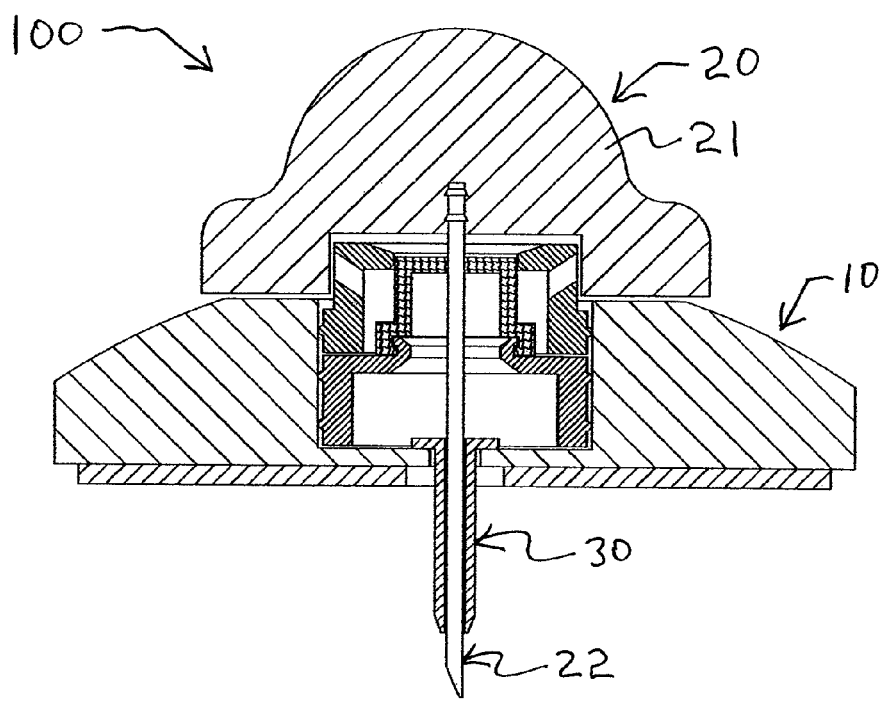
FIG. 2 shows the device of FIG. 1 with the needle guard and the removable layer removed.
Figure 3:
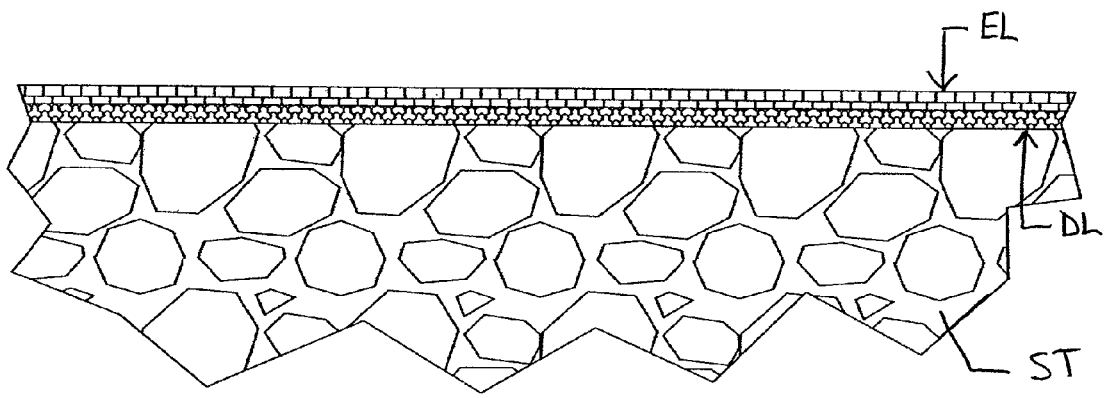
FIG. 3 shows a cross-section of a portion of a user's body and illustrates the epidermis layer of skin, the dermis layer of skin, and an underlying subcutaneous tissue.
Figure 4:
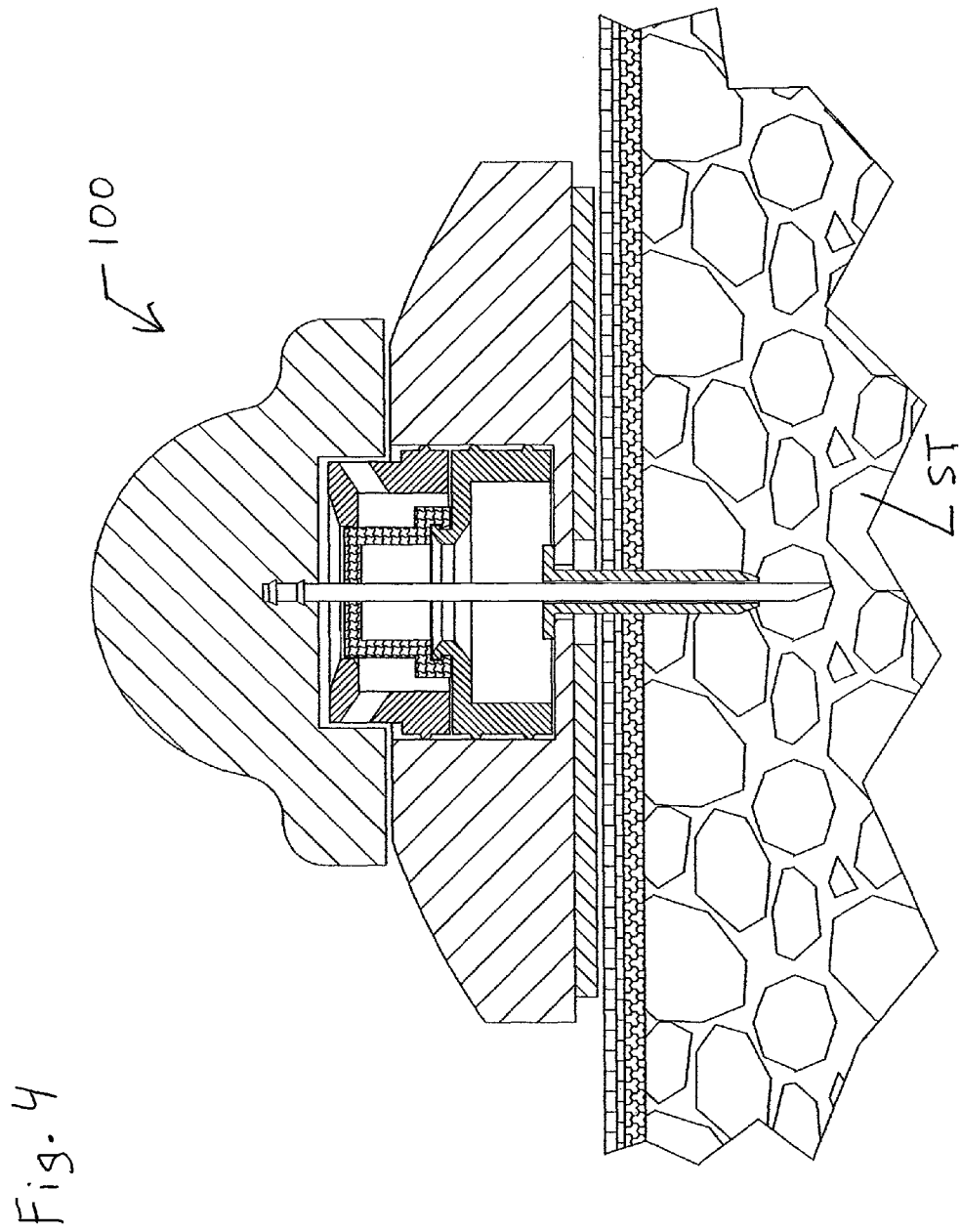
FIG. 4 shows the device of FIG. 2 in an installed position, i.e., the device shown in FIG. 2 is attached to the portion of the user's body shown in FIG. 3 and illustrates an adhesive layer of the device secured to the epidermis layer of the skin and the cannula penetrating into the underlying subcutaneous tissue.
Figure 5:
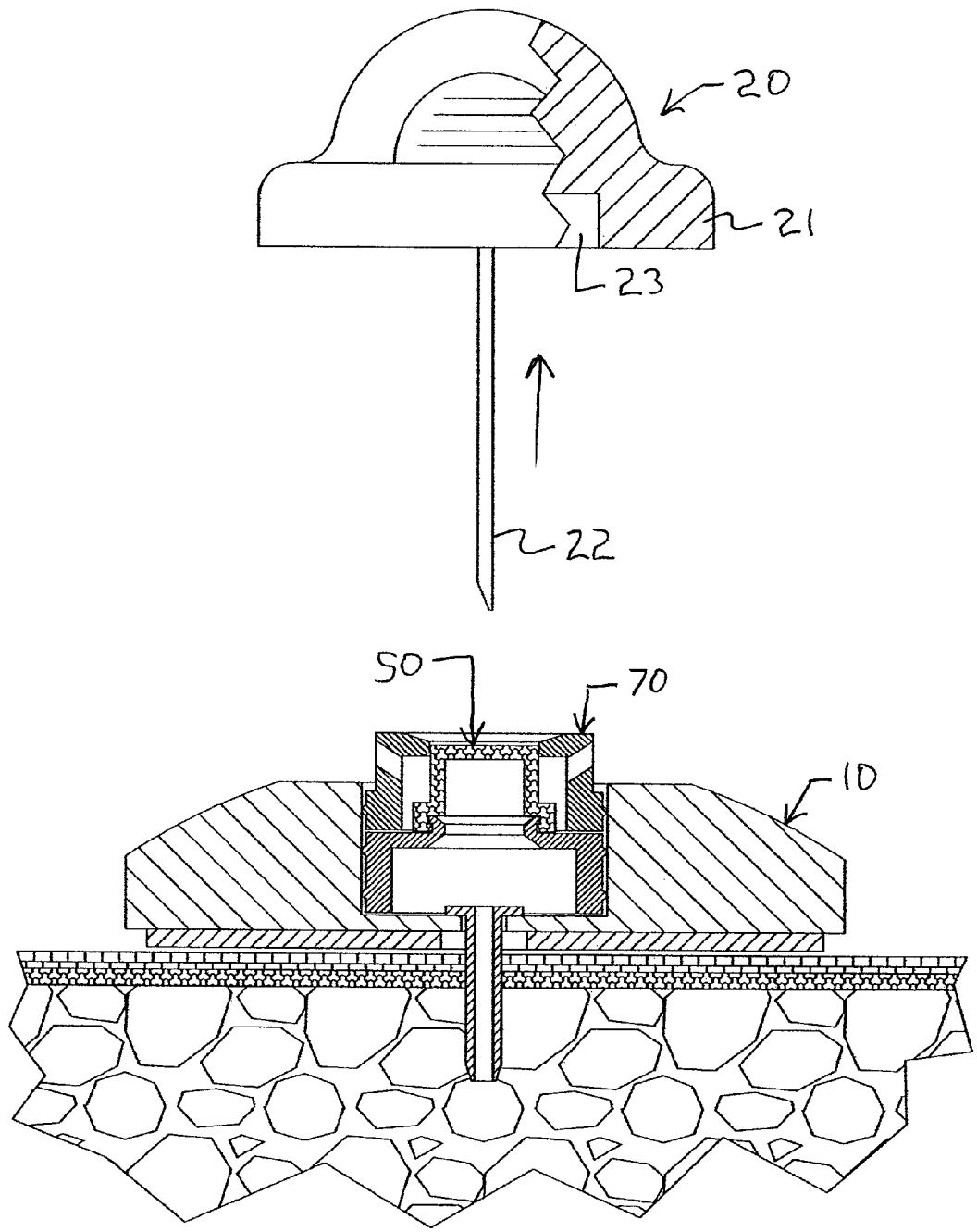
FIG. 5 shows the device of FIG. 4 with the insertion mechanism in a removed position.

With reference to FIGS. 2-5, there is shown one non-limiting way in which the device 100 can be installed on a user. FIG. 2 shows the device 100 with the needle guard NG and the removable layer RL removed. FIG. 3 shows a cross-section of a portion of a user's body and illustrates the epidermis layer EL of skin, the dermis layer DL of skin, and an underlying subcutaneous tissue ST. FIG. 4 shows the device 100 in an installed position, i.e., the device 100 is attached to the portion of the user's body shown in FIG. 3 and illustrates the adhesive layer AL of the device 100 secured to the epidermis layer EL of the skin and the cannula 30 penetrating into the underlying subcutaneous tissue ST. FIG. 5 shows the device 100 with the insertion mechanism 20 in a removed position.

Figure 8:
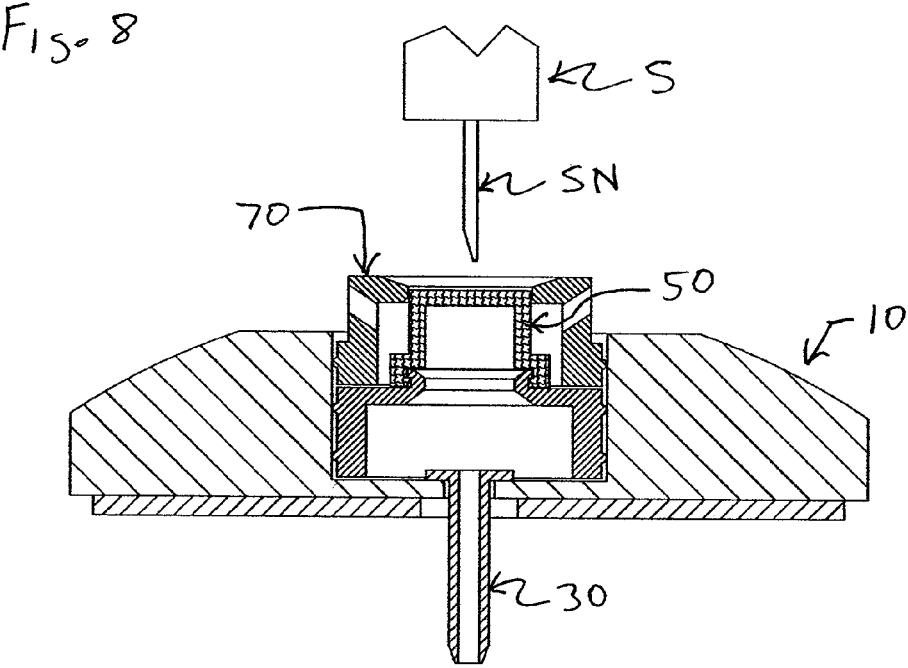
FIGS. 8 and 9 show cross-section views of the device of FIG. 1 in an installed configuration (the user's skin is not shown for clarity), and illustrate how a syringe can be used to inject fluid into the device along a direction of device installation so that it can flow through the cannula into the underlying subcutaneous tissue.
Figure 9:
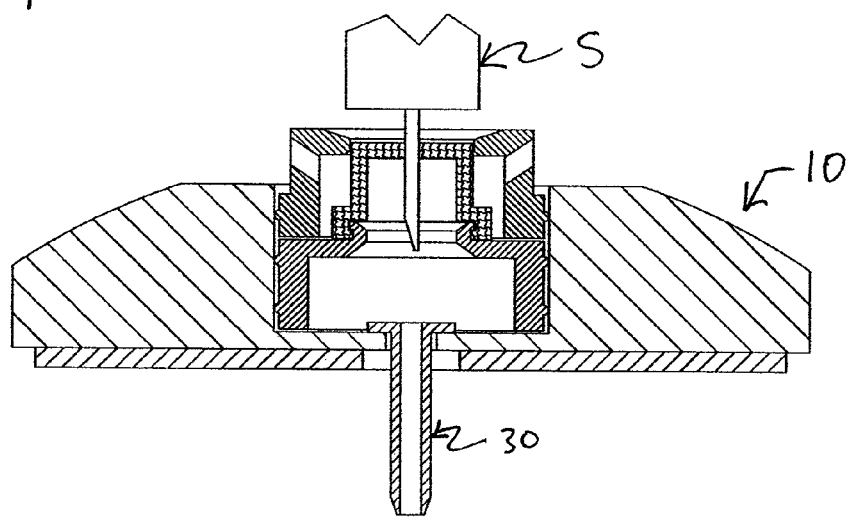
Figure 10:
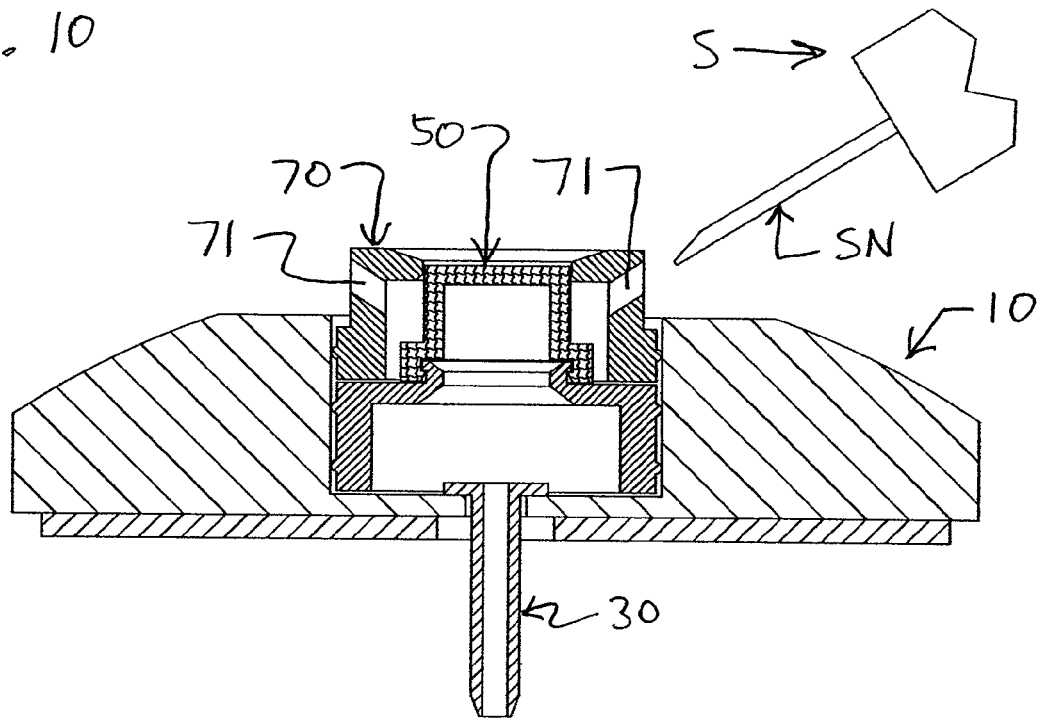
FIGS. 10 and 11 show cross-section views of the device of FIG. 1 in an installed configuration (the user's skin is not shown for clarity), and illustrate how a syringe can be used to inject fluid into the device along a side-angled direction, i.e., a direction that is not parallel to a device installation direction, so that it can flow through the cannula into the underlying subcutaneous tissue.
Figure 11:
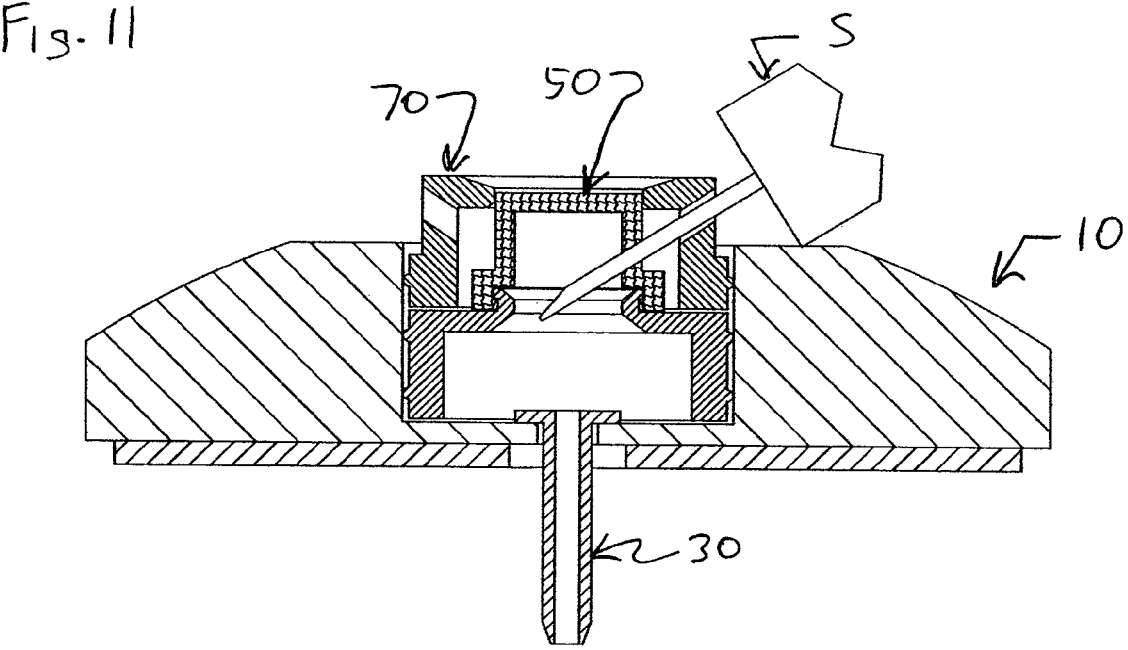
Figure 12:
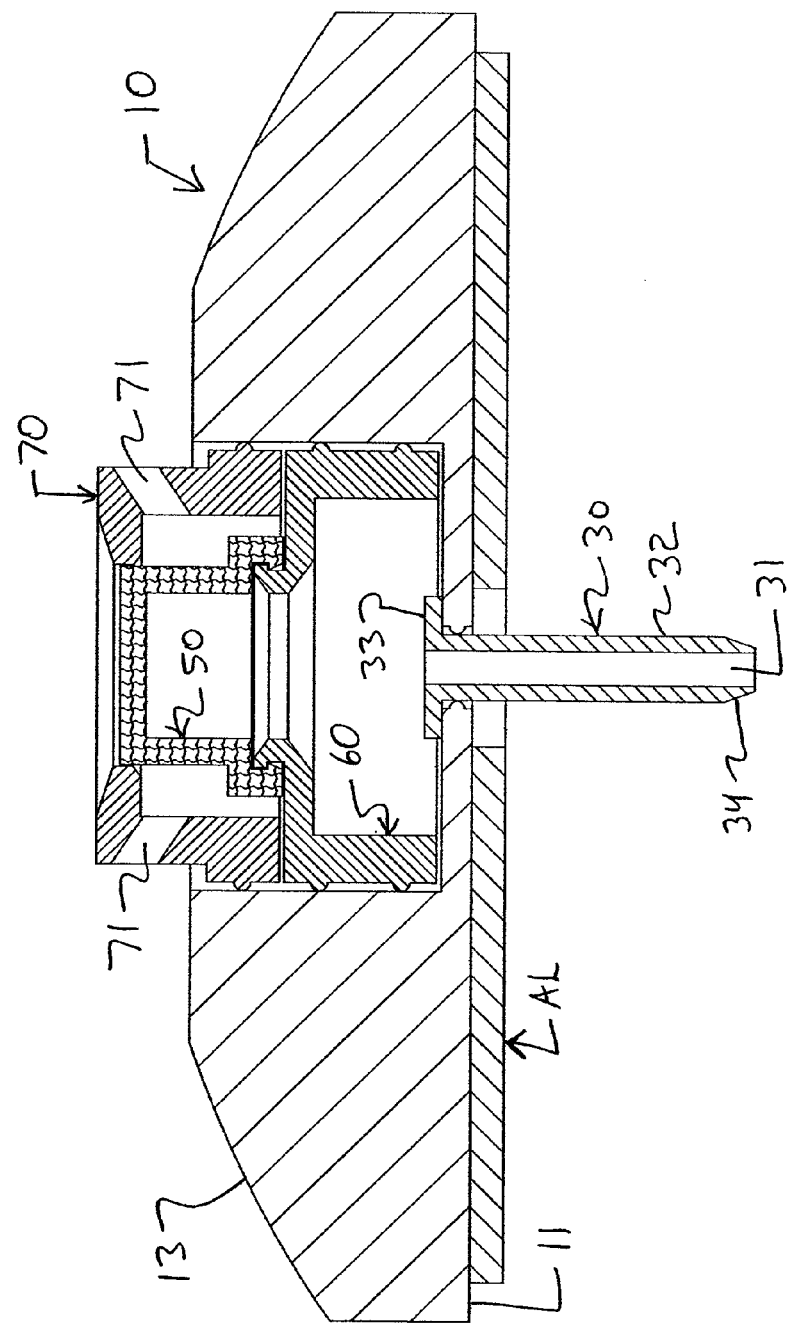
FIG. 12 shows an enlarged cross-section view of the device of FIG. 1 with the insertion mechanism removed.

With reference to FIGS. 8-11, there is shown one non-limiting way in which the device 100 can be used to transfer fluids from a syringe S into the user. FIGS. 8 and 9 illustrate how a syringe S can be used to inject fluid into the device 100 along a direction of device 100 installation so that it can flow through the cannula 30 into the underlying subcutaneous tissue ST. FIGS. 10 and 11 illustrate how a syringe S can be used to inject fluid into the device 100 along a side-angled direction, i.e., a direction that is not parallel to a device installation direction, so that it can flow through the cannula 30 into the underlying subcutaneous tissue ST. The syringe or injection device S has a needle SN which can be inserted into fluid delivery device 100. The injection device may be used to inject fluid (e.g., insulin) into the subcutaneous tissue ST of a user. The depicted embodiment of injection device S can be a standard syringe that includes a generically-depicted plunger portion and an injection structure that includes a standard syringe needle. Other injection devices may be used with embodiments of the present fluid delivery devices to deliver fluid to a user. In this embodiment, the openings 71 comprise needle guides which protects the cannula 30 from being contacted by the injection needle SN.

Figure 13:
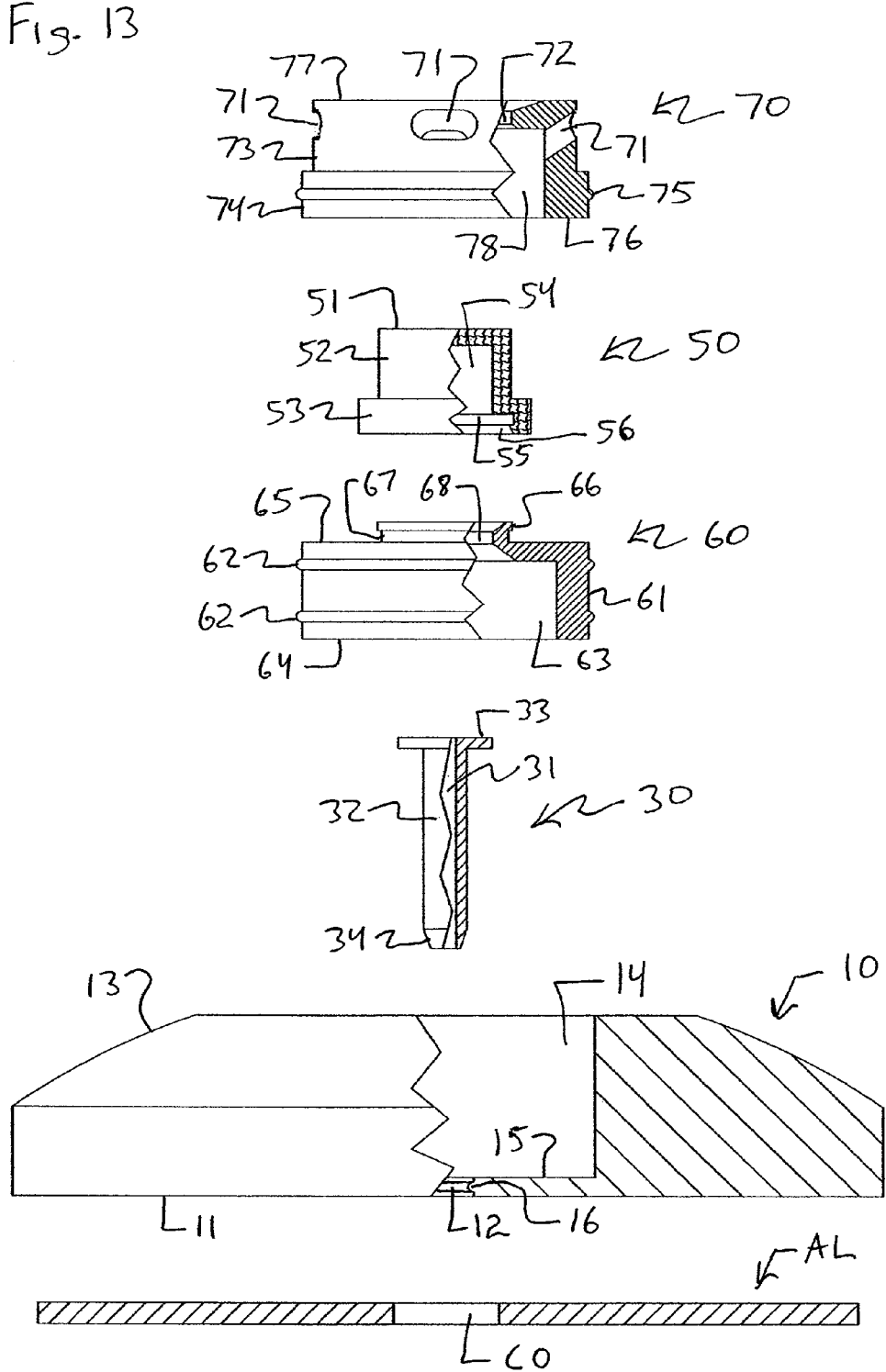
FIG. 13 shows an exploded view of FIG. 12 with the upper support, the septum cap, the lower support, the cannula, and the body shown in partial cross-section and with the adhesive layer shown in cross-section.

With reference to FIG. 13, body assembly portion of the device 100, which is shown in exploded form, includes an adhesive layer AL. As explained above, the adhesive layer AL can be a one-piece member having opposite facing adhesive surfaces. Alternatively, the layer AL can have the form of an adhesive coating which is applied to the bottom surface of the body 10. The adhesive layer AL is preferably disk-shaped, i.e., substantially circular, in order to correspond to the circular bottom surface 11 of the body and has a central circular cannula opening CO which allows the cannula 30 to pass therethrough. Non-limiting axial thickness ranges for the adhesive layer AL can be between about 0.001 inches to about 0.100 inches, and is preferably between about 0.005 inches and about 0.050 inches. The adhesive layer AL can also be of any type and/or material which is used in the art for medical devices including, e.g., similar fluid delivery devices, provided it functions for its intended purpose consistent with the invention.

Again with reference to FIG. 13, body assembly portion of the device 100 also includes a body 10 which can be a one-piece synthetic resin member made of medical grade plastics including those currently used to make known fluid delivery devices. By way of non-limiting example, the body 10 has a substantially circular bottom surface 11, an opening 12 which is sized to allow the cannula 30 to pass therethrough. The opening 12 can preferably include one or more sealing projections 16 which prevent fluid from leaking past the joint between the cannula 30 and the opening 12. Alternatively, the opening 12 can include a sealing recess (not shown) which receive therein a sealing projection formed on the cannula 30. Such a configuration would also ensure that the cannula 30 becomes axially retained within the opening 12. The body also includes a main generally cylindrical central opening 14 which is sized and configured to receive therein an injection module which includes the cannula 30, the lower support 60, the septum cap 50 and the upper support 70. A bottom surface 15 defines a bottom of the opening 14. An upper area of the body 10 preferably includes a generally chamfered or rounded area 13. Non-limiting axial thickness ranges for the body 10 can be between about 0.20 inches to about 0.75 inches, and is preferably between about 0.30 inches and about 0.60 inches. The body 10 can also be of any type and/or material which is used in the art for medical devices including, e.g., similar fluid delivery devices, provided it functions for its intended purpose consistent with the invention.

Again with reference to FIG. 13, body assembly portion of the device 100 also includes a cannula 30 which can be a one-piece synthetic resin member made of medical grade metals and/or plastics including those currently used to make known cannulas for fluid delivery devices. By way of non-limiting example, the cannula 30 has a substantially cylindrical body portion 32, a through opening 31 which is sized to allow an insertion needle 22 to pass therethrough, a flange portion 33, and a tapered puncturing end 34. Non-limiting axial length ranges for the cannula 30 can be between about 0.10 inches to about 0.60 inches, and is preferably between about 0.20 inches and about 0.30 inches. The cannula 30 can also be of any type and/or material which is used in the art for medical devices including, e.g., similar fluid delivery devices, provided it functions for its intended purpose consistent with the invention.

Again with reference to FIG. 13, body assembly portion of the device 100 also includes a lower support 60 which can be a one-piece synthetic resin member made of medical grade plastics including those currently used to make known fluid delivery devices. By way of non-limiting example, the lower support 60 has a substantially ring-shaped bottom surface 64, a main central generally cylindrical space 63, an outer generally cylindrical surface 61 which preferably includes one or more sealing projections 62, a substantially ring-shaped upper surface 65, and an upper generally circular opening 68. A generally circular flange 66 and recess 67 are arranged on an upper end of the lower support 60. Such a configuration ensures that the septum cap 50, and more specifically, the circular projection 56 and recess 55, becomes axially and sealingly retained/connected to the lower support 60. Upper and lower portions of the opening 68 are preferably chamfered so as not to interfere with insertion of, e.g., a syringe needle (see FIGS. 10 and 11). Non-limiting axial thickness ranges for the lower support 60 can be between about 0.10 inches to about 0.50 inches, and is preferably between about 0.15 inches and about 0.30 inches. The lower support 60 can also be of any type and/or material which is used in the art for medical devices including, e.g., similar fluid delivery devices, provided it functions for its intended purpose consistent with the invention.

Again with reference to FIG. 13, body assembly portion of the device 100 also includes a septum cap 50 which can be a one-piece synthetic member made of medical grade materials including those currently used to make known septum sealing members for fluid delivery devices. By way of non-limiting example, the septum cap 50 has a substantially cylindrical body portion 52, an upper circular surface 51, an inner space 54, a flange portion 53 which includes an internal circular projecting flange 56 and recess 55 which is sized and configured to secure the cap 50 to the lower support 60 and to also provide a sealed connection, i.e., prevent fluid leakage between the cap 50 and the lower support 60. Non-limiting axial length ranges for the septum cap 50 can be between about 0.10 inches to about 0.40 inches, and is preferably between about 0.20 inches and about 0.30 inches. The septum cap 50 can also be of any type and/or material which is used in the art for medical devices including, e.g., similar fluid delivery devices, provided it functions for its intended purpose consistent with the invention. Using the configuration of features 55, 56, 66 and 67, the cap 50 can be non-removably and/or permanently secured to the lower support 60. Permanently attached, as used herein, includes an attachment such that a user of the device will not be able to separate them without destroying or significantly impairing the usefulness of the device. An alternative way to achieve this type of permanent attachment is through the use of an adhesive or adhesives. It is also possible to utilize welding techniques such as laser welding, hot plate welding, vibration welding, and friction welding. Furthermore, in one, few, or all of the herein disclosed embodiments, the septum cap 50 (and/or e.g., puncturable portions of septum) may be artificially-colored (e.g., by adding a coloring agent to the material that forms the septum) in order to enhance the contrast between the septum and the remainder of the fluid delivery device 100.

Again with reference to FIG. 13, body assembly portion of the device 100 also includes an upper support 70 which can be a one-piece synthetic resin member made of medical grade plastics including those currently used to make known fluid delivery devices. By way of non-limiting example, the upper support 70 has a substantially ring-shaped bottom surface 76, a main central generally cylindrical space 78, an outer generally cylindrical surface 74 which preferably includes one or more sealing projections 75, a substantially ring-shaped upper surface 77, and an upper generally circular opening 72. Plural, e.g., four, circumferential slots or openings 71 are arranged on an upper end 73 of the upper support 70. Such a configuration ensures that a user can insert a syringe needle SN either through the axially aligned opening 72 (and into the septum cap surface 51 as shown in FIG. 9) and through one of the non-axially aligned openings 71 (and into the septum cap surface 52 as shown in FIG. 11). Non-limiting axial thickness ranges for the upper support 70 can be between about 0.10 inches to about 0.50 inches, and is preferably between about 0.15 inches and about 0.30 inches. The upper support 60 can also be of any type and/or material which is used in the art for medical devices including, e.g., similar fluid delivery devices, provided it functions for its intended purpose consistent with the invention.

Figure 14:
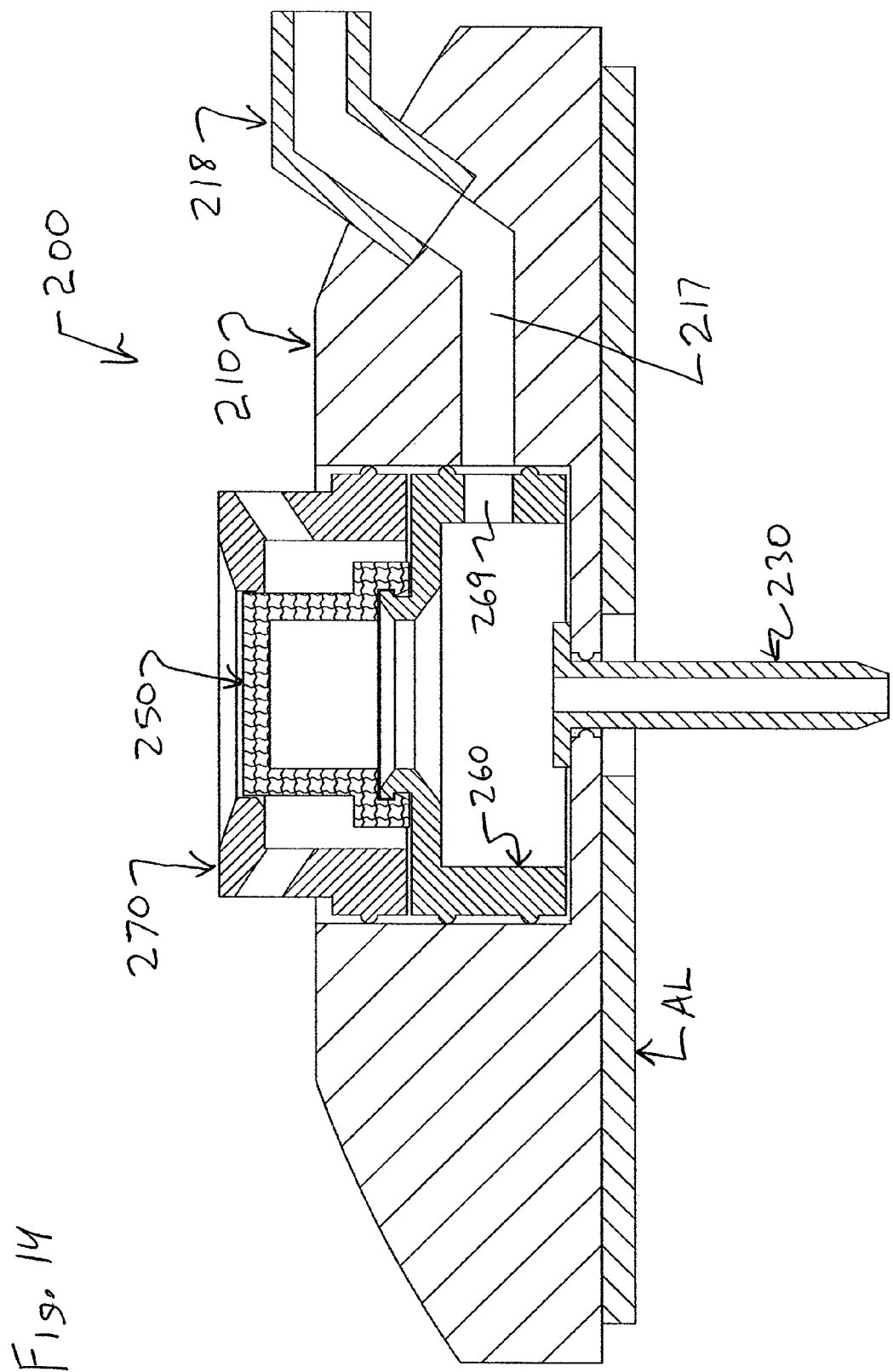
FIG. 14 shows a cross-section view of another non-limiting embodiment of the device. The insertion mechanism has been removed. This embodiment is similar to that of FIG. 1 except that it additionally includes internal passages and a connecting nipple for allowing fluid to enter into the body via, e.g., an infusion pump connected to the nipple via flexible tubing.

FIG. 14 shows another non-limiting embodiment of the device 200. The insertion mechanism (which can be similar or substantially identical to mechanism 20 in FIG. 1) has been removed, as have the needle guard NG and removable layer RL. This embodiment is similar to that of FIG. 1 except that it additionally includes an internal passage 269 formed in the lower support 260, an internal passage 217 formed in body 210, and a connecting nipple 218 coupled to the body 210 for allowing fluid to enter into the body 210 via, e.g., an infusion pump connected to the nipple via flexible tubing. Such a multi-inlet fluid delivery device 200 may be configured for connection to any type of infusion pump, and may optionally include a passageway closing structure (possibly arranged within opening 269 and/or nipple 218, that can be moved between positions. In one position, the passageway closing structure inhibits some fluid flow through the passageways.

As can be seen in FIG. 14, fluid delivery device 200 includes a one-piece body 210. However, it may also be multi-piece body. Device 200 also includes removable insertion device (not shown) that has needle portion that is inserted into body 210, and a needle guard that is coupled to a bottom portion of the body 210. The needle guard may be coupled to the body 210 in any desired way such as, e.g., a friction fit, or any other suitable system of releasable attachment or engagement. Device 200 also includes a generically-depicted adhesive layer AL, which preferably includes a protective backing sheet or release layer (not shown). Adhesive layer AL may have the form of a circular pad having two opposing, adhesive-coated sides, one of which is attached to the relevant portion of the bottom surface of body 210 and the other of which will be attached to a user's body (e.g., once a backing sheet has been removed). Alternatively, one of the two opposing sides may be welded (e.g., ultrasonically welded) to the bottom surface of body 210 instead of being attached via an adhesive. As opposed to using an adhesive layer AL, a portion (e.g., all) of the bottom surface of body 210 may be configured to adhere directly to a living being's skin, such as by making the bottom surface material from a material that chemically reacts with and adheres to skin. Adhesive layer AL is one example of an adhesive portion (of a fluid delivery device) that is configured to adhere directly to a living being's skin. Device 200 also includes a cannula 230 which has one portion extending out past from the adhesive layer AL and another portion arranged within the body 210. Device 200 additionally includes a bottom support 260, a septum cap 250 coupled to the bottom support 260 and an upper support 270. With the exception of passage 269, the lower support 260 can be substantially similar or identical to lower support 60 shown in FIG. 1 With the exception of passage 217 and nipple 218, the body 210 can be substantially similar or identical to the body 10 shown in FIG. 1. The upper support 270, septum cap 250, and cannula 230 can be substantially similar or identical to the corresponding features 70, 50 and 30 shown in FIG. 1.

Figure 15:
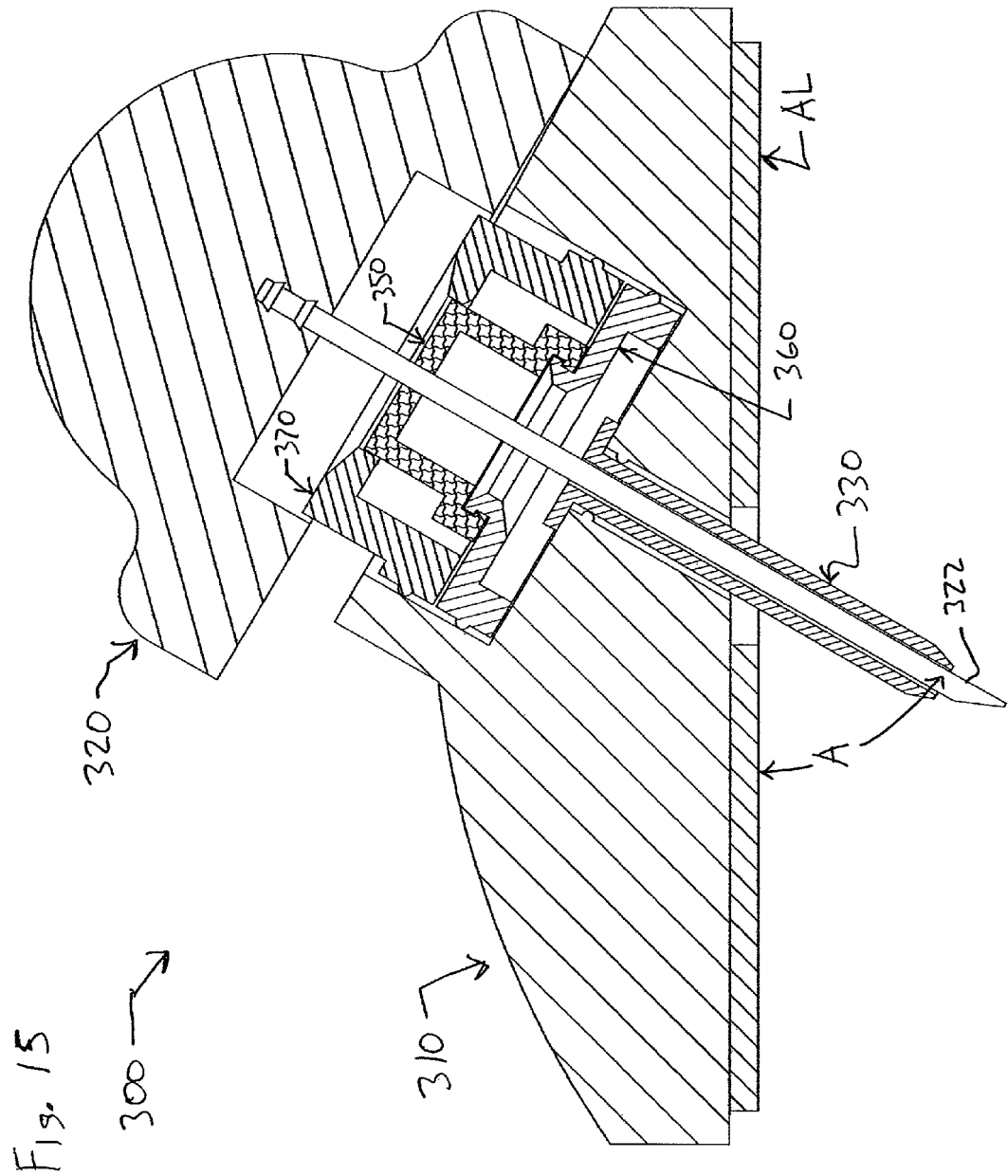
FIG. 15 shows a cross-section view of another non-limiting embodiment of the device. The insertion mechanism is shown in an installation position. This embodiment is similar to that of FIG. 1 except that the body, the cannula and the lower support are modified to allow the cannula to be oriented at an angle.
Figure 16:
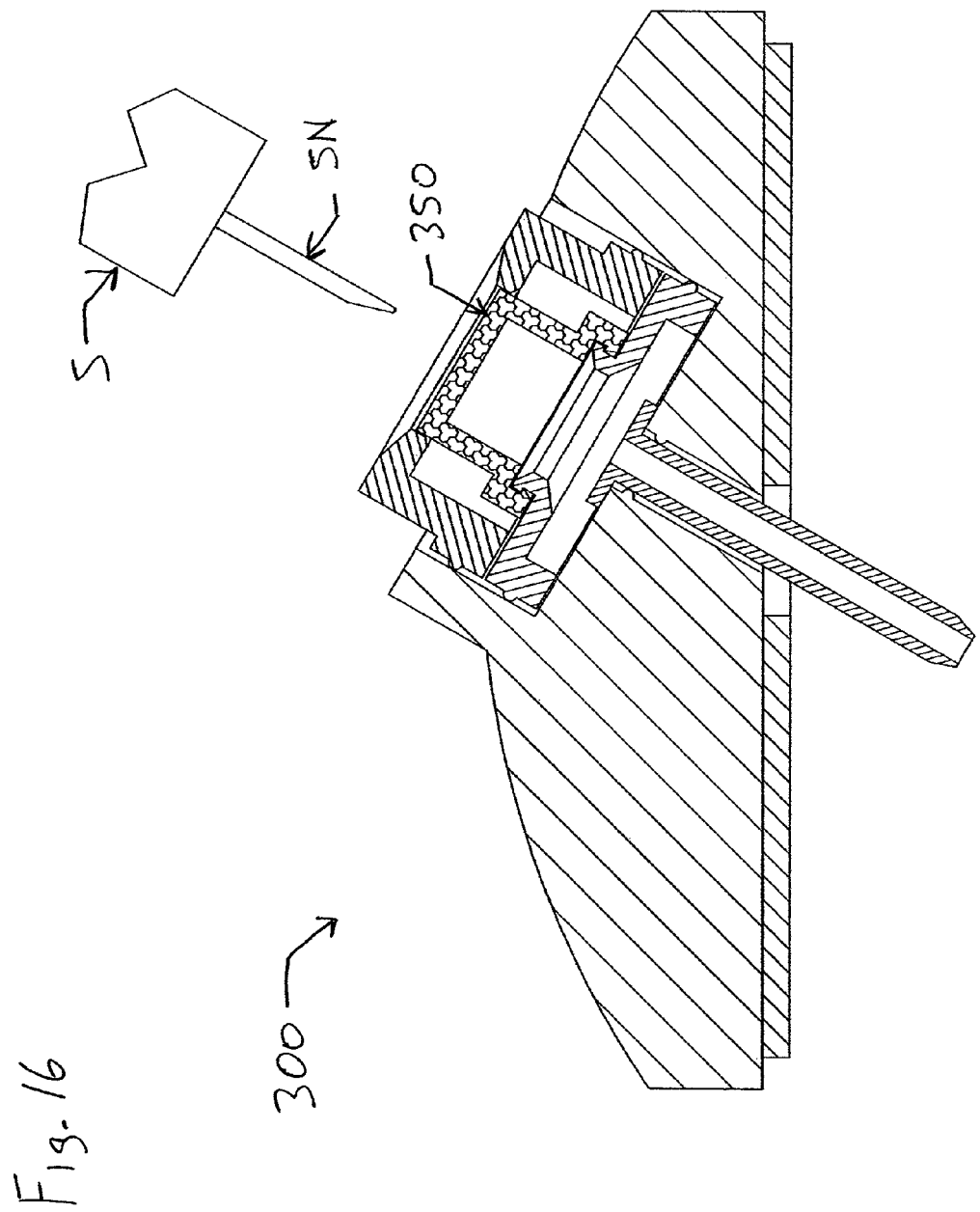
FIG. 16 shows the device of FIG. 15 in an installed configuration (the user's skin is not shown for clarity and the insertion mechanism is removed), and illustrates how a syringe can be used to inject fluid into the device along a side-angled direction, i.e., a direction that is not parallel to an imaginary line perpendicular to adhesive layer contact surface.

FIG. 15 shows another non-limiting embodiment of the device 300. This embodiment is similar to that of FIG. 1 except that the body 310, the cannula 330 and the lower support 360 are modified to allow the cannula 330 to be oriented at an angle "A". The angle A can be between about 15 degrees and about 75 degrees, and is preferably between about 45 degrees and about 60 degrees. FIG. 16 shows the device of FIG. 15 in an installed configuration (the user's skin is not shown for clarity and the insertion mechanism is removed), and illustrates how a syringe can be used to inject fluid into the device along a side-angled direction, i.e., a direction that is not parallel to an imaginary line perpendicular to adhesive layer contact surface. Unlike the device shown in FIG. 1, the device 300 shown in FIG. 15 is inserted into the skin of a user by moving the cannula 330 into the skin along a direction of angle A.

As can be seen in FIG. 15, fluid delivery device 300 includes a one-piece body 310. However, it may also be multi-piece body. Device 300 also includes removable insertion device 320 that has needle portion 322 that is inserted into body 310, and a needle guard (not shown) that is coupled to a bottom portion of the body 310. The needle guard may be coupled to the body 310 in any desired way such as, e.g., a friction fit, or any other suitable system of releasable attachment or engagement. Device 300 also includes a generically-depicted adhesive layer AL, which preferably includes a protective backing sheet or release layer (not shown). Adhesive layer AL may have the form of a circular pad having two opposing, adhesive-coated sides, one of which is attached to the relevant portion of the bottom surface of body 310 and the other of which will be attached to a user's body (e.g., once a backing sheet has been removed). Alternatively, one of the two opposing sides may be welded (e.g., ultrasonically welded) to the bottom surface of body 310 instead of being attached via an adhesive. As opposed to using an adhesive layer AL, a portion (e.g., all) of the bottom surface of body 310 may be configured to adhere directly to a living being's skin, such as by making the bottom surface material from a material that chemically reacts with and adheres to skin. Adhesive layer AL is one example of an adhesive portion (of a fluid delivery device) that is configured to adhere directly to a living being's skin. Device 300 also includes a cannula 330 which has one portion extending out past from the adhesive layer AL and another portion arranged within the body 310. Device 300 additionally includes a bottom support 360, a septum cap 350 coupled to the bottom support 360 and an upper support 370. The lower support 360 can have an upper portion that is substantially similar or identical to that of the lower support 60 shown in FIG. 1 The body 310 can be made of the same material as body 10 shown in FIG. 1. The upper support 270, septum cap 250, and cannula 230 can be substantially similar or identical to the corresponding features 70, 50 and 30 shown in FIG. 1, except that cannula 330 has a longer axial length than cannula 30 of FIG. 1.

Figure 17:
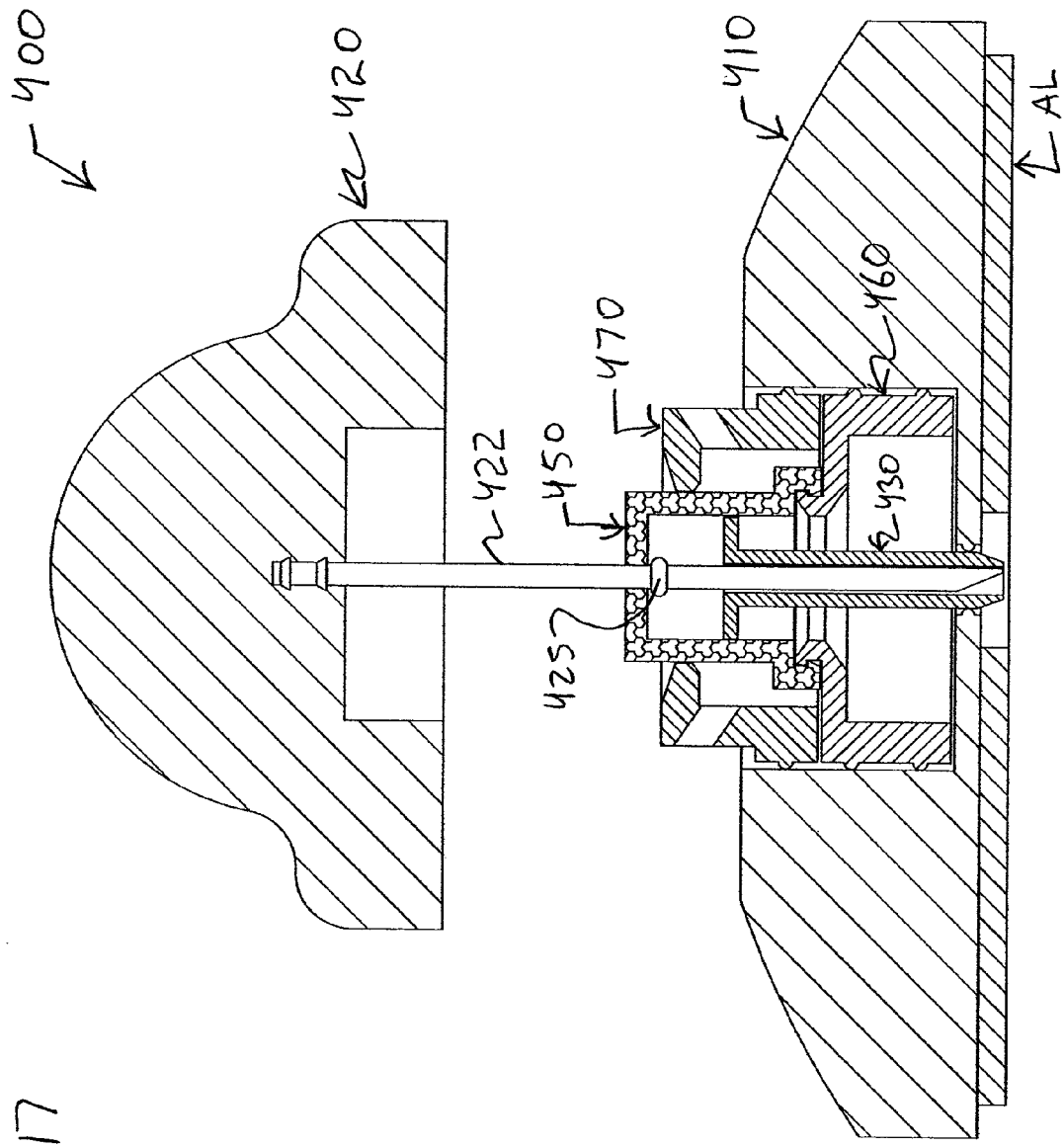
FIG. 17 shows a cross-section view of another non-limiting embodiment of the device. The insertion mechanism is shown in an initial position. This embodiment is similar to that of FIG. 1 except that the insertion mechanism, the septum cap and the cannula are modified to allow the cannula to be moved by the insertion mechanism from an initial retracted position to a puncturing position.
Figure 18:
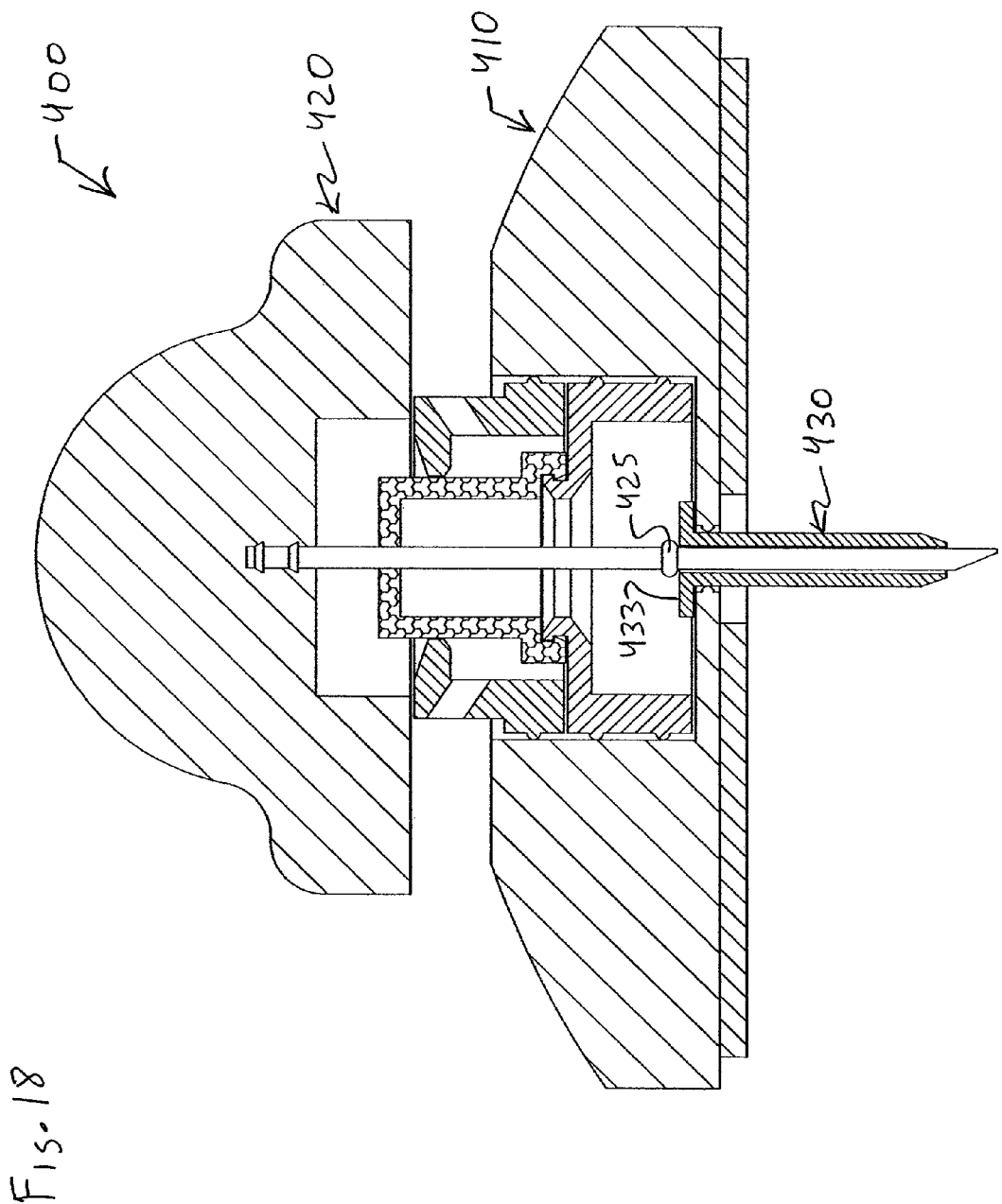
FIG. 18 shows the device of FIG. 17 after the insertion mechanism is moved towards the body and caused the cannula to move to the puncturing position.

FIGS. 17-19 show another non-limiting embodiment of the device 400. The insertion mechanism 420 is shown in an initial position. This embodiment is similar to that of FIG. 1 except that the insertion mechanism 420, the septum cap 450 and the cannula 430 are modified to allow the cannula 430 to be moved by the insertion mechanism 420 from an initial retracted position to a puncturing position. The insertion mechanism 420 can be moved towards the body 410 manually by the user. FIG. 18 shows the device 400 of FIG. 17 after the insertion mechanism 420 is moved towards the body 410 and caused the cannula 430 to move to the puncturing position. FIG. 19 shows the device 400 of FIG. 17 with the insertion mechanism 420 in a removed position.

As can be seen in FIG. 17, fluid delivery device 400 includes a one-piece body 410. However, it may also be multi-piece body. Device 400 also includes removable insertion device 420 that has needle portion 422 that is inserted into body 410. The needle portion 422 includes an integrally formed projection 425 which is sized to pass through the cap 450 without destroying the ability of the cap 450 to reseal the opening formed thereby and is also sized to engage or contact the cannula 430 in order to force the cannula 430 to move axially between the retracted position shown in FIG. 17 and the puncturing position shown in FIG. 18. A needle guard (not shown) is coupled to a bottom portion of the body 410. The needle guard may be coupled to the body 410 in any desired way such as, e.g., a friction fit, or any other suitable system of releasable attachment or engagement. Device 400 also includes a generically-depicted adhesive layer AL, which preferably includes a protective backing sheet or release layer (not shown). Adhesive layer AL may have the form of a circular pad having two opposing, adhesive-coated sides, one of which is attached to the relevant portion of the bottom surface of body 410 and the other of which will be attached to a user's body (e.g., once a backing sheet has been removed). Alternatively, one of the two opposing sides may be welded (e.g., ultrasonically welded) to the bottom surface of body 410 instead of being attached via an adhesive. As opposed to using an adhesive layer AL, a portion (e.g., all) of the bottom surface of body 410 may be configured to adhere directly to a living being's skin, such as by making the bottom surface material from a material that chemically reacts with and adheres to skin. Adhesive layer AL is one example of an adhesive portion (of a fluid delivery device) that is configured to adhere directly to a living being's skin. Device 400 also includes a cannula 430 which has one portion extending out past from the adhesive layer AL and another portion arranged within the body 410. Device 400 additionally includes a bottom support 460, a septum cap 450 coupled to the bottom support 460 and an upper support 470. The lower support 460, body 410, and upper support 470 can be substantially similar or identical to the corresponding members 60, 10 and 70 shown in FIG. 1. The septum cap 450 and cannula 430 can be substantially similar to the cap 50 and cannula 30 shown in FIG. 1, except that they can utilize a longer axial length.

Figure 20:
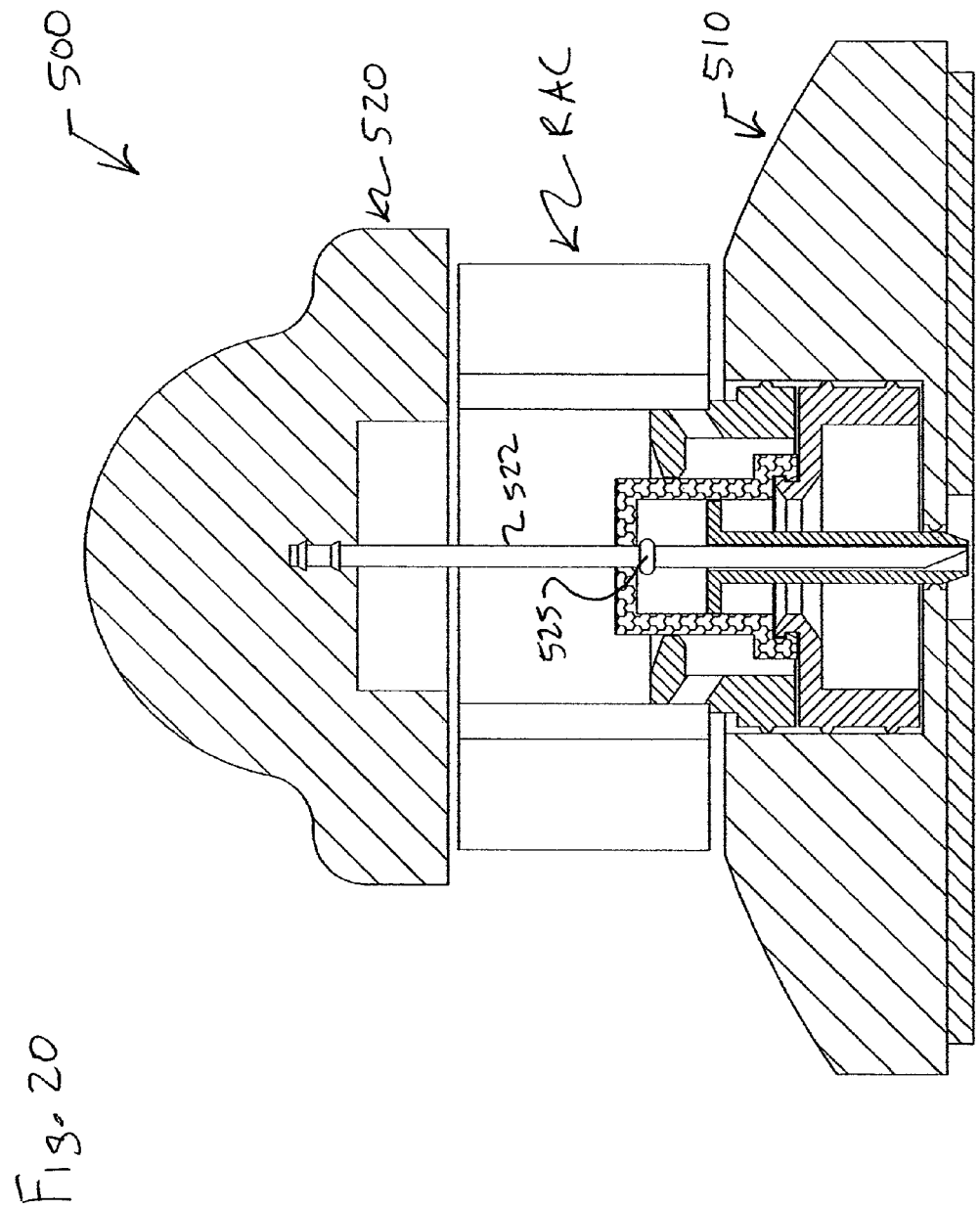
FIG. 20 shows a cross-section view of another non-limiting embodiment of the device. This embodiment is similar to that of FIG. 17 except that it utilizes a removable activation clip to ensure that the insertion mechanism is not accidentally caused to move and thereby cause the cannula to be moved by the insertion mechanism from an initial retracted position to a puncturing position.
Figure 21:
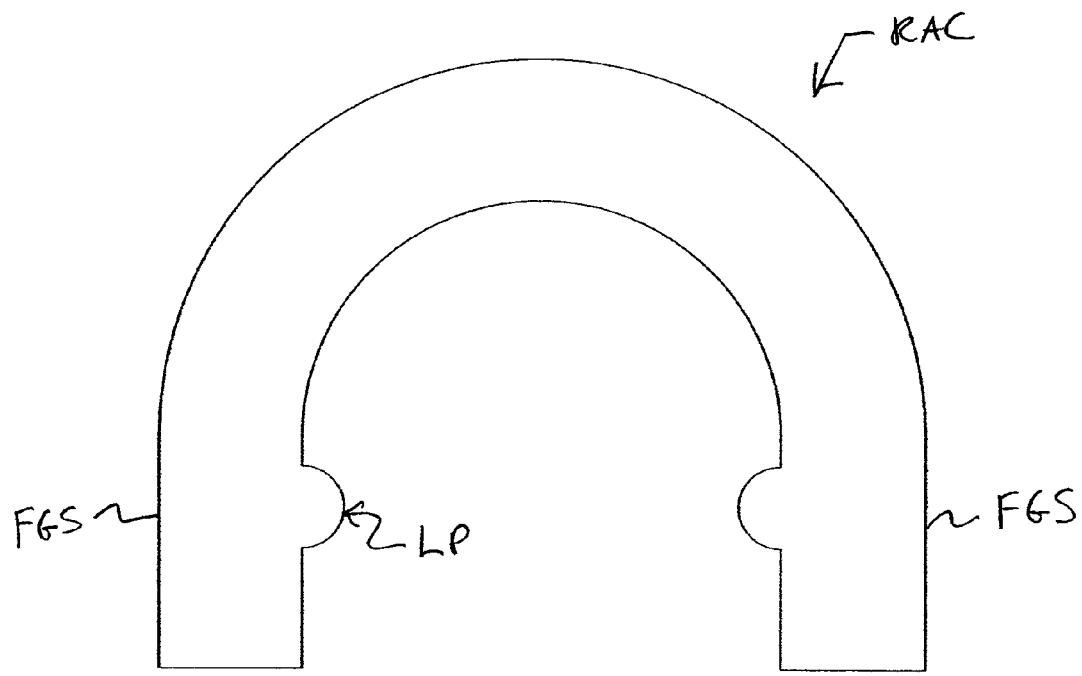
FIG. 21 shows a top view of the removable activation clip used in the embodiment shown in FIG. 20.
Figure 22:
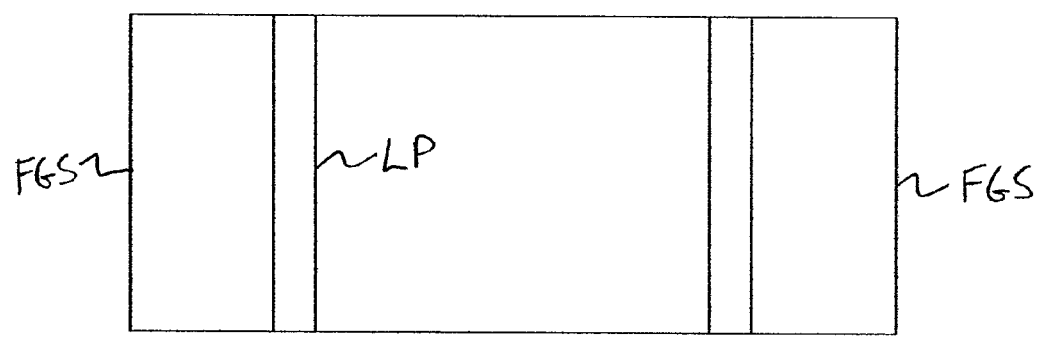
FIG. 22 shows a front view of the removable activation clip shown in FIG. 21.

FIGS. 20-22 show another non-limiting embodiment of the device 500. This embodiment is similar to that of FIG. 17 except that it utilizes a removable activation clip RAC to ensure that the insertion mechanism 520 is not accidentally caused to move and thereby cause the cannula 530 to be moved by the insertion mechanism 520 from an initial retracted position to a puncturing position. The clip RAC is generally U-shaped and is configured to deflect when installed or removed. Preferably, the clip RAC is made of an inexpensive synthetic resin material and can be discarded after being removed.

As can be seen in FIG. 20, fluid delivery device 500 includes a one-piece body 510. However, it may also be multi-piece body. Device 500 also includes removable insertion device 520 that has needle portion 522 that is inserted into body 510. The needle portion 522 includes an integrally formed projection 525 which is sized to pass through the cap 550 without destroying the ability of the cap 550 to reseal the opening formed thereby and is also sized to engage or contact the cannula 530 in order to force the cannula 530 to move axially between the retracted position shown in FIG. 20 and a puncturing position similar to that shown in FIG. 18 (after the clip RAC is removed). A needle guard (not shown) is coupled to a bottom portion of the body 510. The needle guard may be coupled to the body 510 in any desired way such as, e.g., a friction fit, or any other suitable system of releasable attachment or engagement. Device 500 also includes a generically-depicted adhesive layer AL, which preferably includes a protective backing sheet or release layer (not shown). Adhesive layer AL may have the form of a circular pad having two opposing, adhesive-coated sides, one of which is attached to the relevant portion of the bottom surface of body 510 and the other of which will be attached to a user's body (e.g., once a backing sheet has been removed). Alternatively, one of the two opposing sides may be welded (e.g., ultrasonically welded) to the bottom surface of body 510 instead of being attached via an adhesive. As opposed to using an adhesive layer AL, a portion (e.g., all) of the bottom surface of body 510 may be configured to adhere directly to a living being's skin, such as by making the bottom surface material from a material that chemically reacts with and adheres to skin. Adhesive layer AL is one example of an adhesive portion (of a fluid delivery device) that is configured to adhere directly to a living being's skin. Device 500 also includes a cannula 530 which has one portion extending out past from the adhesive layer AL and another portion arranged within the body 510. Device 500 additionally includes a bottom support 560, a septum cap 550 coupled to the bottom support 560 and an upper support 570. The lower support 560, body 510, and upper support 570 can be substantially similar or identical to the corresponding members 60, 10 and 70 shown in FIG. 1. The septum cap 550 and cannula 530 can be substantially similar to the cap 50 and cannula 30 shown in FIG. 1, except that they can utilize a longer axial length.

Figure 23:
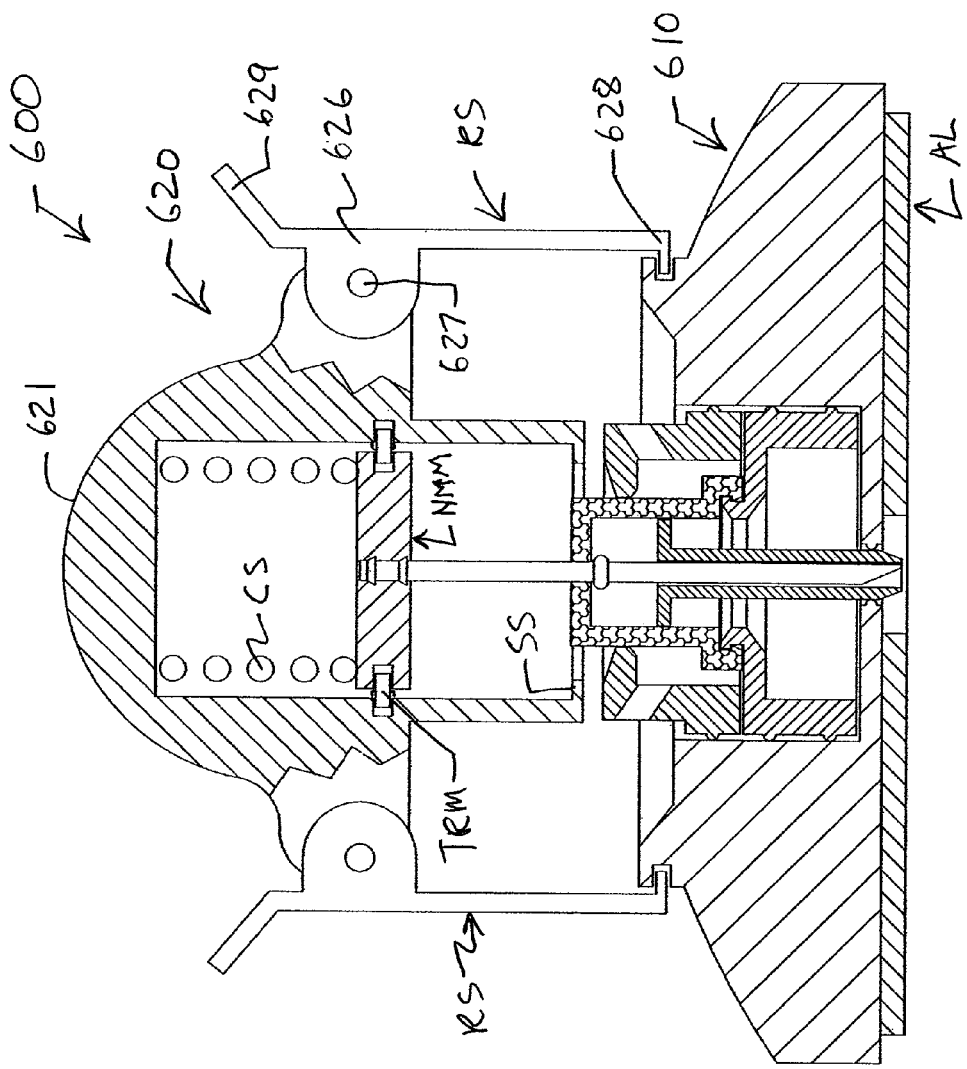
FIG. 23 shows a cross-section view of another non-limiting embodiment of the device. This embodiment is similar to that of FIG. 17 except that the insertion mechanism is modified to include a system for automatically causing the cannula to be moved from an initial retracted position to a puncturing position. The insertion mechanism also utilizes an arrangement of removable supports which engage with recesses in the body.
Figure 24:
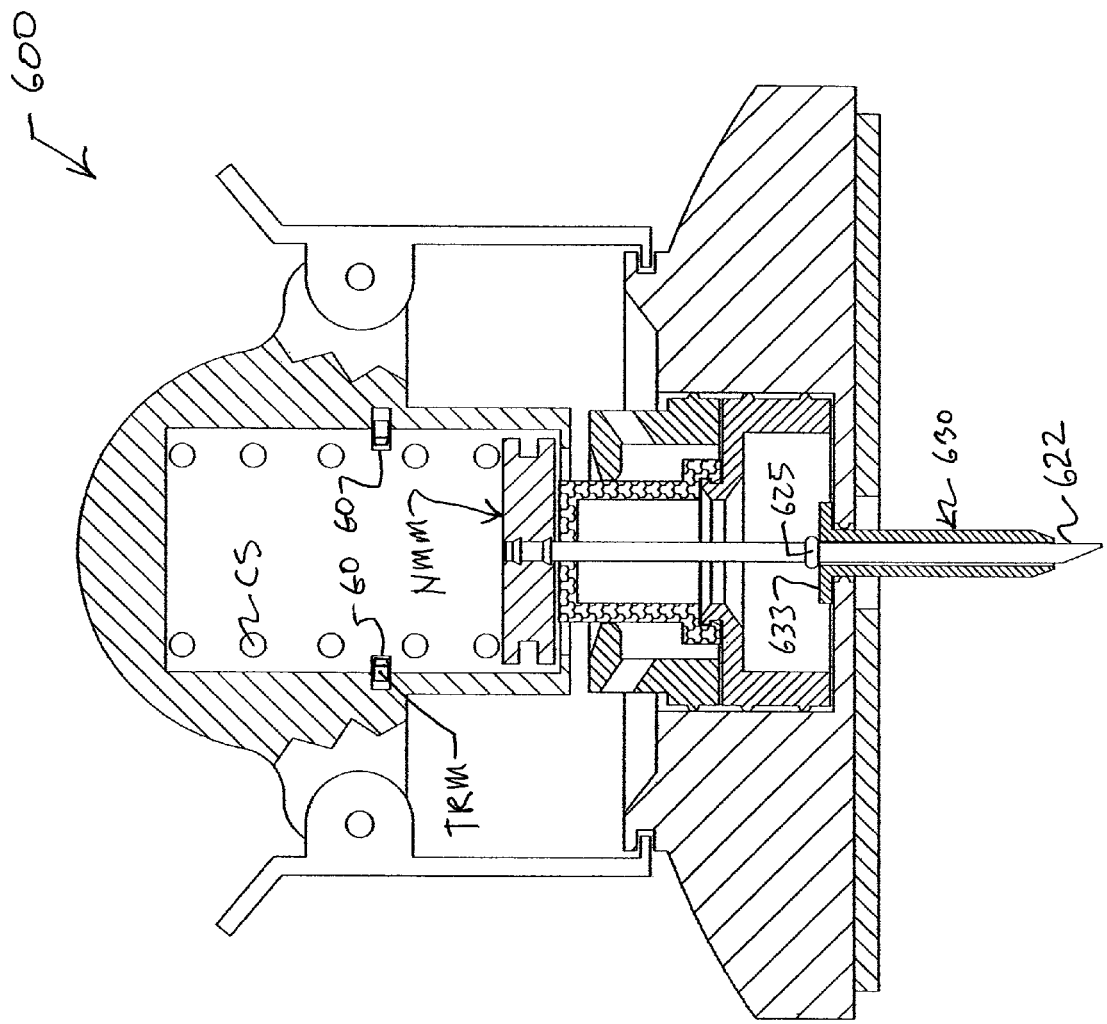
FIG. 24 shows the device of FIG. 23 after the insertion mechanism is moved towards the body and caused the cannula to move to the puncturing position.
Figure 26:
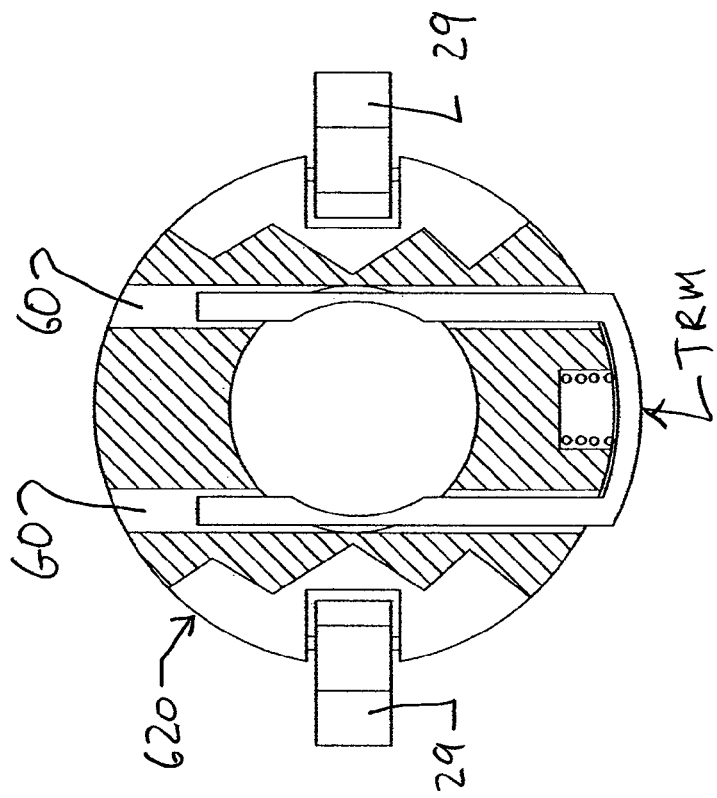
FIGS. 25 and 26 show partial cross-section views of the insertion mechanism used in the embodiment shown in FIG. 23 with FIG. 25 showing a trigger release mechanism in an initial position and with FIG. 26 showing the trigger release mechanism in a triggering position.
Figure 25:
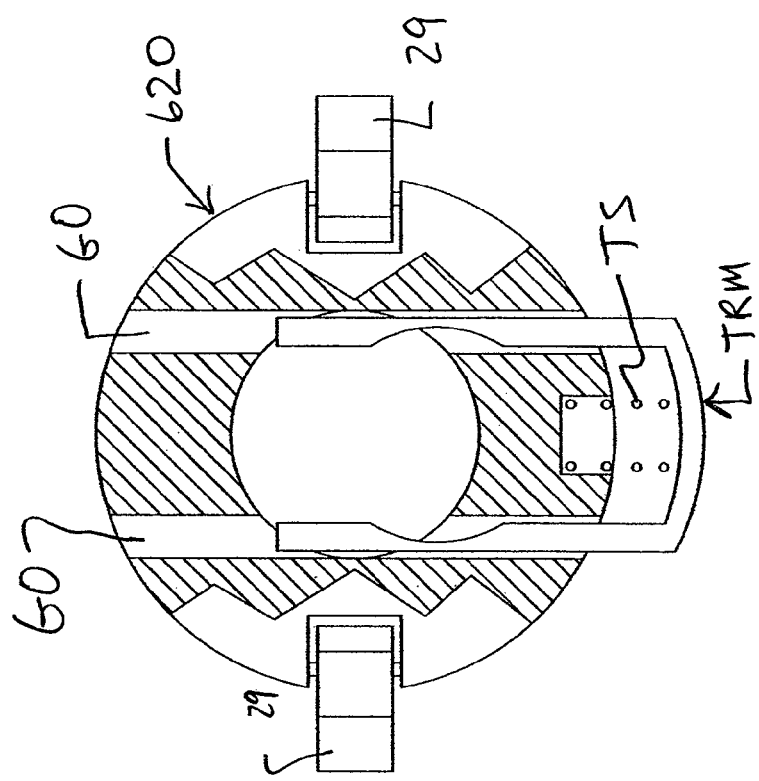
Figure 28:
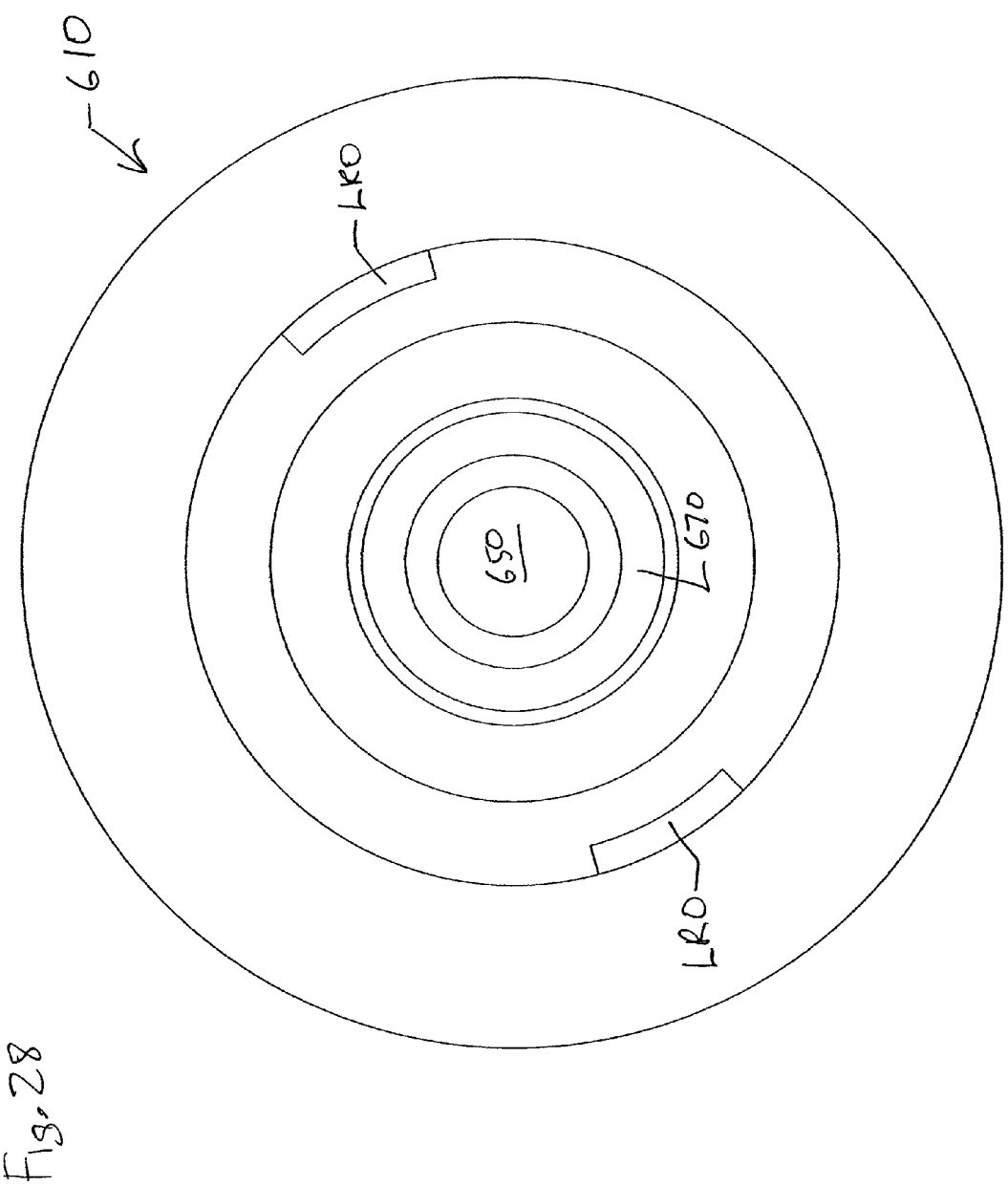
FIG. 28 shows a top view of the body assembly portion of the device of FIG. 23, i.e., the device with the insertion mechanism removed.
Figure 29:
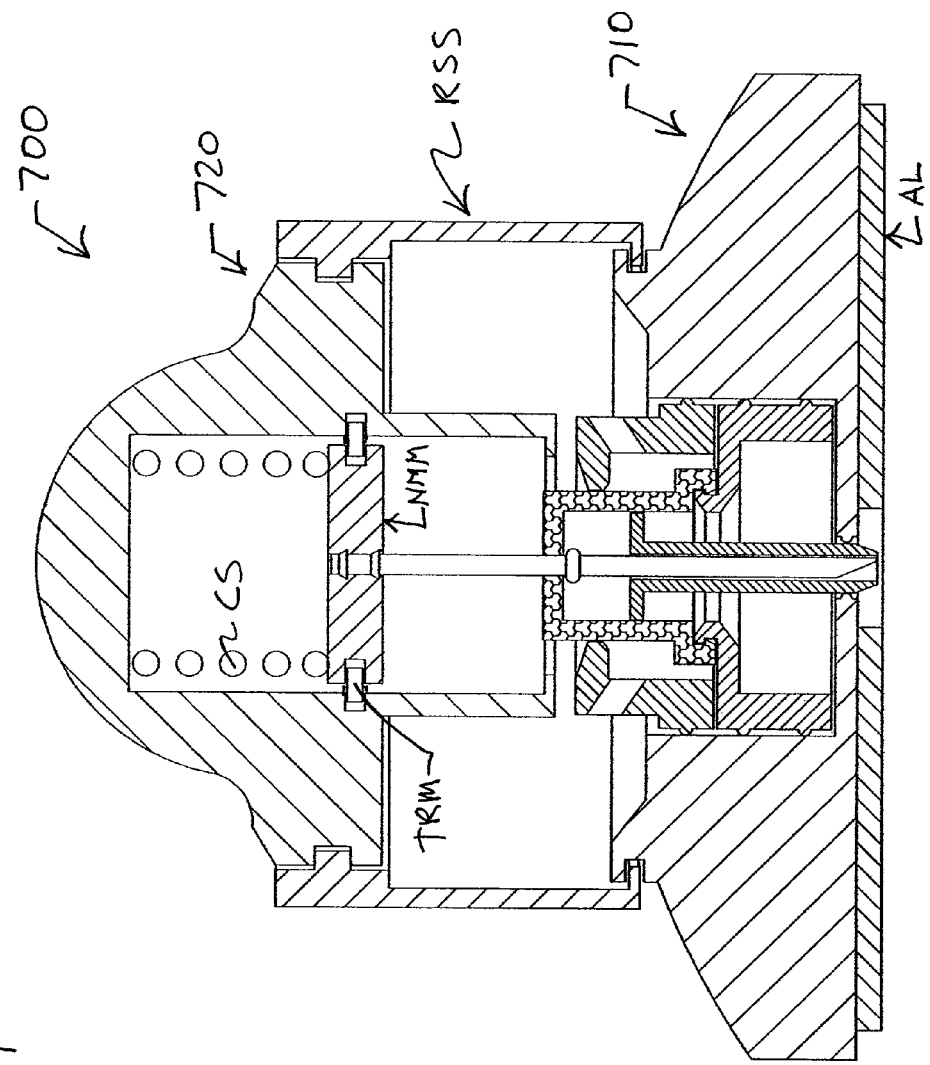
FIG. 29 shows a cross-section view of another non-limiting embodiment of the device. This embodiment is similar to that of FIG. 23 except that the arrangement of removable supports which engage with recesses in the body is replaced with a removable support sleeve that engages with recesses in the body.
Figure 30:
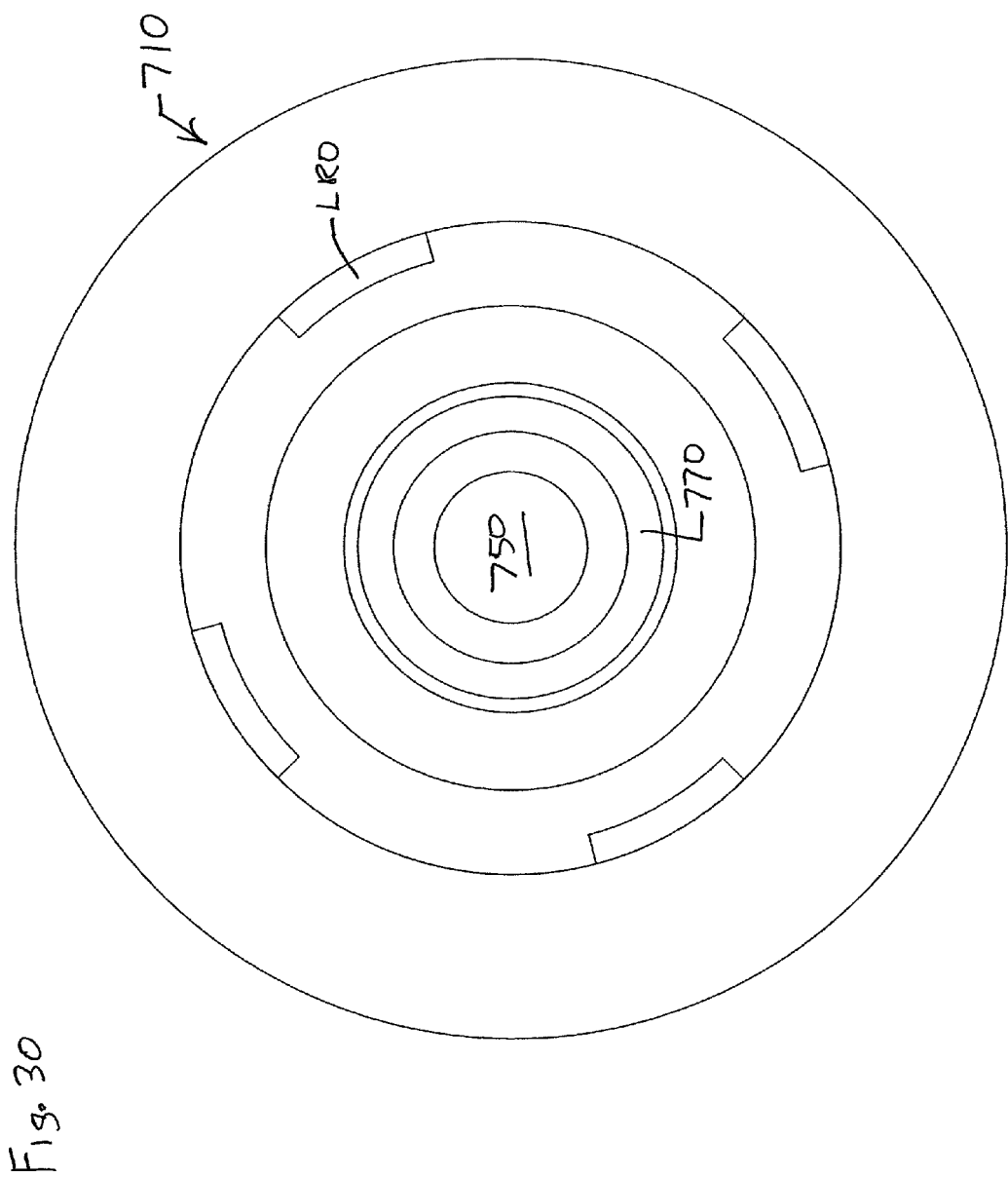
FIG. 30 shows a top view of the body assembly portion of the device of FIG. 29, i.e., the device with the insertion mechanism removed.

FIGS. 23-28 show another non-limiting embodiment of the device 600. This embodiment is similar to that of FIG. 17 except that the insertion mechanism 620 is modified to include a system for automatically causing the cannula 630 to be moved from an initial retracted position (FIG. 23) to a puncturing position (FIG. 24). The insertion mechanism 620 also utilizes an arrangement of removable supports RS which engage with recesses LR in the body 610. FIG. 24 shows the device 600 after the insertion mechanism 620 is activated and caused the cannula 630 to move to the puncturing position. FIGS. 25 and 26 show partial cross-section views of the insertion mechanism 620 with FIG. 25 showing a trigger release mechanism TRM in an initial position and with FIG. 26 showing the trigger release mechanism TRM in a triggering position. FIG. 27 shows the device 600 with the insertion mechanism 620 in a removed position. FIG. 28 shows a top view of the body assembly portion of the device 600.

As can be seen in FIG. 23, fluid delivery device 600 includes a one-piece body 610. However, it may also be multi-piece body. Device 600 also includes removable insertion device 620 that has needle portion 622 that is inserted into body 610. The needle portion 622 includes an integrally formed projection 625 which is sized to pass through the cap 650 without destroying the ability of the cap 650 to reseal the opening formed thereby and is also sized to engage or contact the cannula 630 in order to force the cannula 630 to move axially between the retracted position shown in FIG. 23 and a puncturing position shown in FIG. 24 (after the system TRM is triggered). This occurs when the triggering system TRM, which slides within guide openings GO, is moved from the position shown in FIG. 25 to that of FIG. 26 and because of the biasing force of a metal compression spring CS, which applies a biasing force to the disk-shaped need moving member NMM coupled to the needle 622. A second smaller compression TS is utilized to bias the member TRM towards the trigger-set position shown in FIG. 25. A needle guard (not shown) is coupled to a bottom portion of the body 610. The needle guard may be coupled to the body 610 in any desired way such as, e.g., a friction fit, or any other suitable system of releasable attachment or engagement. Device 600 also includes a generically-depicted adhesive layer AL, which preferably includes a protective backing sheet or release layer (not shown). Adhesive layer AL may have the form of a circular pad having two opposing, adhesive-coated sides, one of which is attached to the relevant portion of the bottom surface of body 610 and the other of which will be attached to a user's body (e.g., once a backing sheet has been removed). Alternatively, one of the two opposing sides may be welded (e.g., ultrasonically welded) to the bottom surface of body 610 instead of being attached via an adhesive. As opposed to using an adhesive layer AL, a portion (e.g., all) of the bottom surface of body 610 may be configured to adhere directly to a living being's skin, such as by making the bottom surface material from a material that chemically reacts with and adheres to skin. Adhesive layer AL is one example of an adhesive portion (of a fluid delivery device) that is configured to adhere directly to a living being's skin. Device 600 also includes a cannula 630 which has one portion extending out past from the adhesive layer AL and another portion arranged within the body 610. Device 600 additionally includes a bottom support 660, a septum cap 650 coupled to the bottom support 660 and an upper support 670. The lower support 660, body 610, and upper support 670 can be substantially similar or identical to the corresponding members 60, 10 and 70 shown in FIG. 1, except that the body includes recesses LR which are configured to lockingly engage with portions 628 of the supports RS when, e.g., portions 628 are lowered into recesses LR and the member 620 is rotated about 30 degrees to a locking position. The septum cap 650 and cannula 630 can be substantially similar to the cap 50 and cannula 30 shown in FIG. 1, except that they can utilize a longer axial length. Although the members RS have sections 626 which are pivotally mounted via pivot members 627 and deflectable by a user gripping ends 629, the member 620 can also utilize a living hinge between members RS and the gripping portion of member 620.

FIGS. 29-32 show another non-limiting embodiment of the device 700. This embodiment is similar to that of FIG. 23 except that the arrangement of removable supports RS which engage with recesses LR in the body is replaced with a member 720 having a removable support sleeve RSS that includes locking projections LP that engage with recesses LRO in the body 710.

Figure 33:
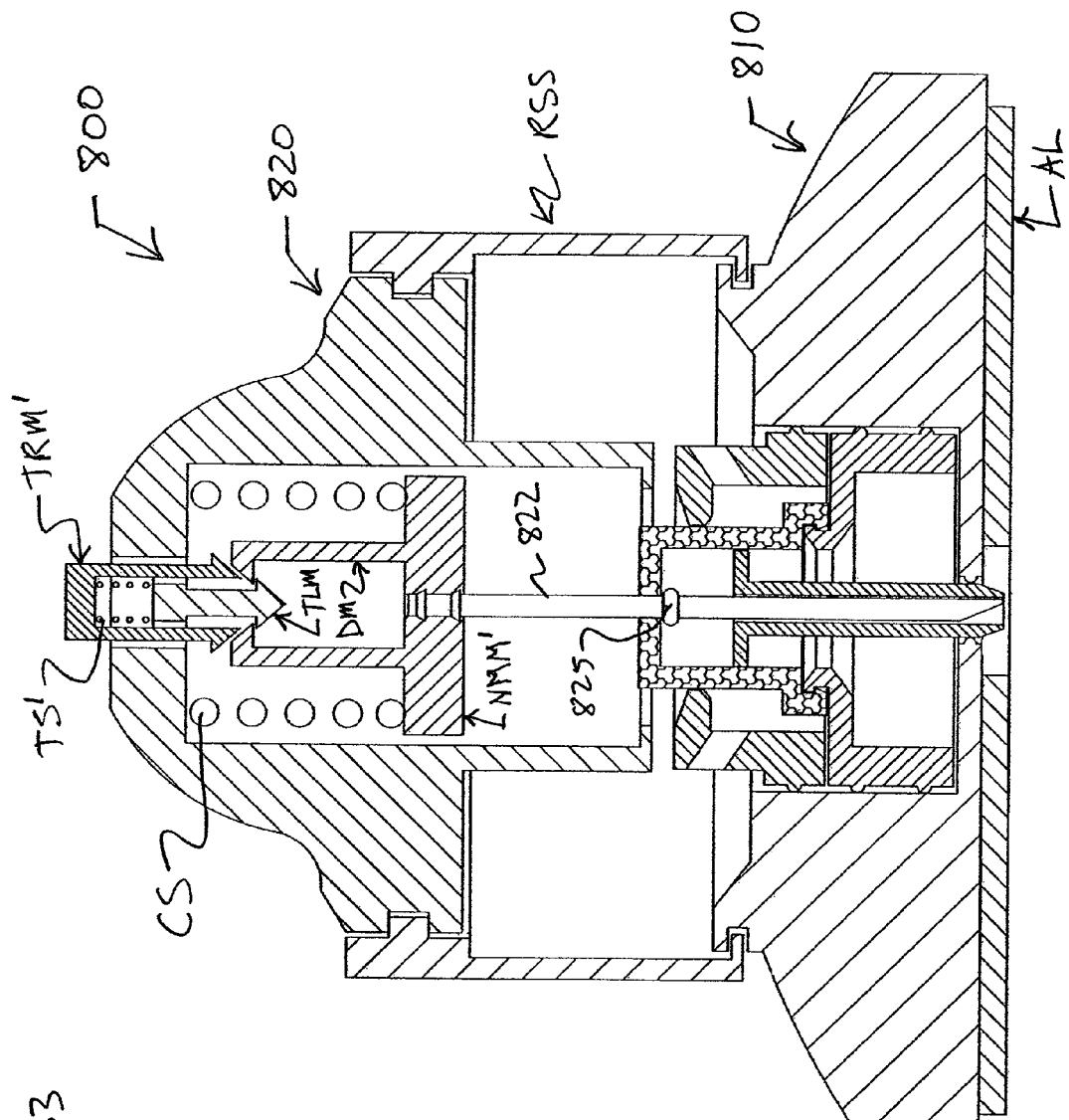
FIG. 33 shows a cross-section view of another non-limiting embodiment of the device. This embodiment is similar to that of FIG. 29 except that the trigger release mechanism of FIGS. 25 and 26 is replaced with another type of triggering system.
Figure 34:
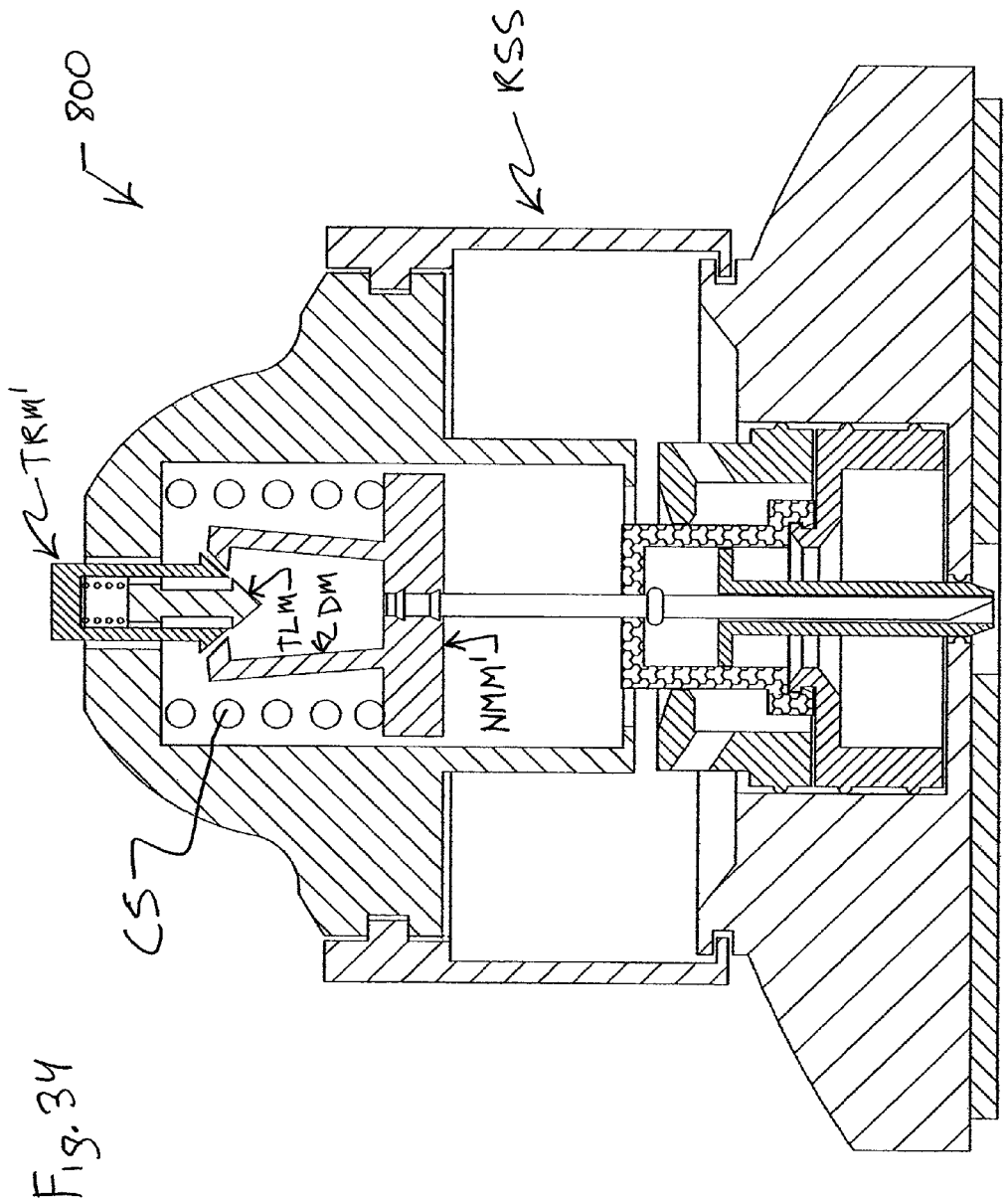
FIG. 34 shows the device of FIG. 33 after the triggering system is activated and before the spring causes the insertion needle to move towards the body and cause the cannula to move to the puncturing position.
Figure 35:
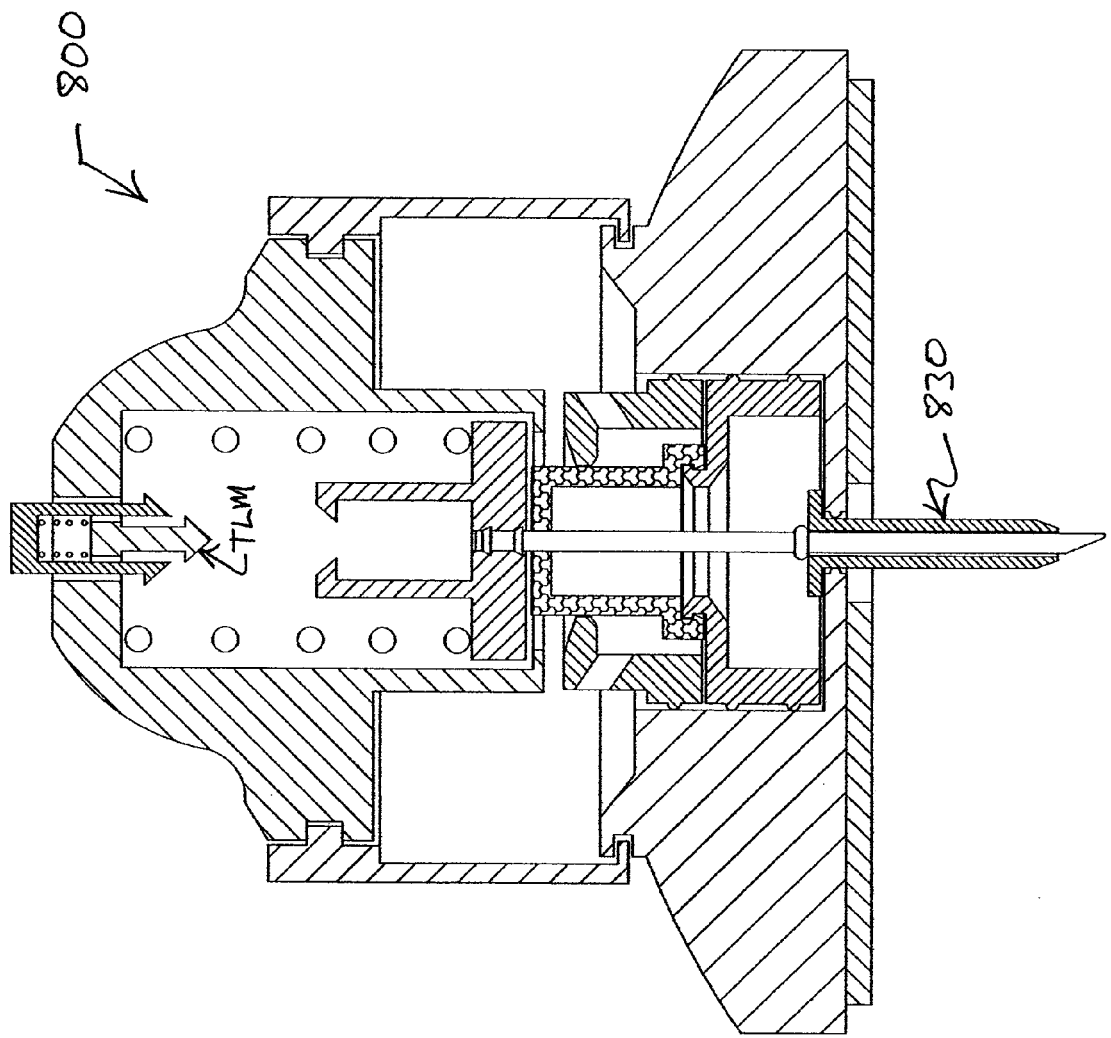
FIG. 35 shows the device of FIG. 33 after the triggering system is activated and after the spring causes the insertion needle to move towards the body and causes the cannula to move to the puncturing position.
Figure 36:
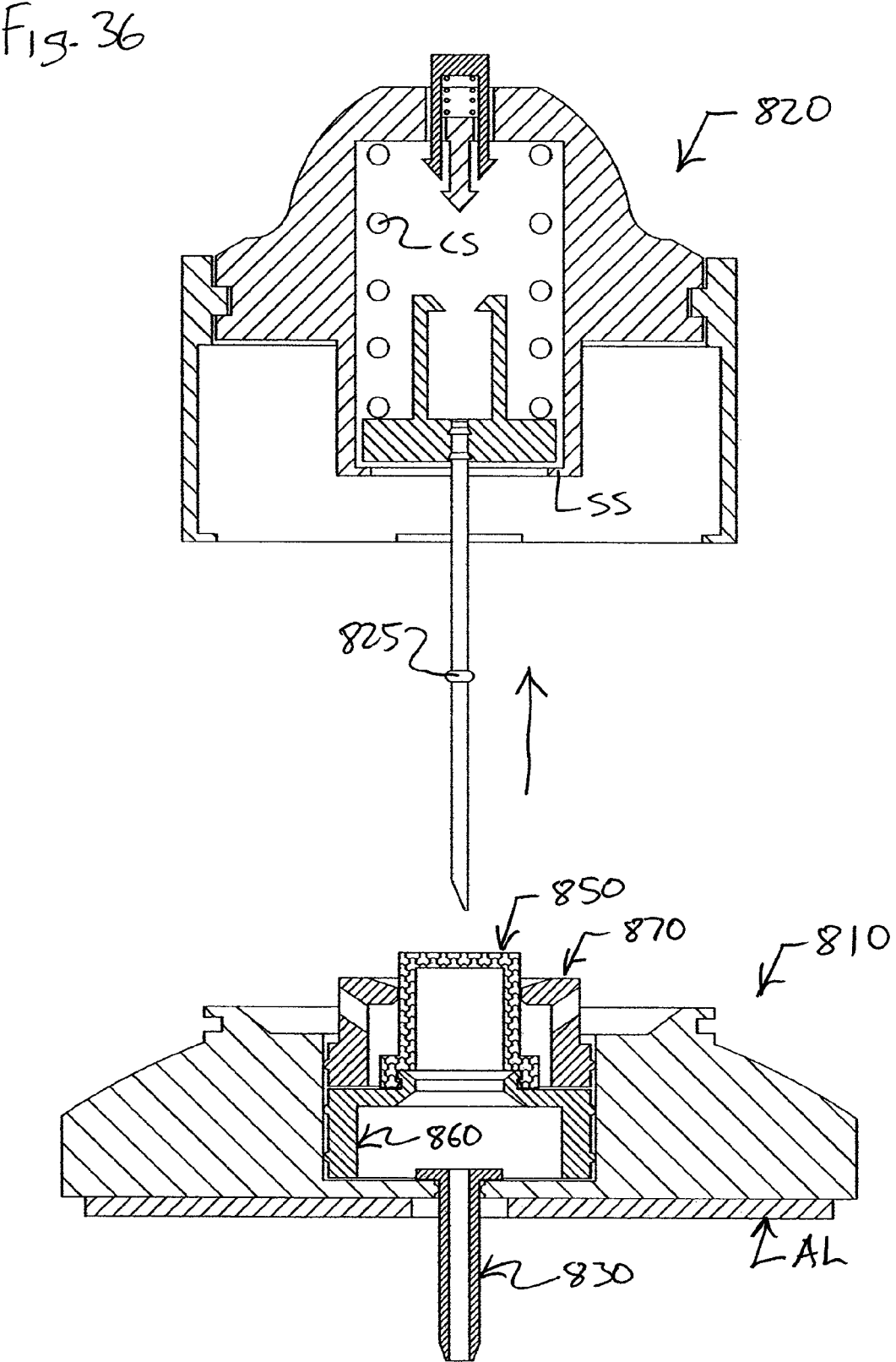
FIG. 36 shows the device of FIG. 33 with the insertion mechanism in a removed position.
Figure 38:
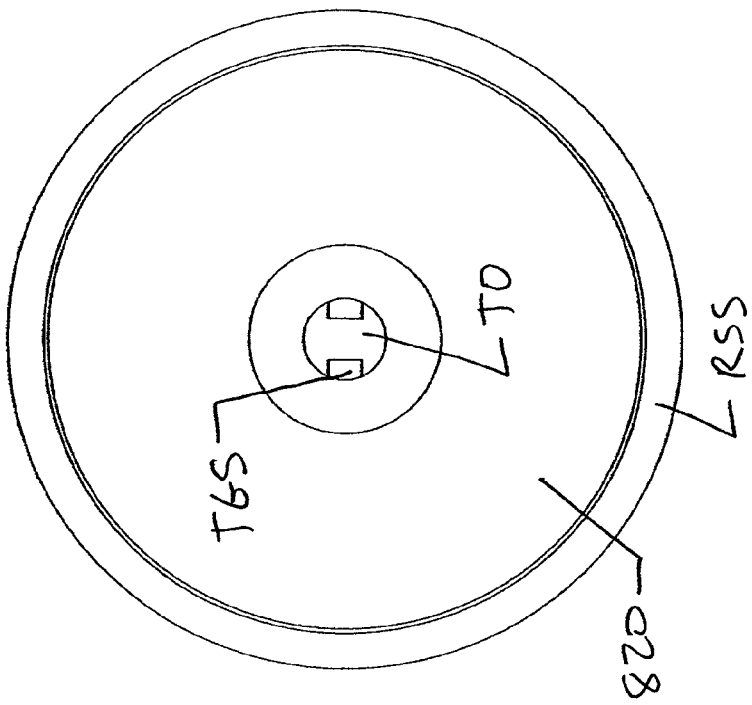
FIG. 38 shows a top view of the insertion mechanism shown in FIG. 37 with the push-button and trigger spring removed.
Figure 37:
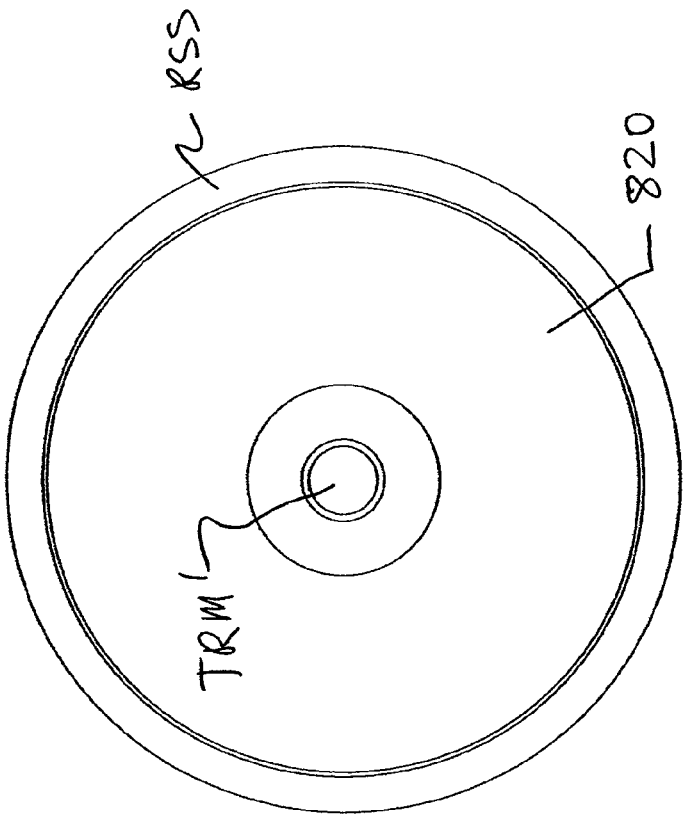
FIG. 37 shows a top view of the insertion mechanism shown in FIG. 33.
Figure 39:
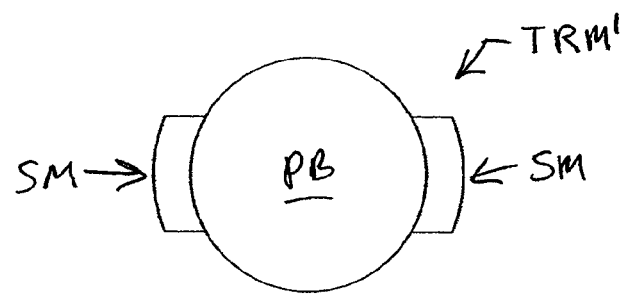
FIG. 39 shows a top view of the push-button shown in FIG. 40.
Figure 40:
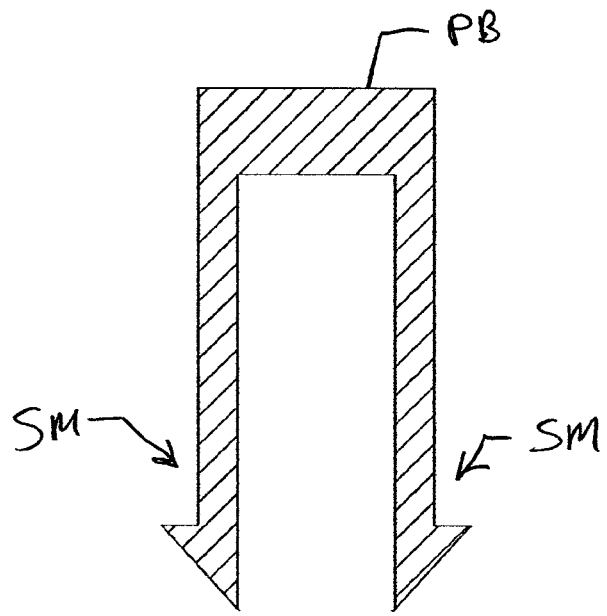
FIG. 40 shows a side cross-section view of the push-button used in the embodiment of FIG. 33.
Figure 41:
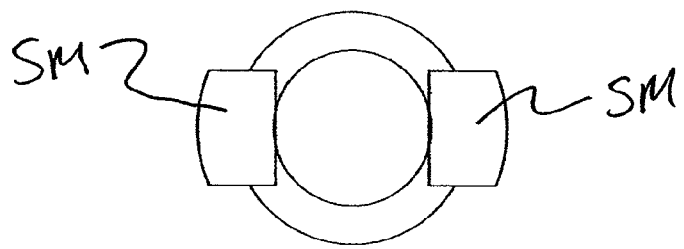
FIG. 41 shows a bottom view of the push-button shown in FIG. 40.
Figure 42:
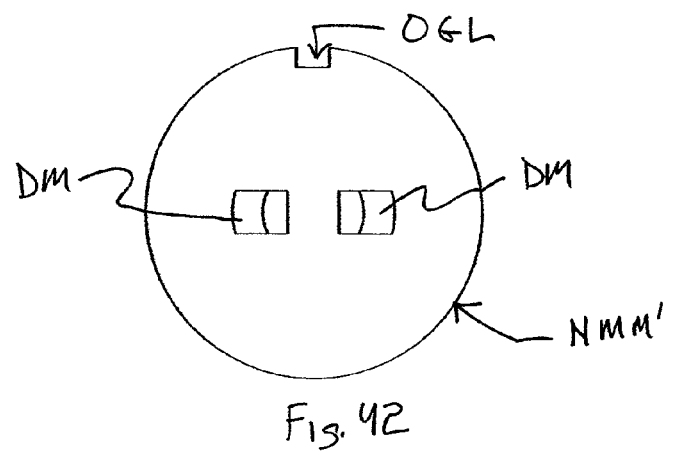
FIG. 42 shows a top view of the insertion needle assembly shown in FIG. 43.
Figure 43:
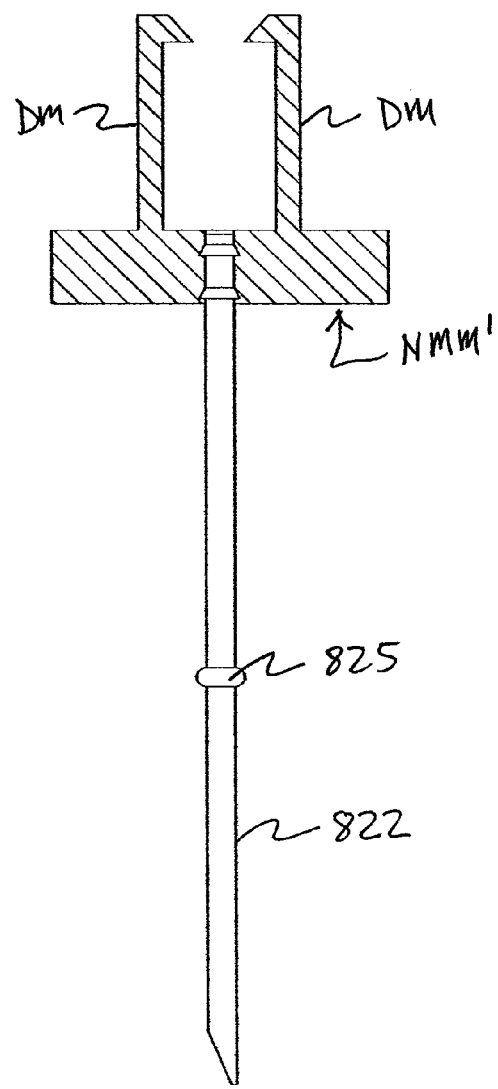
FIG. 43 shows a side cross-section view of the insertion needle assembly used in the embodiment of FIG. 33.

FIGS. 33-43 show another non-limiting embodiment of the device 800. This embodiment is similar to that of FIG. 29 except that the trigger release mechanism of FIGS. 25 and 26 is replaced with a triggering system TRM'. FIG. 33 shows the triggering system TRM' in an initial un-triggered position and FIG. 34 shows the device 800 after the triggering system TRM' is activated and before the spring CS causes the insertion needle 822 to move towards the body 810 and cause the cannula 830 to move to the puncturing position (see FIG. 35). FIG. 35 shows the device 800 after the triggering system TRM' is activated and after the spring CS causes the insertion needle 822 to move towards the body 810 and causes the cannula 830 to move to the puncturing position. FIG. 36 shows the device 800 with the insertion mechanism 820 in a removed position. FIG. 37 shows a top view of the insertion mechanism 820 and FIG. 38 shows a top view of the insertion mechanism shown in FIG. 37 with the push-button PB and trigger spring TS' removed. FIG. 39 shows a top view of the push-button PB, FIG. 40 shows a side cross-section view of the push-button PB and FIG. 41 shows a bottom view of the push-button PB. FIG. 42 shows a top view of the insertion needle assembly shown in FIG. 43 and FIG. 43 shows a side cross-section view of the insertion needle assembly used in the embodiment of FIG. 33.

As can be seen in FIG. 33, fluid delivery device 800 includes a one-piece body 810. However, it may also be multi-piece body. Device 800 also includes removable insertion device 820 that has needle portion 822 that is inserted into body 810. The needle portion 822 includes an integrally formed projection 825 which is sized to pass through the cap 850 without destroying the ability of the cap 850 to reseal the opening formed thereby and is also sized to engage or contact the cannula 830 in order to force the cannula 830 to move axially between the retracted position shown in FIG. 33 and a puncturing position shown in FIG. 35 (after the system TRM' is triggered). This occurs when the triggering system TRM', whose push-button PB slides within openings TO and TGS (see FIG. 38), is moved from the position shown in FIG. 33, to the position shown in FIG. 34 and finally to the position shown in FIG. 35, and because of the biasing force of a metal compression spring CS, which applies a biasing force to the disk-shaped need moving member NMM' coupled to the needle 822. A stop shoulder SS (see FIG. 36) limits downward movement of the needle moving member NMM'. A second smaller compression TS' is utilized to bias the member TRM' towards the trigger-set position shown in FIG. 33. As is apparent from FIG. 34, when the tapered ends of members SM engage the tapered ends of deflectable members DM (see also FIG. 43), the needle moving member NMM' automatically releases from the trigger lock member TLM under the action of the spring CS. A needle guard (not shown) is coupled to a bottom portion of the body 810. The needle guard may be coupled to the body 810 in any desired way such as, e.g., a friction fit, or any other suitable system of releasable attachment or engagement. Device 800 also includes a generically-depicted adhesive layer AL, which preferably includes a protective backing sheet or release layer (not shown). Adhesive layer AL may have the form of a circular pad having two opposing, adhesive-coated sides, one of which is attached to the relevant portion of the bottom surface of body 810 and the other of which will be attached to a user's body (e.g., once a backing sheet has been removed). Alternatively, one of the two opposing sides may be welded (e.g., ultrasonically welded) to the bottom surface of body 810 instead of being attached via an adhesive. As opposed to using an adhesive layer AL, a portion (e.g., all) of the bottom surface of body 810 may be configured to adhere directly to a living being's skin, such as by making the bottom surface material from a material that chemically reacts with and adheres to skin. Adhesive layer AL is one example of an adhesive portion (of a fluid delivery device) that is configured to adhere directly to a living being's skin. Device 800 also includes a cannula 830 which has one portion extending out past from the adhesive layer AL and another portion arranged within the body 810. In each of the herein disclosed embodiments, it is also possible to dispense with the layer AL altogether and instead apply a temporary and/or safe and washable/removable adhesive substance (e.g., a spray-on coating) to a user's skin and then mount the device to the skin. As in previous embodiments, the device 800 preferably utilizes a bottom support 860, a septum cap 850 coupled to the bottom support 860 and an upper support 870.

Figure 44:
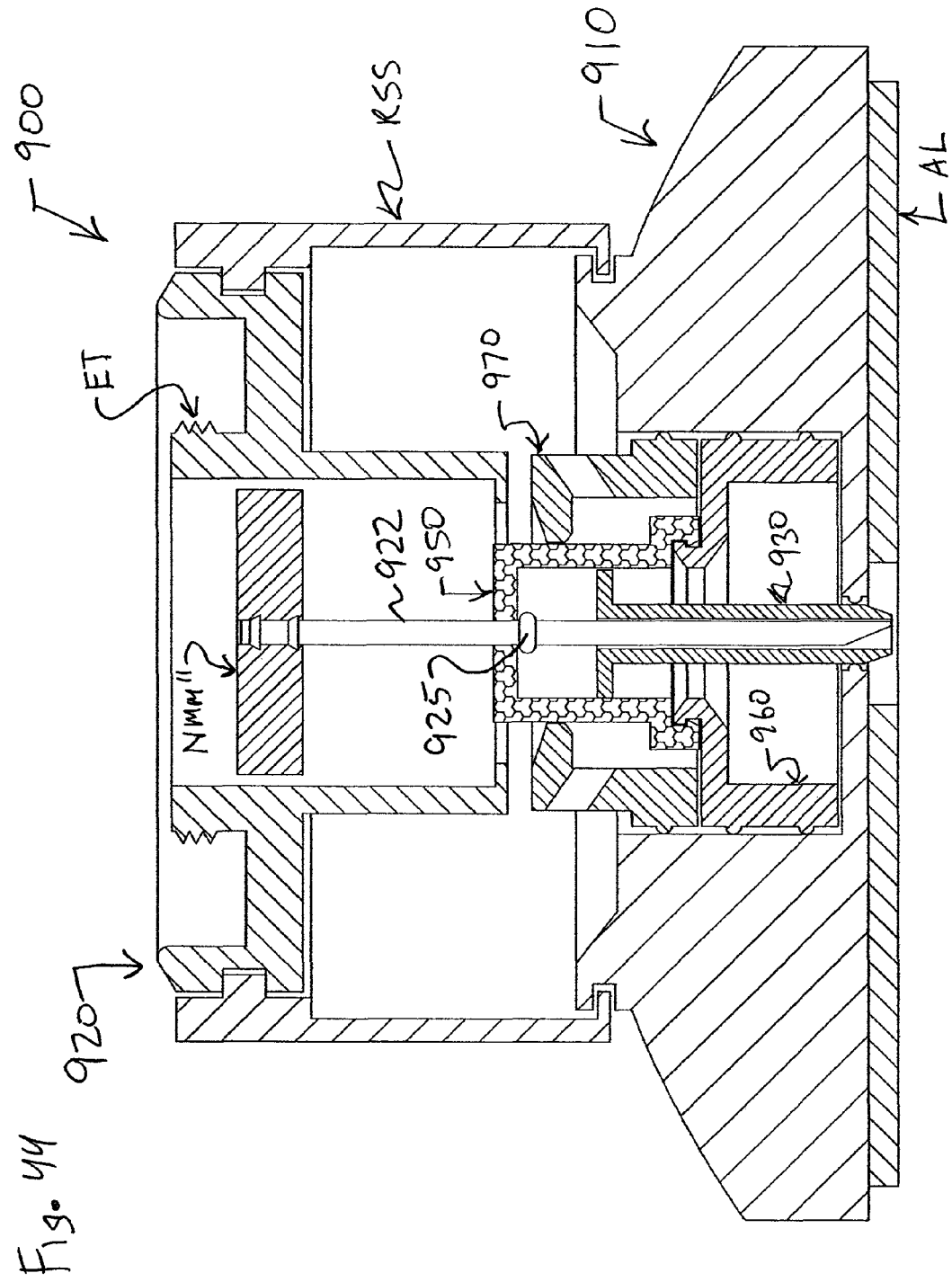
FIG. 44 shows a cross-section view of another non-limiting embodiment of the device. This embodiment is similar to that of FIG. 29 except that no trigger release mechanism is utilized on the device and instead the device is triggered by a separate tool.
Figure 45:
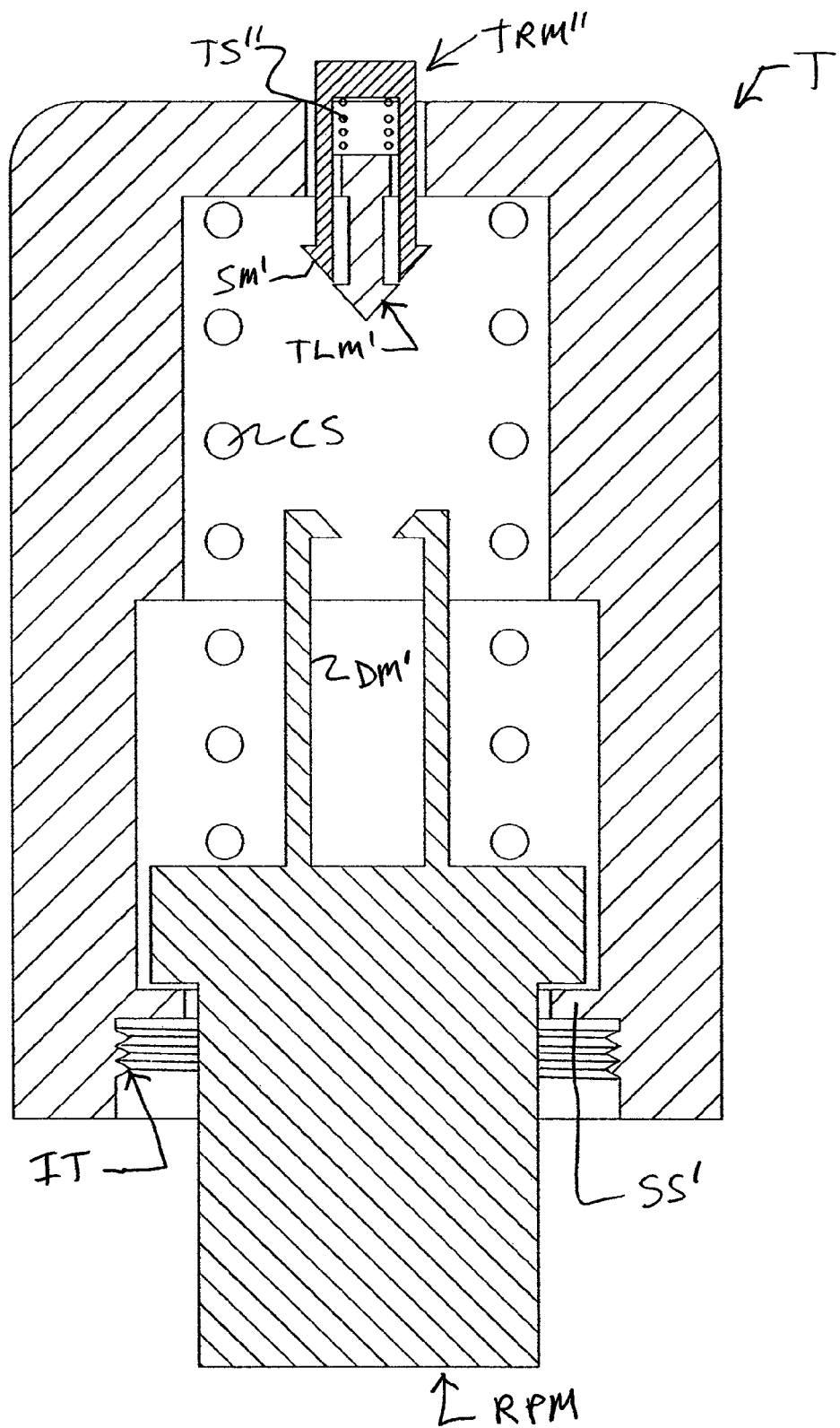
FIG. 45 shows a cross-section view of a tool which can be used to trigger the device of FIG. 44. The tool is shown in post-triggered position and/or a pre-trigger activated position.
Figure 46:
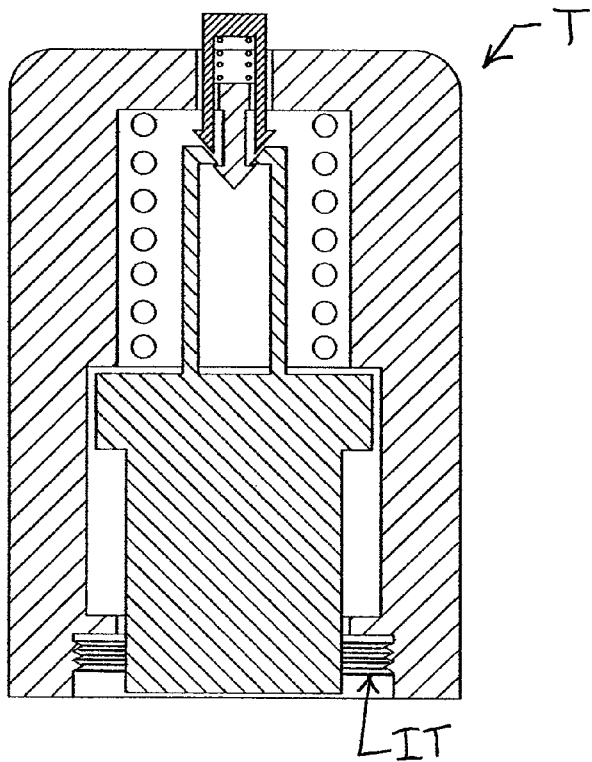
FIG. 46 shows the tool of FIG. 46 in a trigger set position.
Figure 47:
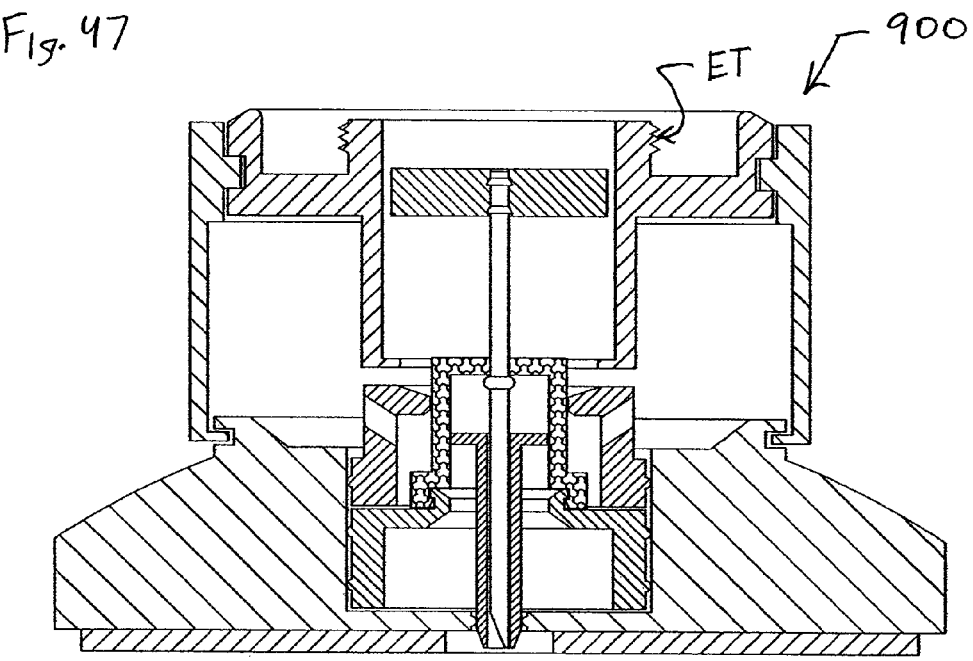
FIG. 47 shows the device of FIG. 44 arranged beneath the tool of FIG. 46.
Figure 48:
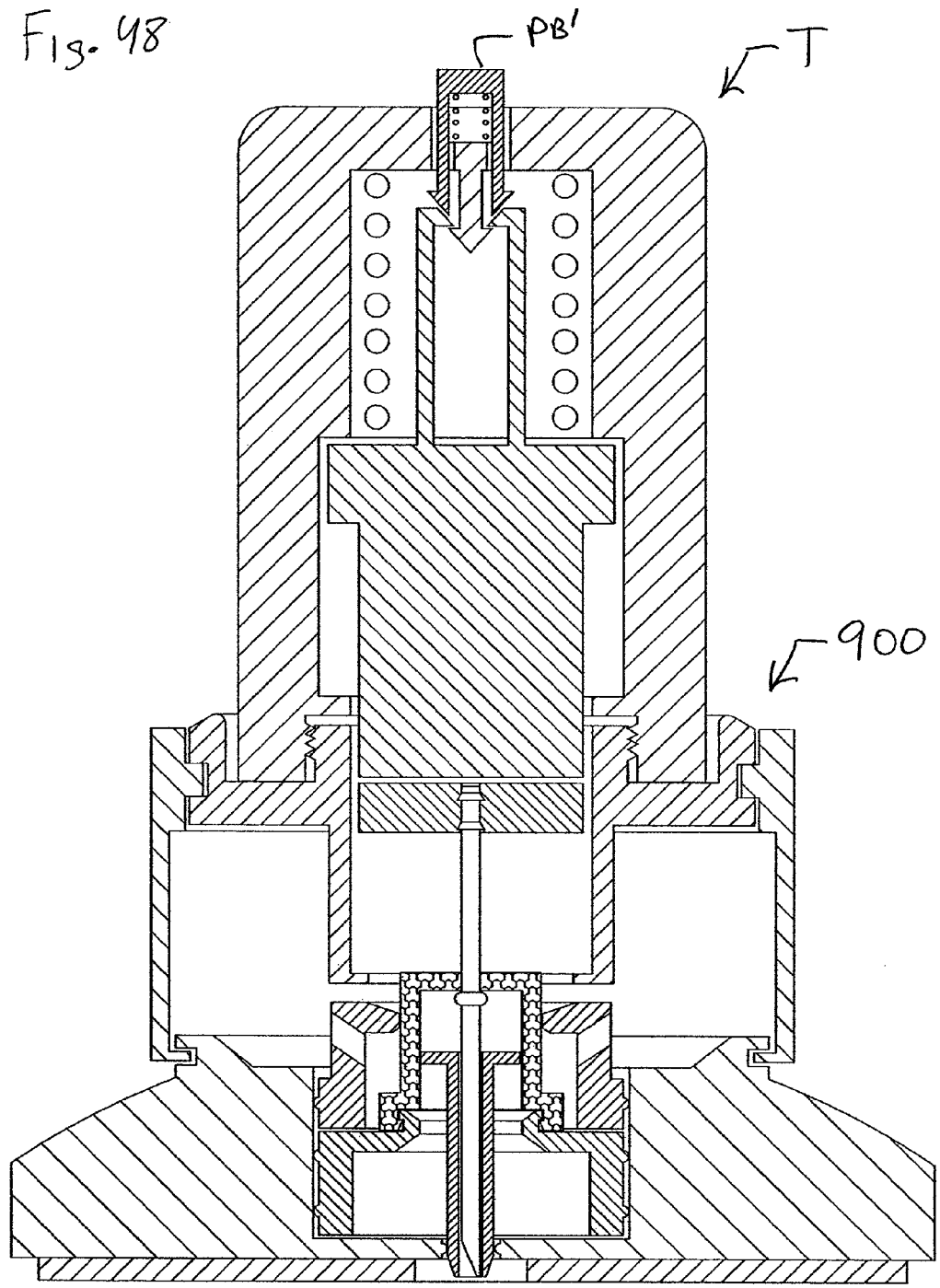
FIG. 48 shows the device of FIG. 44 coupled to the tool of FIG. 46.

FIGS. 44-48 show another non-limiting embodiment of the device 900. This embodiment is similar to that of FIG. 29 except that no trigger release mechanism is utilized on the device 900 and instead the device 900 is triggered by a separate tool T. FIG. 45 shows the tool T which can be used to trigger the device 900. The tool T is shown in post-triggered position and/or a pre-trigger activated position. A user can place the T in the trigger-set position shown in FIG. 46 by pushing in the releasable pushing member RPM until the deflectable members DM' become locked to the member TLM'. FIG. 47 shows the device 900 arranged beneath the tool T and FIG. 48 shows the device 900 coupled to the tool T. This can occur by the user threading the tool T onto the device 900, i.e., by causing the internal threads IT of the tool T to engage with external threads EX of the device 900. Of course, the invention contemplates using other temporary connections between the tool T and the device 900 such as, e.g., a releasable snap-on and/or locking connection.

As can be seen in FIG. 44, fluid delivery device 900 includes a one-piece body 910. However, it may also be multi-piece body. Device 900 also includes removable insertion device 920 that has needle portion 922 that is inserted into body 910. The needle portion 922 includes an integrally formed projection 925 which is sized to pass through the cap 950 without destroying the ability of the cap 950 to reseal the opening formed thereby and is also sized to engage or contact the cannula 930 in order to force the cannula 930 to move axially between the retracted position shown in FIG. 44 and a puncturing position (after the system TRM" of the tool T is triggered). This occurs when the triggering system TRM", whose push-button PB' slides within openings of the tool T, is moved from the position shown in FIG. 48, to a triggering position (see FIG. 45). And because of the biasing force of a metal compression spring CS of the tool T, which applies a biasing force to a releasable pushing member RPM which in turn strikes the disk-shaped need moving member NMM" coupled to the needle 922. A stop shoulder SS' (see FIG. 45) limits downward movement of the member RPM. A second smaller compression TS" is utilized to bias the member TRM" towards the trigger-set position shown in FIG. 46. As in the previous embodiment, triggering occurs when the tapered ends of members SM' engage the tapered ends of deflectable members DM', the needle moving member NMM" is struck by the member RPM and automatically causes the member NMM" to move downwardly. A needle guard (not shown) is coupled to a bottom portion of the body 910. The needle guard may be coupled to the body 910 in any desired way such as, e.g., a friction fit, or any other suitable system of releasable attachment or engagement. Device 900 also includes a generically-depicted adhesive layer AL, which preferably includes a protective backing sheet or release layer (not shown). Adhesive layer AL may have the form of a circular pad having two opposing, adhesive-coated sides, one of which is attached to the relevant portion of the bottom surface of body 910 and the other of which will be attached to a user's body (e.g., once a backing sheet has been removed). Alternatively, one of the two opposing sides may be welded (e.g., ultrasonically welded) to the bottom surface of body 910 instead of being attached via an adhesive. As opposed to using an adhesive layer AL, a portion (e.g., all) of the bottom surface of body 910 may be configured to adhere directly to a living being's skin, such as by making the bottom surface material from a material that chemically reacts with and adheres to skin. Adhesive layer AL is one example of an adhesive portion (of a fluid delivery device) that is configured to adhere directly to a living being's skin. Device 900 also includes a cannula 930 which has one portion extending out past from the adhesive layer AL and another portion arranged within the body 910. As in previous embodiments, the device 900 preferably utilizes a bottom support 960, a septum cap 950 coupled to the bottom support 960 and an upper support 970.

Figure 49:
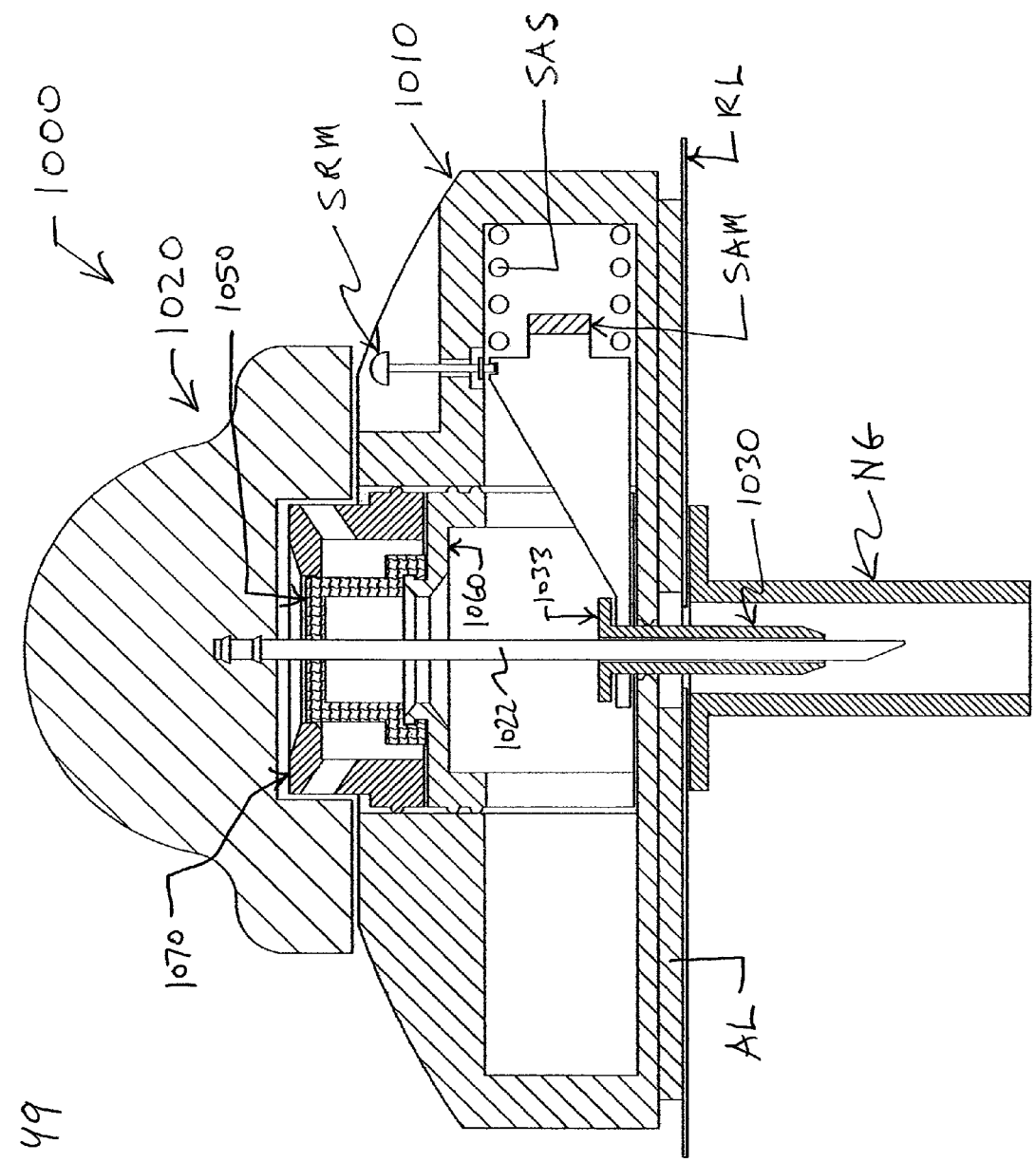
FIG. 49 shows a cross-section view of another non-limiting embodiment of the device. This embodiment is similar to that of FIG. 1 except that it additionally includes internal cavities and a system for automatically causing the cannula to retract into the body so that the device can be safely handled after removal from the user.
Figure 50:
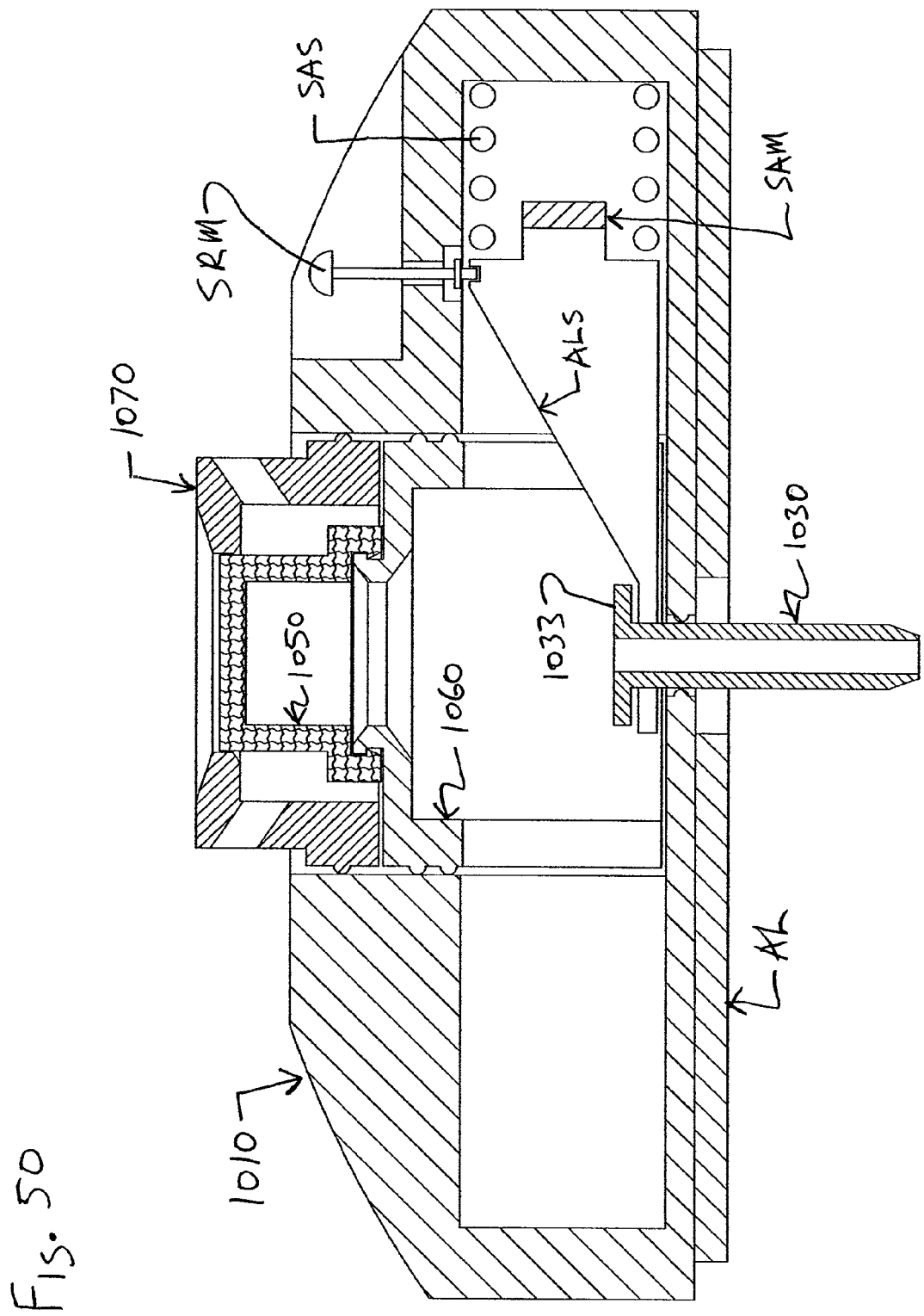
FIG. 50 shows the device of FIG. 49 after the insertion mechanism is removed.
Figure 51:
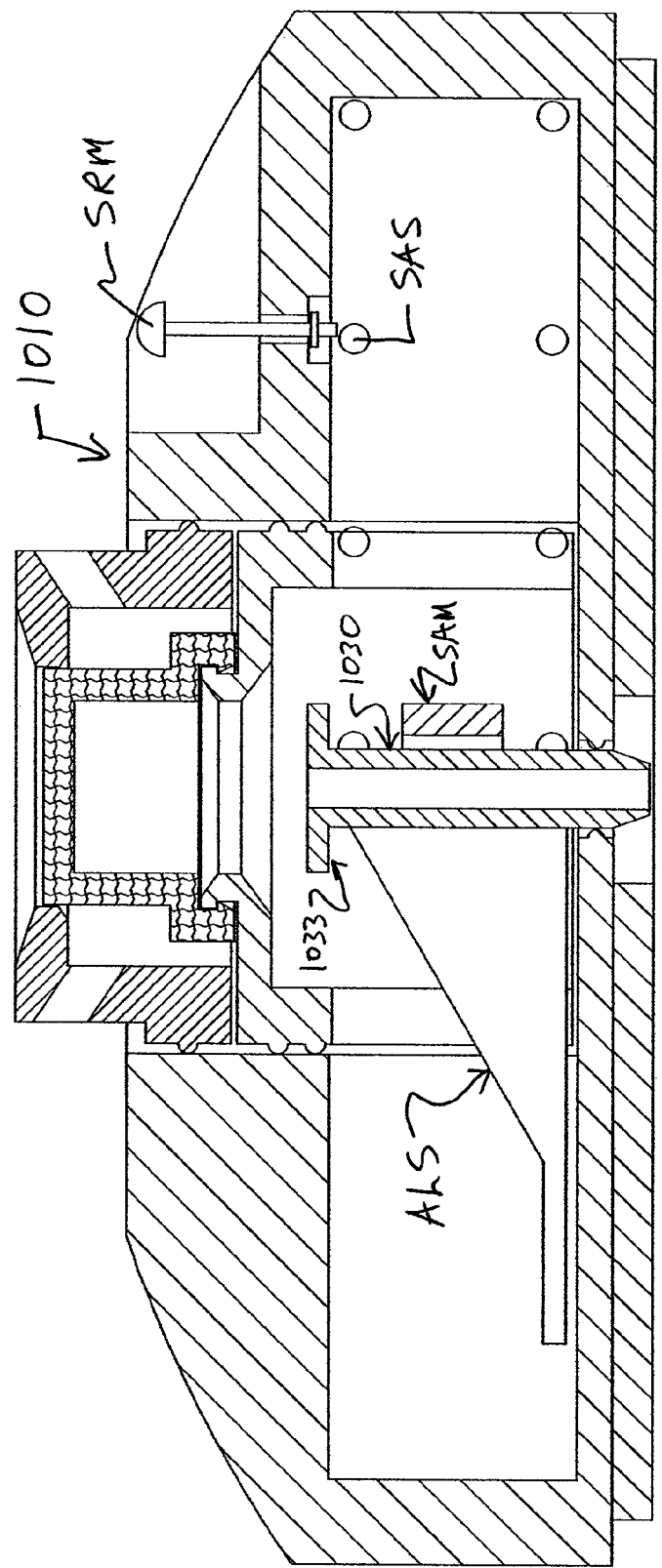
FIG. 51 shows the device of FIG. 50 after the system for automatically causing the cannula to retract into the body is activated and shows the cannula retracted into the body.
Figure 55:
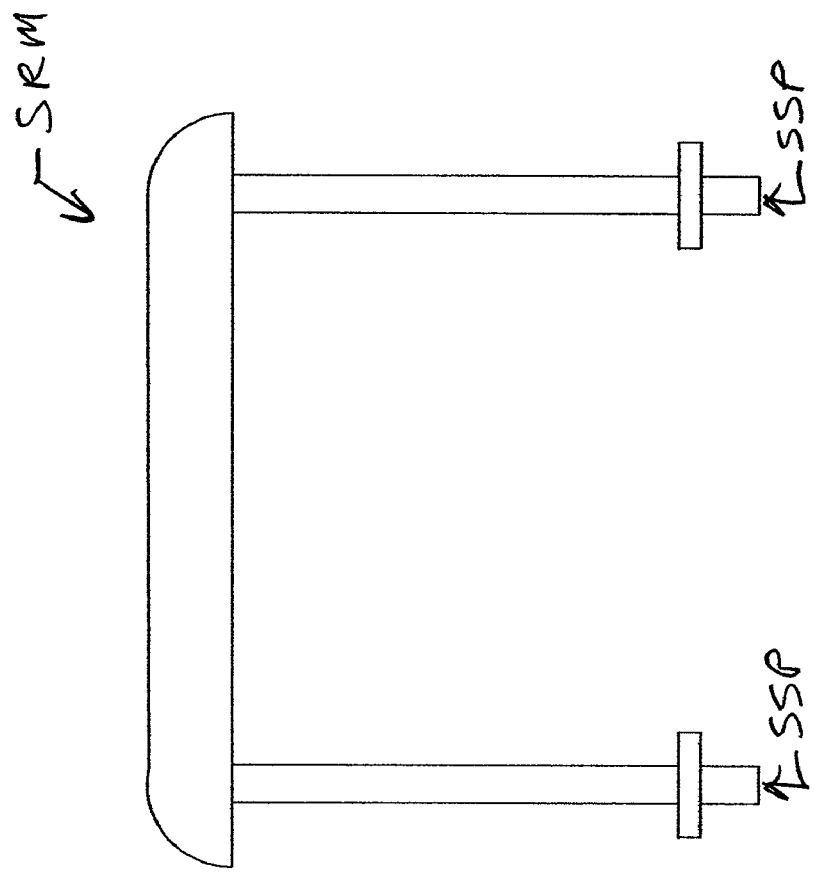
FIG. 55 shows a left-side view of FIG. 54.
Figure 54:
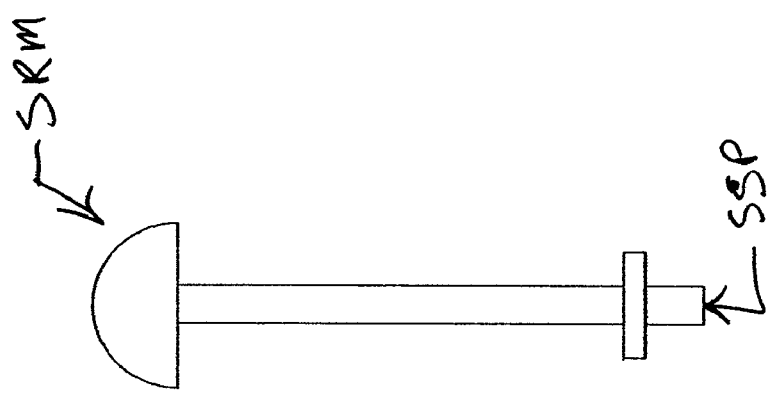
FIG. 54 shows a side view of the safety release mechanism used in the device of FIG. 49.
Figure 56:
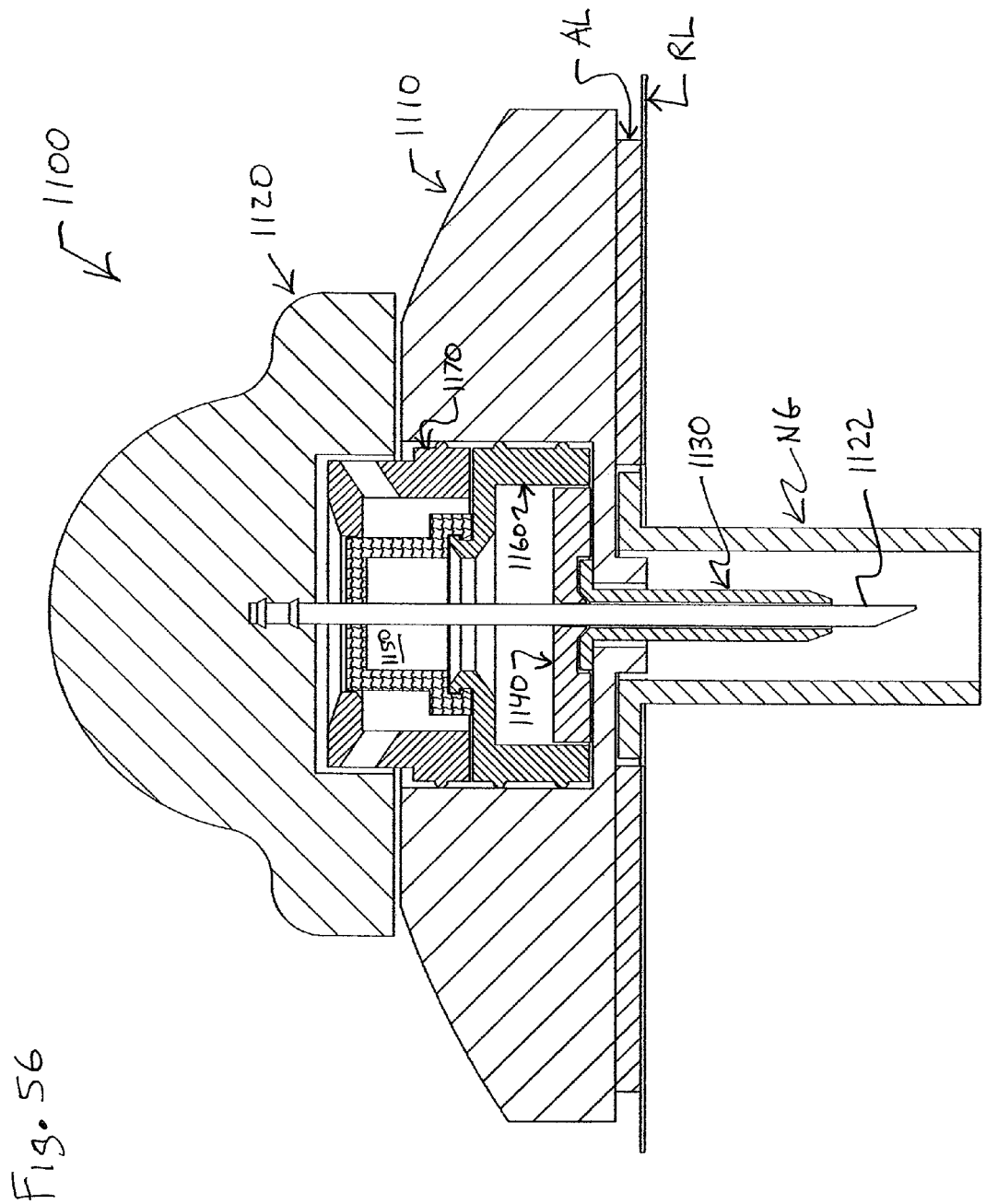
FIG. 56 shows a cross-section view of another non-limiting embodiment of the device. This embodiment is similar to that of FIG. 1 except that it additionally includes an internal needle guide member to ensure, among other things, that the insertion needle does not damage the cannula during assembly of the device and prevent axial inward movement of the cannula when the device is attached to a user.

FIGS. 49-55 show another non-limiting embodiment of the device 1000. This embodiment is similar to that of FIG. 1 except that it additionally includes internal cavities and a system for automatically causing the cannula 1030 to retract into the body 1010 so that the device 1000 can be safely handled after removal from the user. FIG. 50 shows the device 1000 after the insertion mechanism 1020 is removed. FIG. 51 shows the device 1000 after the system for automatically causing the cannula 1030 to retract into the body 1010 is activated and shows the cannula 1030 retracted into the body 1010. As is apparent from a comparison of FIGS. 50 and 51, once a user lifts member SRM, a compressed spring SAS will cause the member SAM to move sideways thereby causing engagement between the tapered surfaces ALS and the shoulder 1033. This, in turn, causes the cannula 1030 to retract into the body 1010. Furthermore, since the device 1000 lacks any mechanism for moving the member SAM back to the position shown in FIG. 50, the device 1000 is rendered unusable after a single-use.

As can be seen in FIG. 49, fluid delivery device 1000 includes a one-piece body 1010. However, it may also be multi-piece body. Device 1000 also includes removable insertion device 1020 that has needle portion 1022 that is inserted into body 1010, and a needle guard NG that is coupled to a bottom portion of the body 1010. The needle guard NG may be coupled to the body 1010 in any desired way such as, e.g., a friction fit, or any other suitable system of releasable attachment or engagement. Device 1000 also includes a generically-depicted adhesive layer AL, which preferably includes a protective backing sheet or release layer (not shown). Adhesive layer AL may have the form of a circular pad having two opposing, adhesive-coated sides, one of which is attached to the relevant portion of the bottom surface of body 1010 and the other of which will be attached to a user's body (e.g., once a backing sheet has been removed). Alternatively, one of the two opposing sides may be welded (e.g., ultrasonically welded) to the bottom surface of body 1010 instead of being attached via an adhesive. As opposed to using an adhesive layer AL, a portion (e.g., all) of the bottom surface of body 1010 may be configured to adhere directly to a living being's skin, such as by making the bottom surface material from a material that chemically reacts with and adheres to skin. Adhesive layer AL is one example of an adhesive portion (of a fluid delivery device) that is configured to adhere directly to a living being's skin. Device 1000 also includes a cannula 1030 which has one portion extending out past from the adhesive layer AL and another portion arranged within the body 1010. Device 1000 additionally includes a bottom support 1060, a septum cap 1050 coupled to the bottom support 1060 and an upper support 1070. With the exception of a passage which allows for movement therethrough of member SAM which necessitates a longer axial length, the lower support 1060 can be similar to lower support 60 shown in FIG. 1 The upper support 1070, septum cap 1050, and cannula 1030 can be substantially similar or identical to the corresponding features 70, 50 and 30 shown in FIG. 1

FIGS. 56-59 show another non-limiting embodiment of the device 1100. This embodiment is similar to that of FIG. 1 except that it additionally includes an internal needle guide member 1140 to ensure, among other things, that the insertion needle 1122 does not damage the cannula 1130 during assembly of the device 1100 and prevents axial inward movement of the cannula 1130 when the device 1100 is being attached to a user.

Figure 57:
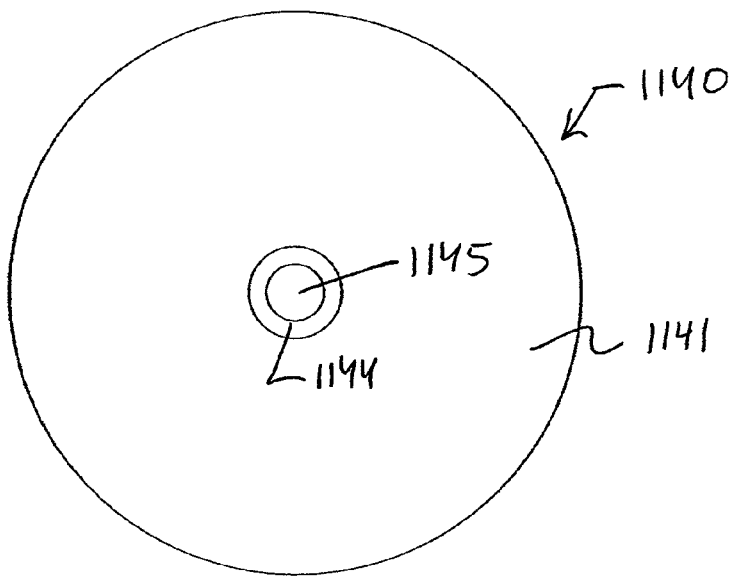
FIG. 57 shows a top view of the internal needle guide member shown in FIG. 58.
Figure 58:
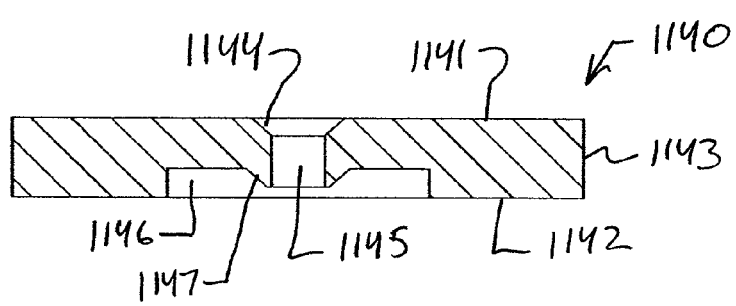
FIG. 58 shows a side cross-section view of the internal needle guide used in the device of FIG. 56.
Figure 59:
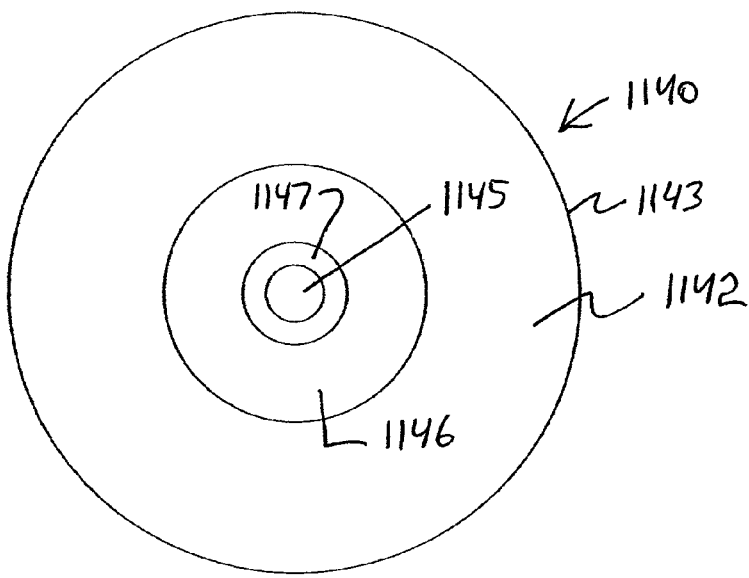
FIG. 59 shows a bottom view of the internal needle guide member shown in FIG. 58.
Figure 60:
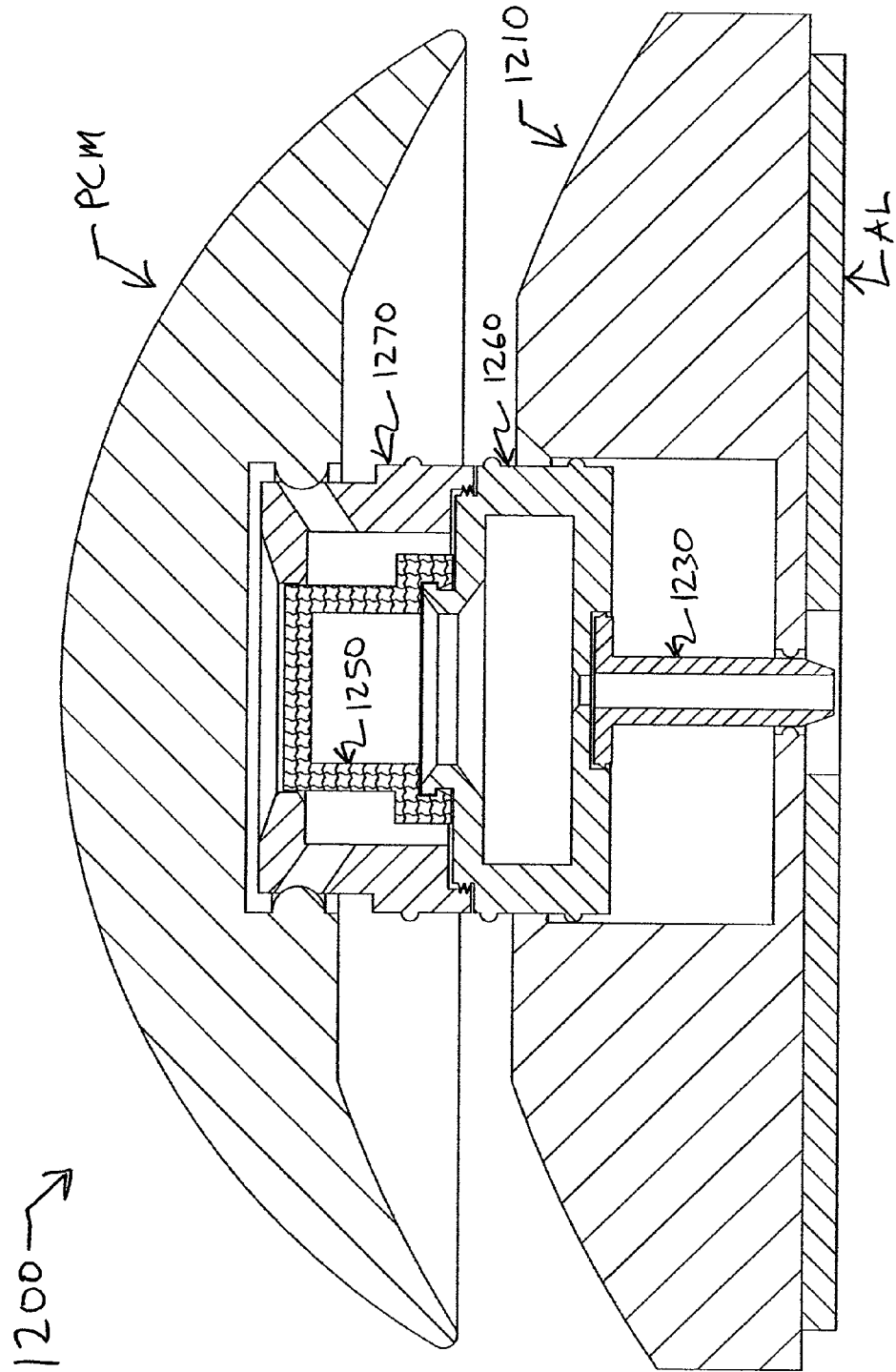
FIG. 60 shows a cross-section view of another non-limiting embodiment of the device. This embodiment is similar to that of FIG. 1 except that it utilizes a movable injection module made up of a cannula, the lower support, the upper support, and the septum cap. A removable pushing cap member is utilized to move the injection module from the initial position shown in FIG. 60 to a puncturing position. In contrast to previous embodiments, no insertion needle is utilized and instead the cannula is of the rigid type.

With reference to FIGS. 57-59, needle guide member 1140 can be a one-piece synthetic resin member made of medical grade metals or plastics including those currently used to make known fluid delivery devices. By way of non-limiting example, the member 1140 has a substantially ring-shaped bottom surface 1142, a main central generally cylindrical space 1146, an outer generally cylindrical surface 1143 which optionally includes one or more sealing projections (not shown), a substantially ring-shaped upper surface 1141, and an upper generally circular opening 1145 having a chamfer 1144. A lower chamfered end 1147 can be arranged on an opposite side of the member 1140. Non-limiting axial thickness ranges for the member 1140 can be between about 0.02 inches to about 0.10 inches, and is preferably between about 0.03 inches and about 0.60 inches.

Figure 61:
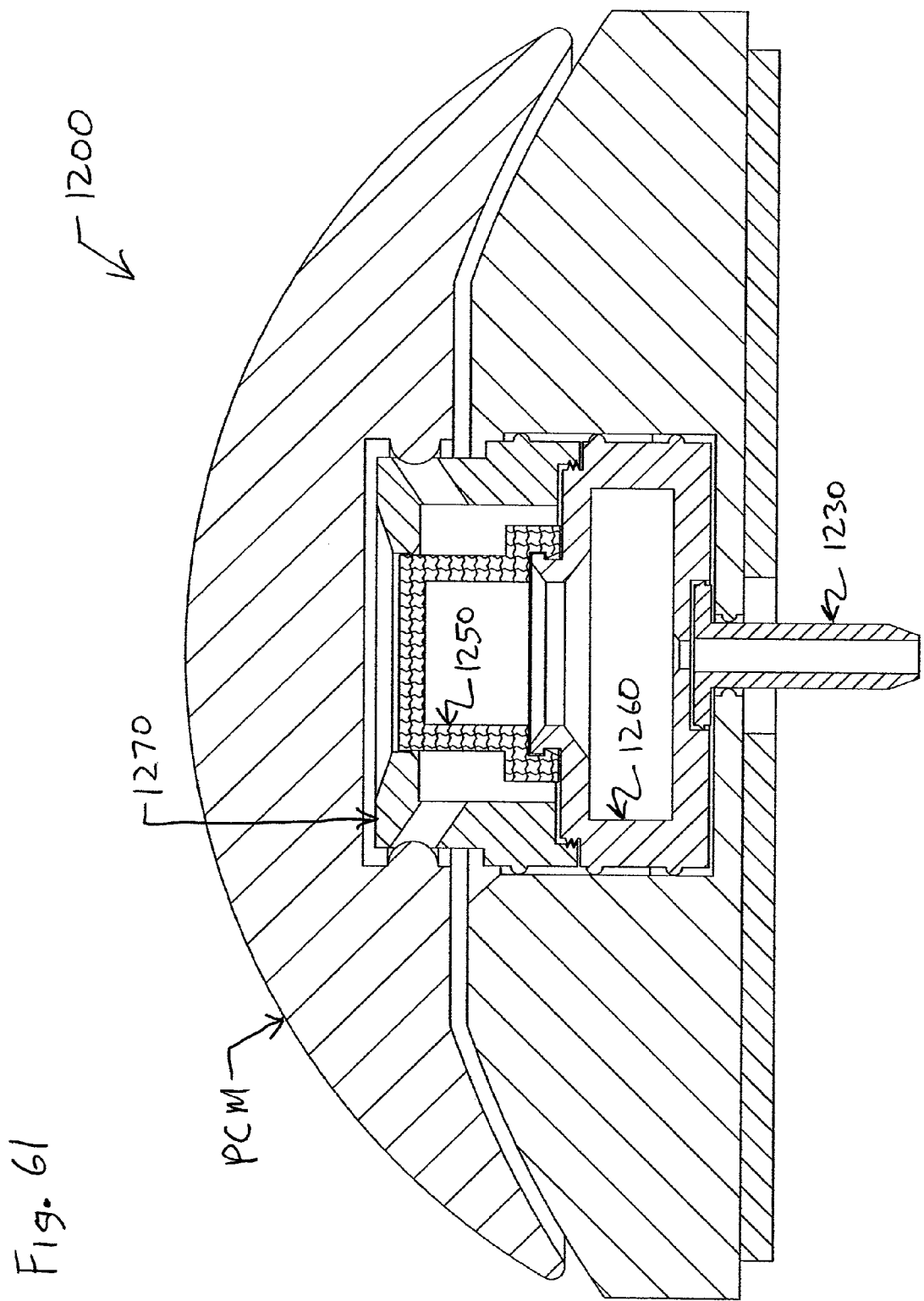
FIG. 61 shows the device of FIG. 60 after the pushing cap is moved towards the body and caused the injection module to move to the puncturing position.
Figure 62:
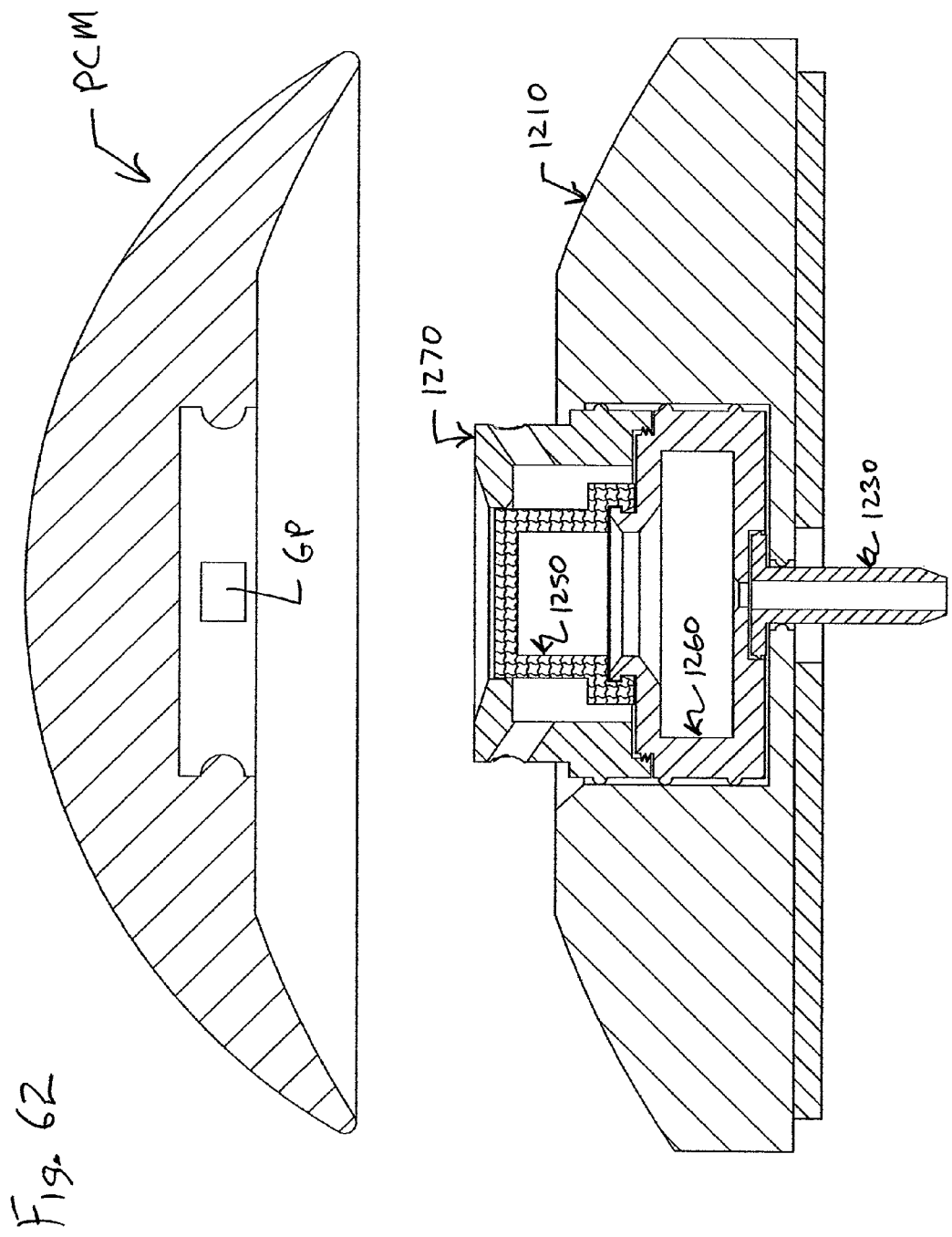
FIG. 62 shows the device of FIG. 61 after the pushing cap is uncoupled from the body.
Figure 63:
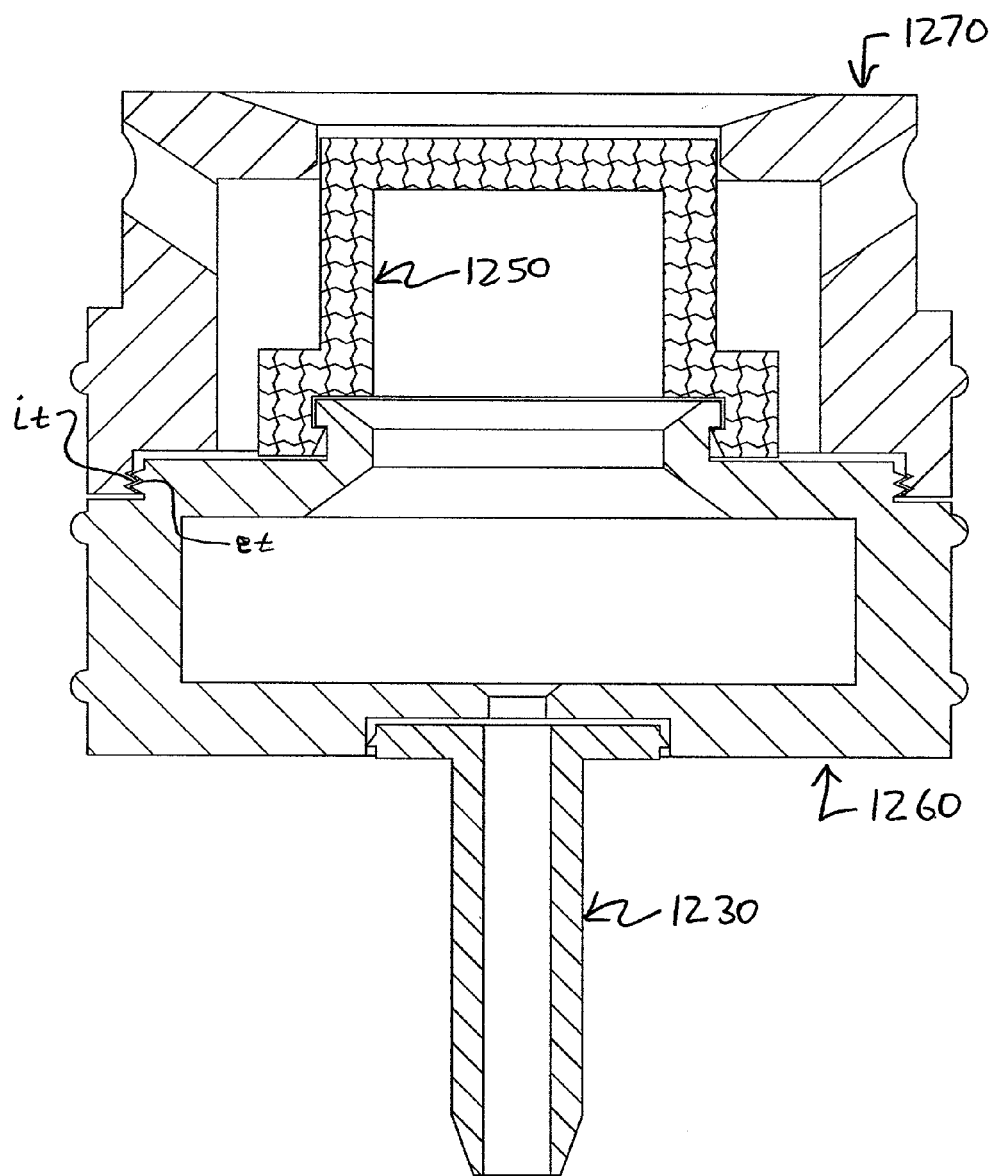
FIG. 63 shows an enlarged cross-section view of the injection module used in the embodiment shown in FIG. 60.
Figure 64:
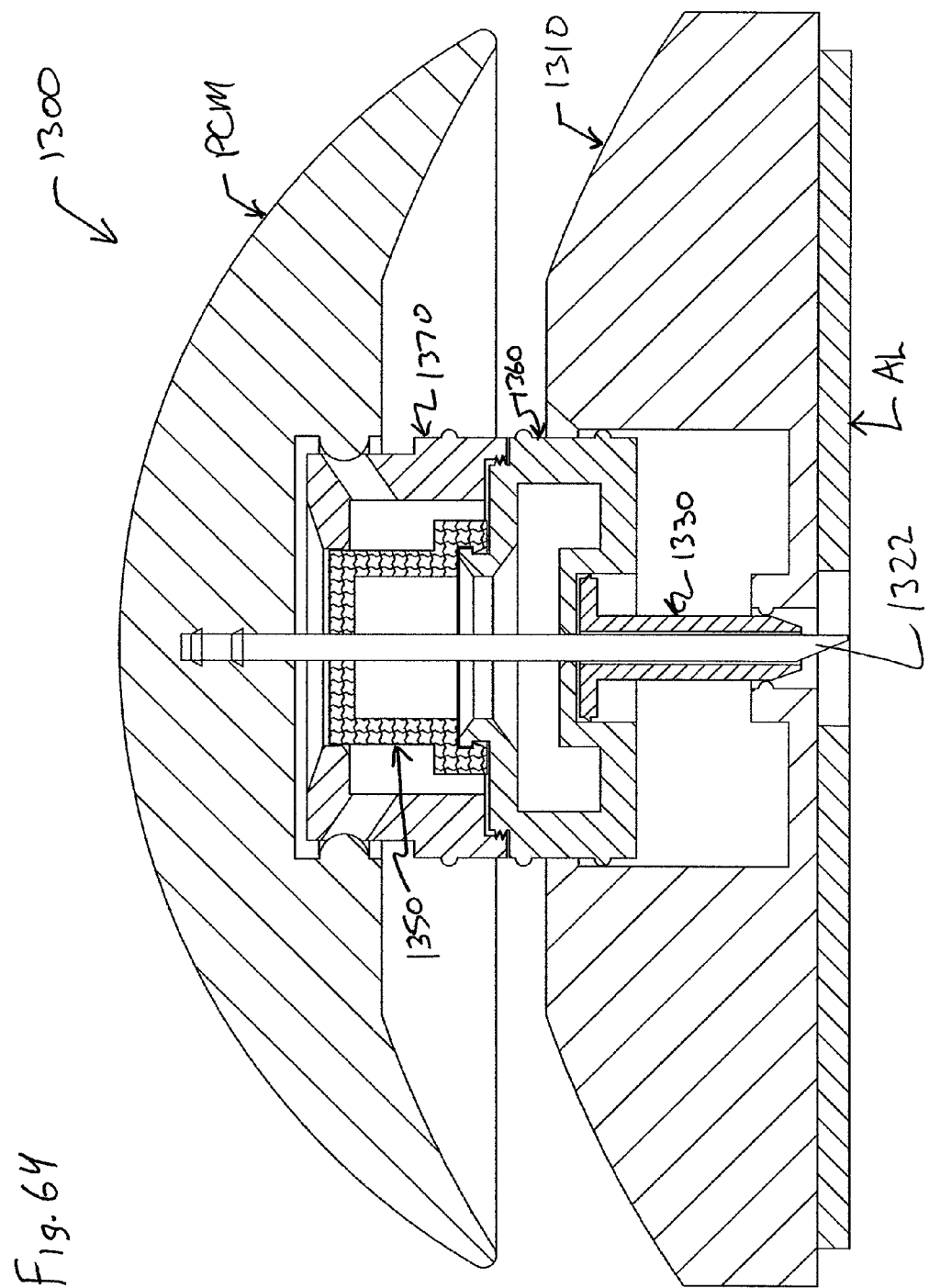
FIG. 64 shows a cross-section view of another non-limiting embodiment of the device. This embodiment is similar to that of FIG. 60 except that it utilizes an insertion needle mechanism, a part of which includes the pushing cap. The body and lower support are modified. The cannula is of the type used in the embodiment of FIG. 1.
Figure 65:
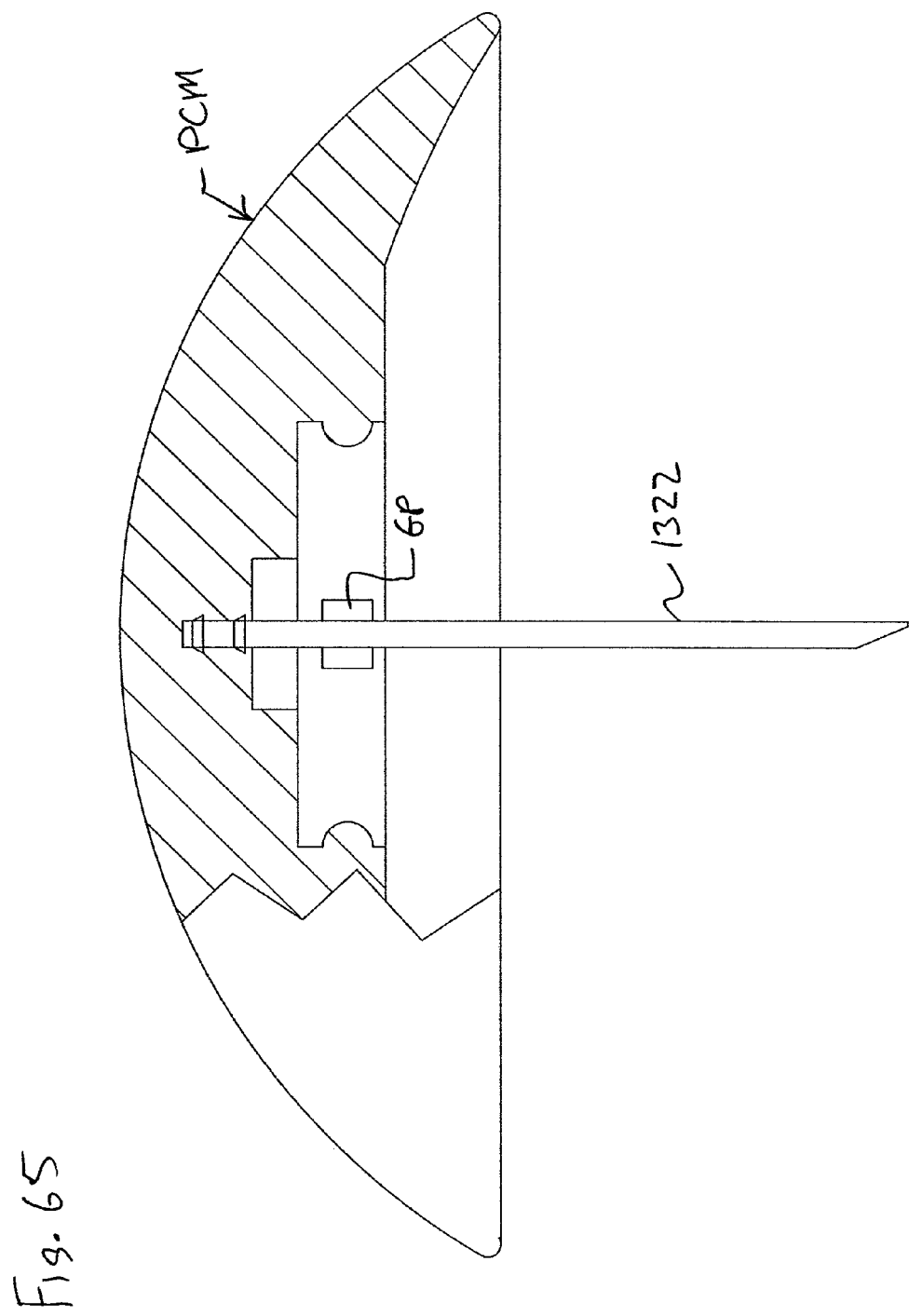
FIG. 65 shows an enlarged partial cross-section view of the insertion needle mechanism used in the embodiment shown in FIG. 64.
Figure 66:
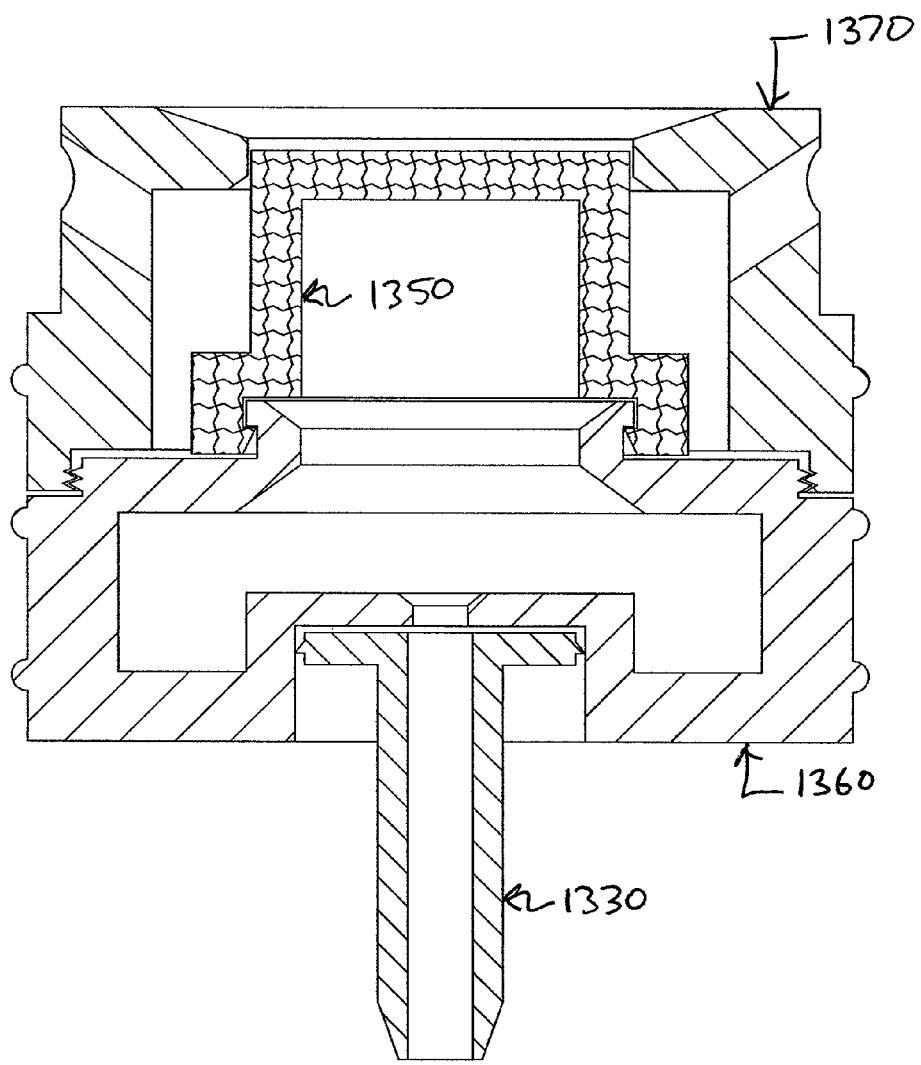
FIG. 66 shows an enlarged cross-section view of the injection module used in the embodiment shown in FIG. 64.
Figure 67:
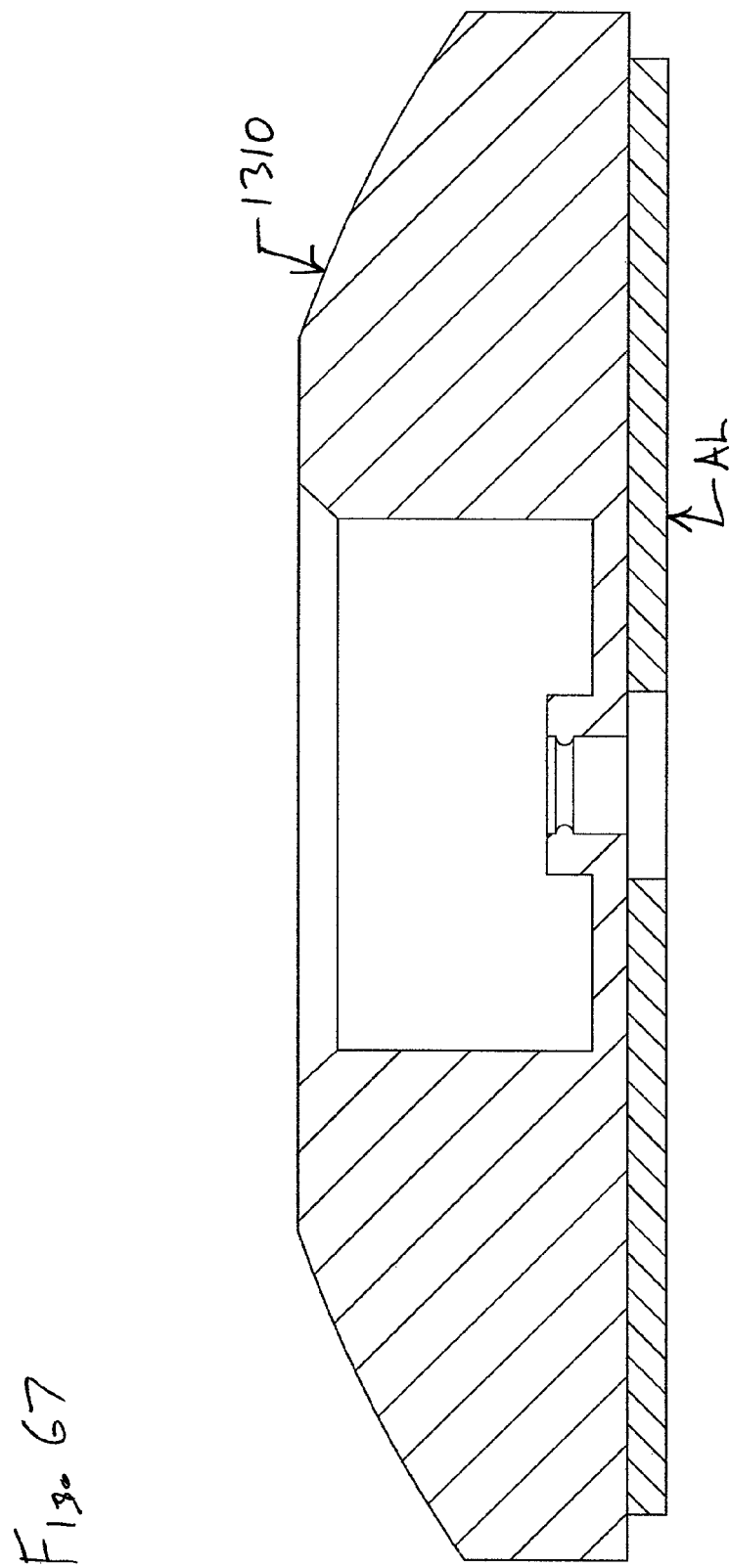
FIG. 67 shows an enlarged cross-section view of the body member and adhesive layer used in the embodiment shown in FIG. 64.

FIGS. 60-63 show another non-limiting embodiment of the device 1200. This embodiment is similar to that of FIG. 1 except that it utilizes a movable injection module made up of a cannula 1230, a lower support 1260, a upper support 1270, and a septum cap 1250. A removable pushing cap member PCM is utilized to move the injection module from the initial position shown in FIG. 60 to a puncturing position shown in FIG. 61. In contrast to previous embodiments, no insertion needle is utilized and instead the cannula 1230 is of the rigid type, i.e., it is capable of penetrating into a user's skin without the aid of a needle. FIG. 61 shows the device 1200 after the pushing cap PCM is moved towards the body 1210 and caused the injection module 1270/1250/1260/1230 to move to the puncturing position. FIG. 62 shows the device 1200 after the pushing cap PCM is uncoupled from the body 1210. Gripping projections GP are formed in the member PCM in order to temporarily secure the member PCM to the upper support 1270. FIG. 63 shows an enlarged cross-section view of the injection module used in the embodiment shown in FIG. 60. By way of non-limiting example, the upper support 1270 and lower support 1260 can be connected together via external threads "et" and internal threads "it".

FIGS. 64-67 show another non-limiting embodiment of the device 1300. This embodiment is similar to that of FIG. 60 except that it utilizes an insertion needle mechanism which includes an insertion needle 1322 and the pushing cap PCM. The body 1310 and lower support 1360 are modified from the corresponding members in FIG. 60. The cannula is of the type used in the embodiment of FIG. 1. Otherwise, the device 1300 functions like that of FIG. 60.

Figure 68:
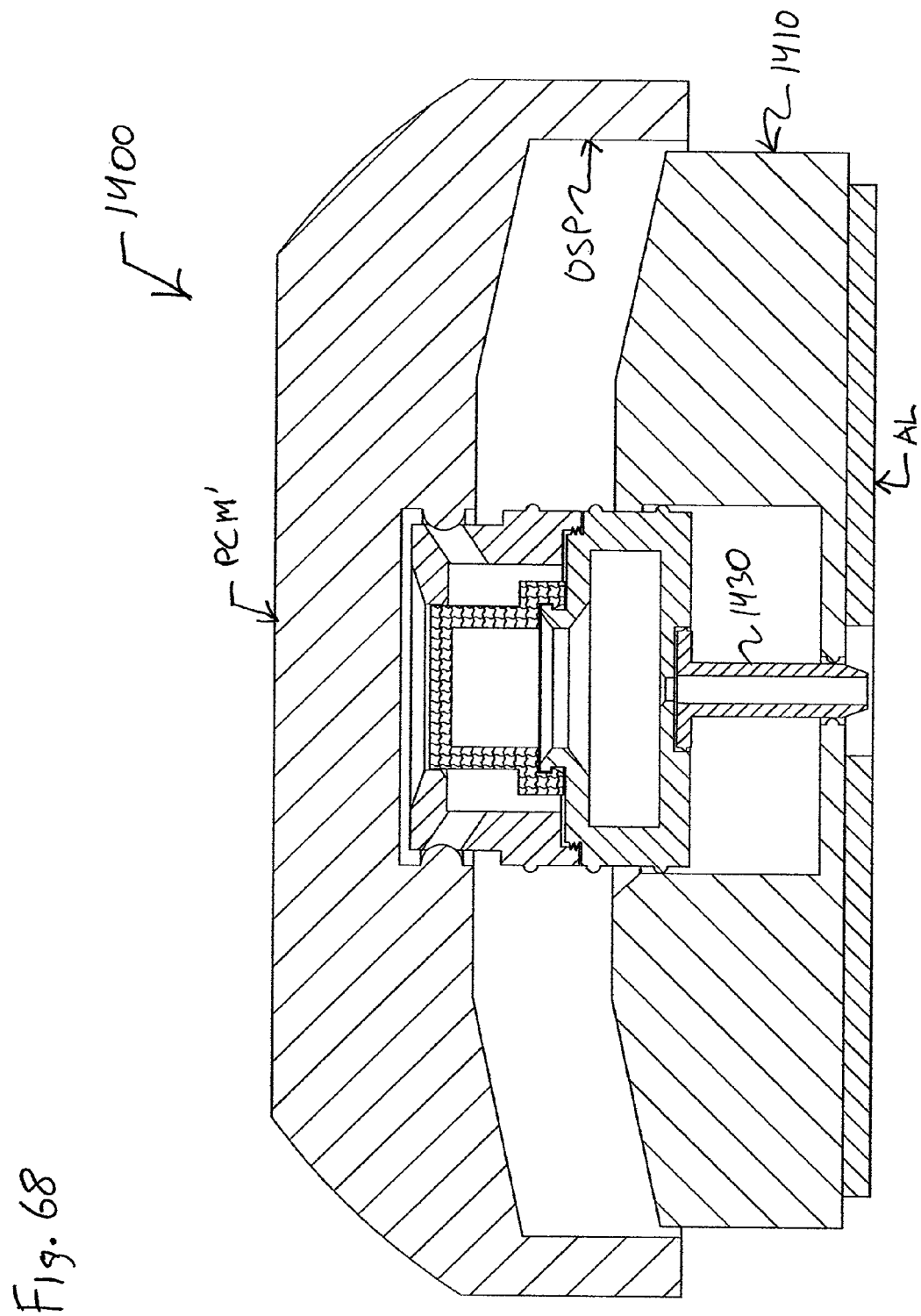
FIG. 68 shows a cross-section view of another non-limiting embodiment of the device. This embodiment is similar to that of FIG. 60 except that it utilizes removable pushing cap member that has an outer sleeve portion which slidably engages with an outer cylindrical surface of the body. In contrast to most previous embodiments, no insertion needle is utilized and instead the cannula is of the rigid type.
Figure 69:
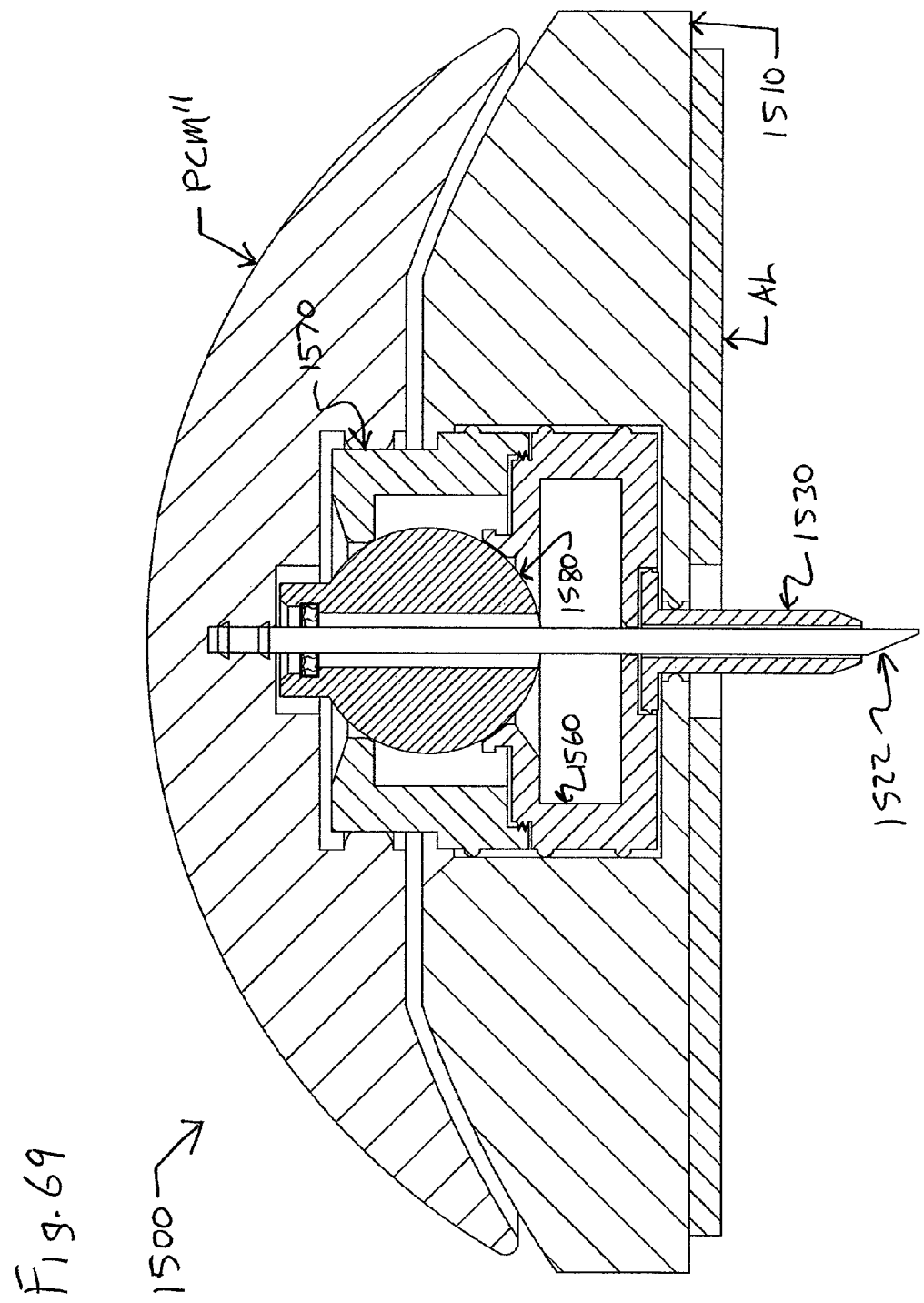
FIG. 69 shows a cross-section view of another non-limiting embodiment of the device. This embodiment is similar to that of FIG. 60 except that it utilizes removable pushing cap member that is part of a needle insertion mechanism, except that the injection module is not movable by the user, and except that the injection module utilizes an adjustable, i.e., one which can swivel, septum support instead of a septum cap.

FIG. 68 shows another non-limiting embodiment of the device 1400. This embodiment is similar to that of FIG. 60 except that it utilizes removable pushing cap member PCM' that has an outer sleeve portion OSP which slidably engages with an outer cylindrical surface of the body 1410. In contrast to most previous embodiments, no insertion needle is utilized and instead the cannula 1430 is of the rigid type.

Figure 70:
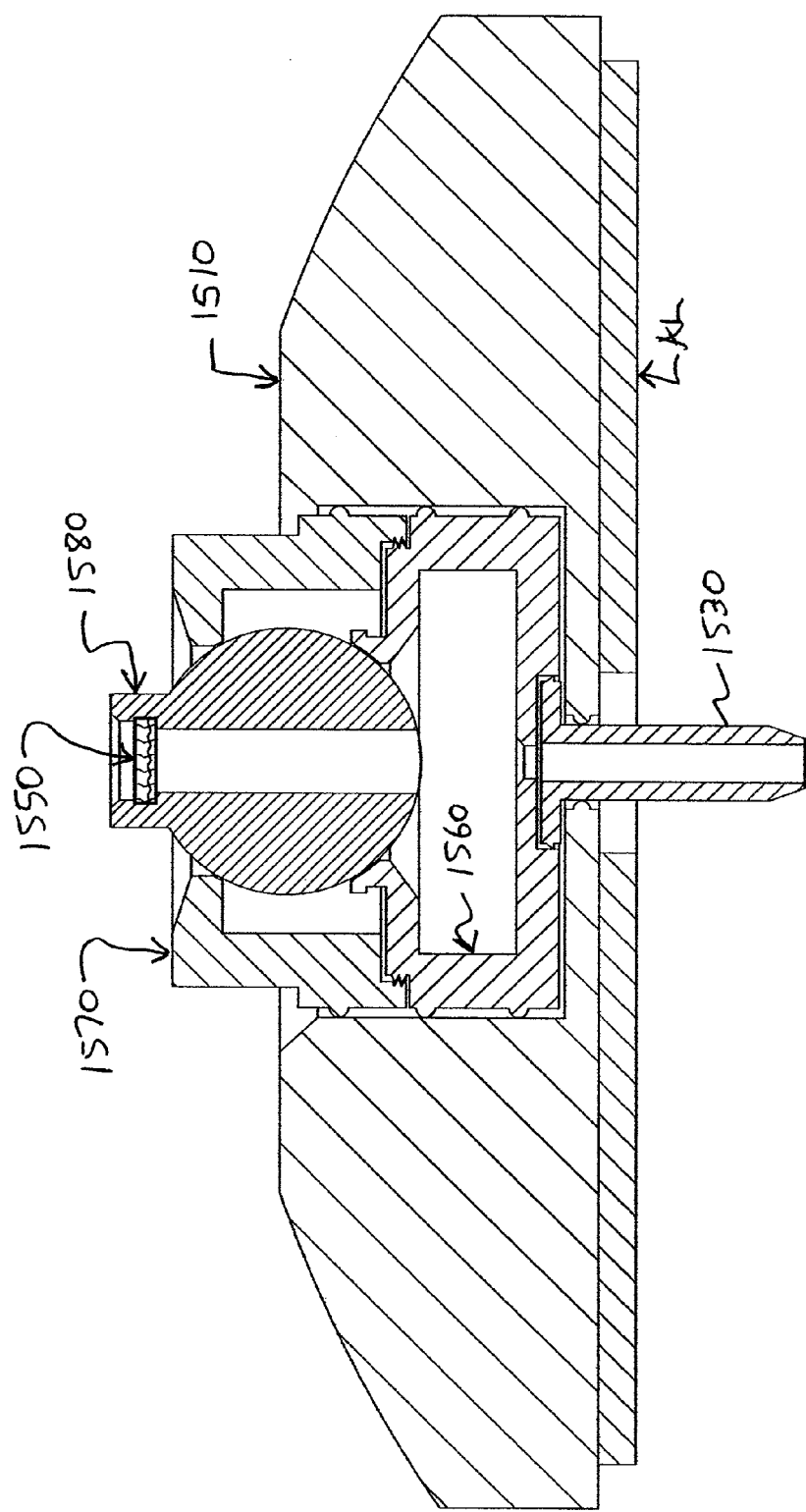
FIG. 70 shows the device of FIG. 69 after the pushing cap/needle insertion mechanism is removed. The adjustable septum support is shown in a centered position.
Figure 71:
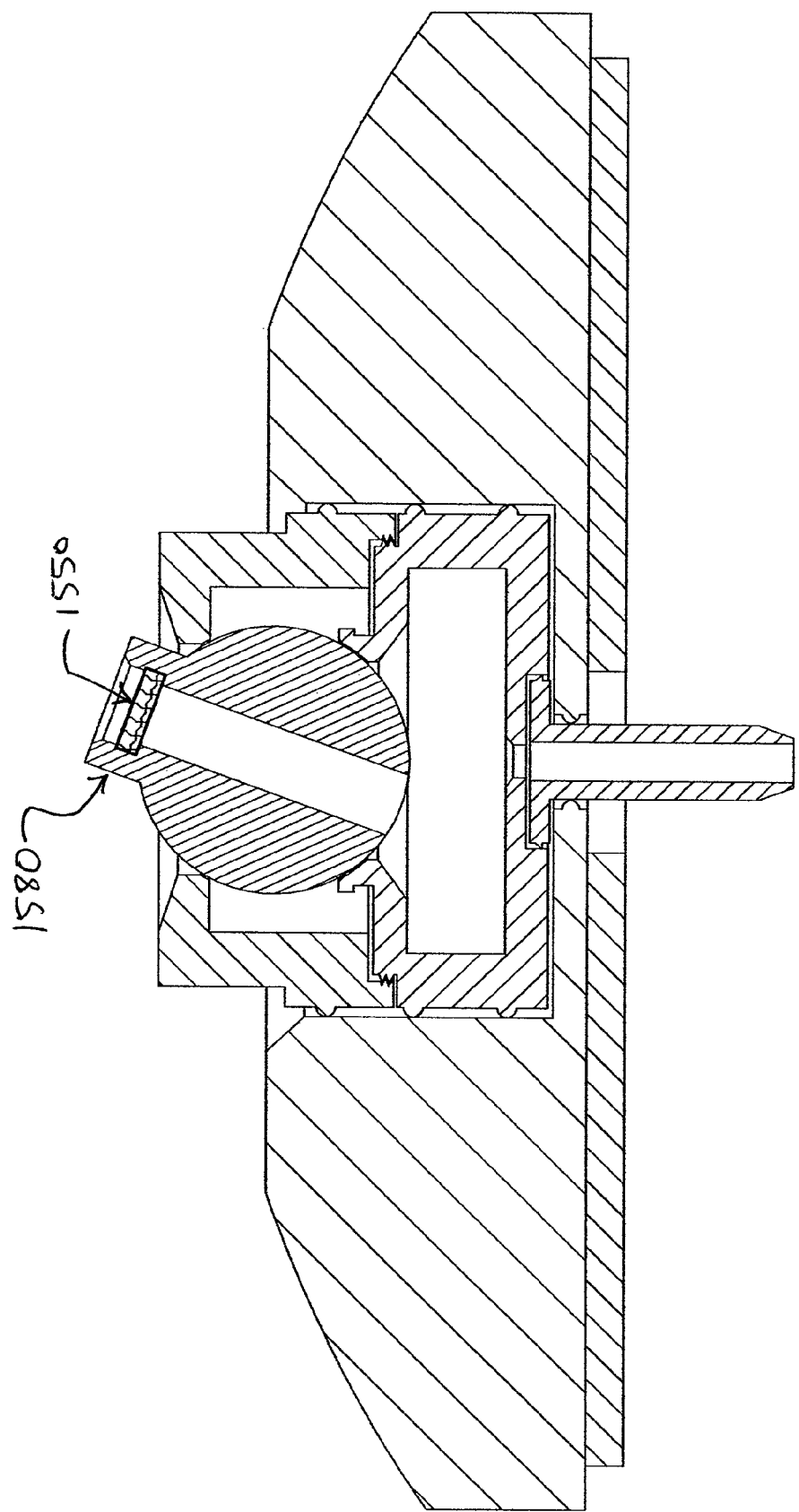
FIG. 71 shows the device of FIG. 70 with the adjustable septum support being shown in one swiveled/tilted position.
Figure 72:
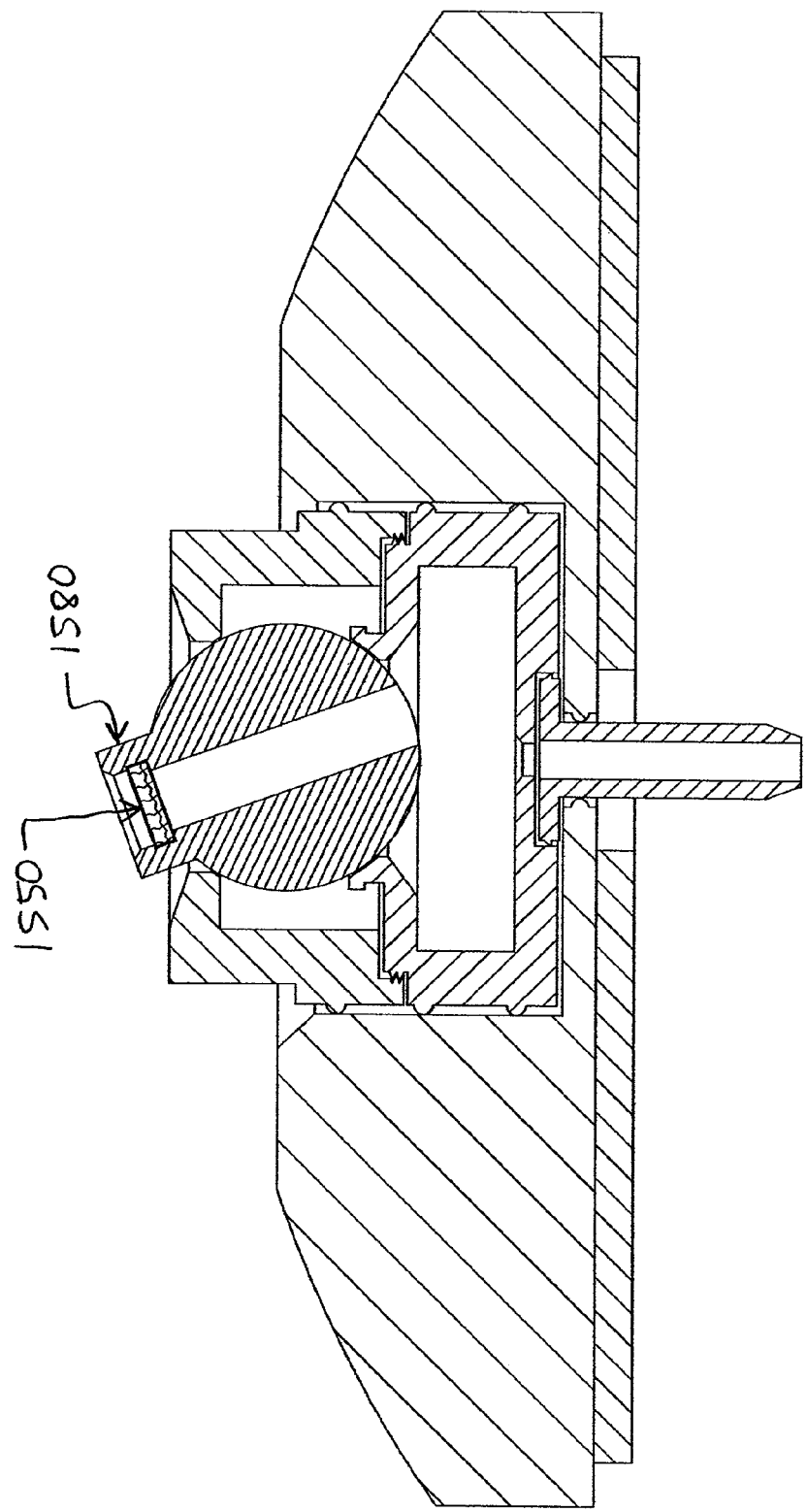
FIG. 72 shows the device of FIG. 70 with the adjustable septum support being shown in another swiveled/tilted position.
Figure 73:
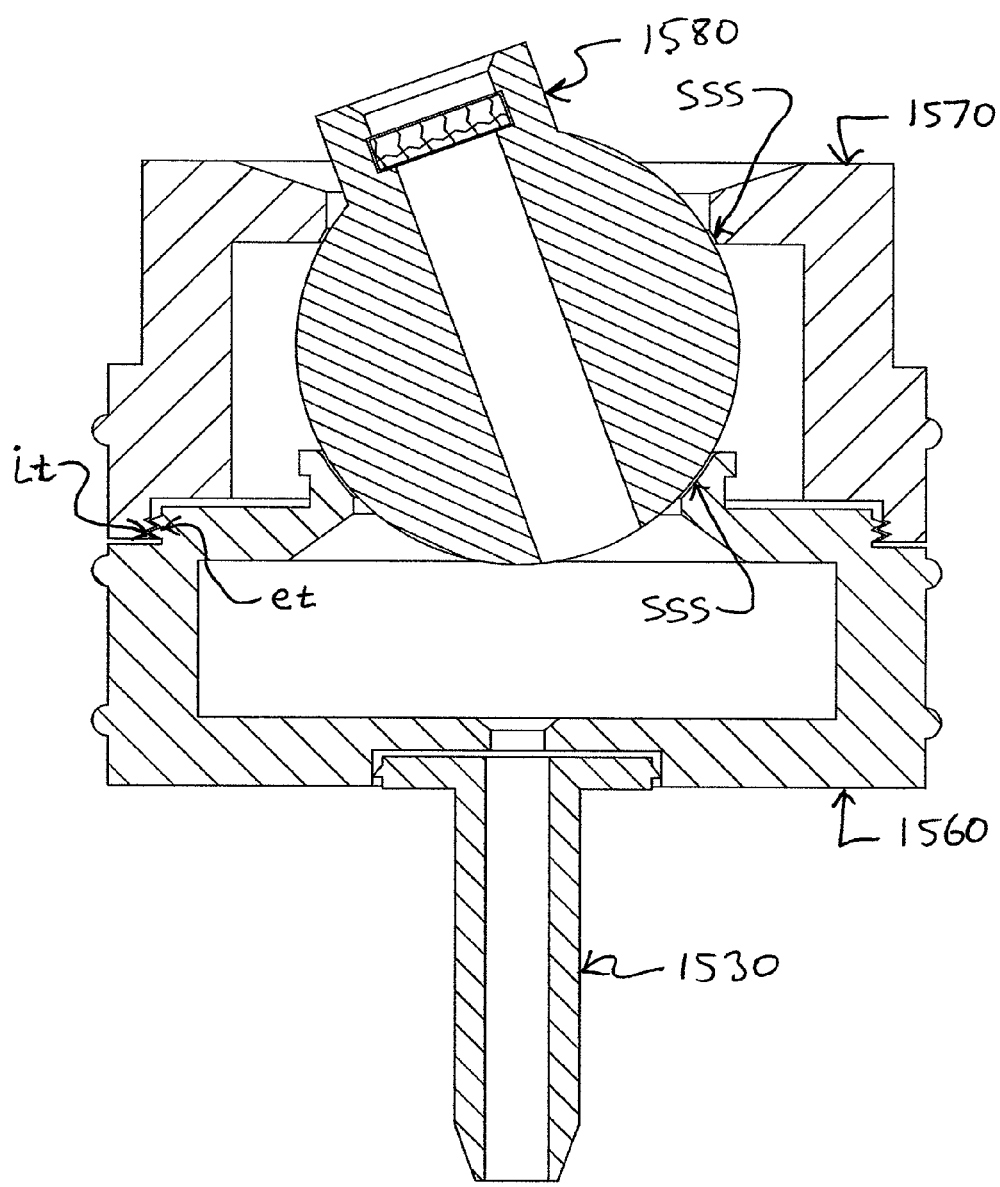
FIG. 73 shows an enlarged cross-section view of the injection module shown in the device of FIG. 72.
Figure 74:
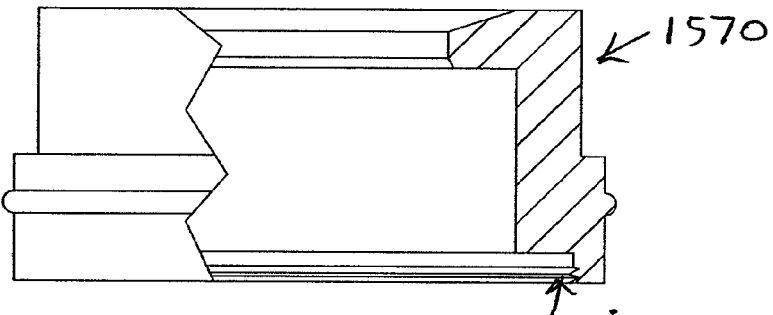
FIG. 74 shows a partial cross-section view of the upper support shown in FIG. 73.
Figure 75:
FIG. 75 shows a partial cross-section view of the septum member shown in FIG. 73.
Figure 76:
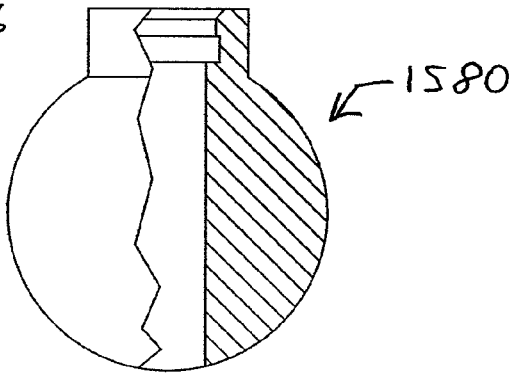
FIG. 76 shows a partial cross-section view of the adjustable septum support shown in FIG. 73.
Figure 77:
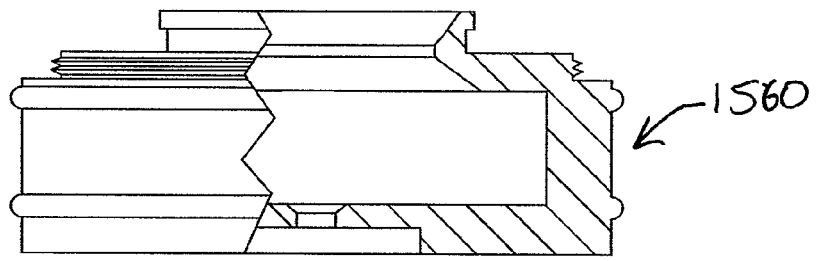
FIG. 77 shows a partial cross-section view of the lower support shown in FIG. 73.
Figure 78:
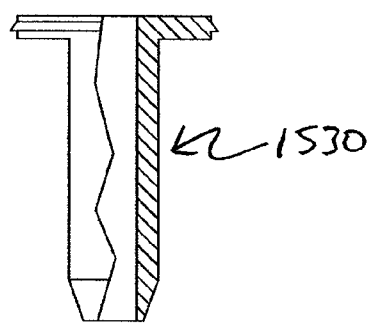
FIG. 78 shows a partial cross-section view of the cannula shown in FIG. 73.

FIGS. 69-78 show another non-limiting embodiment of the device 1500. This embodiment is similar to that of FIG. 60 except that it utilizes removable pushing cap member PCM" that is part of a needle insertion mechanism which includes an insertion needle 1522, except that the injection module 1570/1580/1550/1560/1530 is not movable by the user, and except that the injection module utilizes an adjustable, i.e., one which can swivel, septum support 1580 instead of a septum cap. FIG. 70 shows the device 1500 after the pushing cap/needle insertion mechanism PCM"/1522 is removed. The adjustable septum support 1580 is shown in a centered position in FIG. 70. FIG. 71 shows the device 1500 with the adjustable septum support 1580 being shown in one of a number of possible swiveled/tilted positions and FIG. 72 shows the device 1500 with the adjustable septum support 1580 being shown in another swiveled/tilted position. FIG. 73 shows an enlarged cross-section view of the injection module and shows that the supports 1570 and 1560 each have spherical support surfaces SSS which frictionally engage with an outer spherical surface of member 1580. The embodiment of FIG. 69 can also be modified to utilize spring actuated cannula insertion as in previous embodiments.

Figure 79:
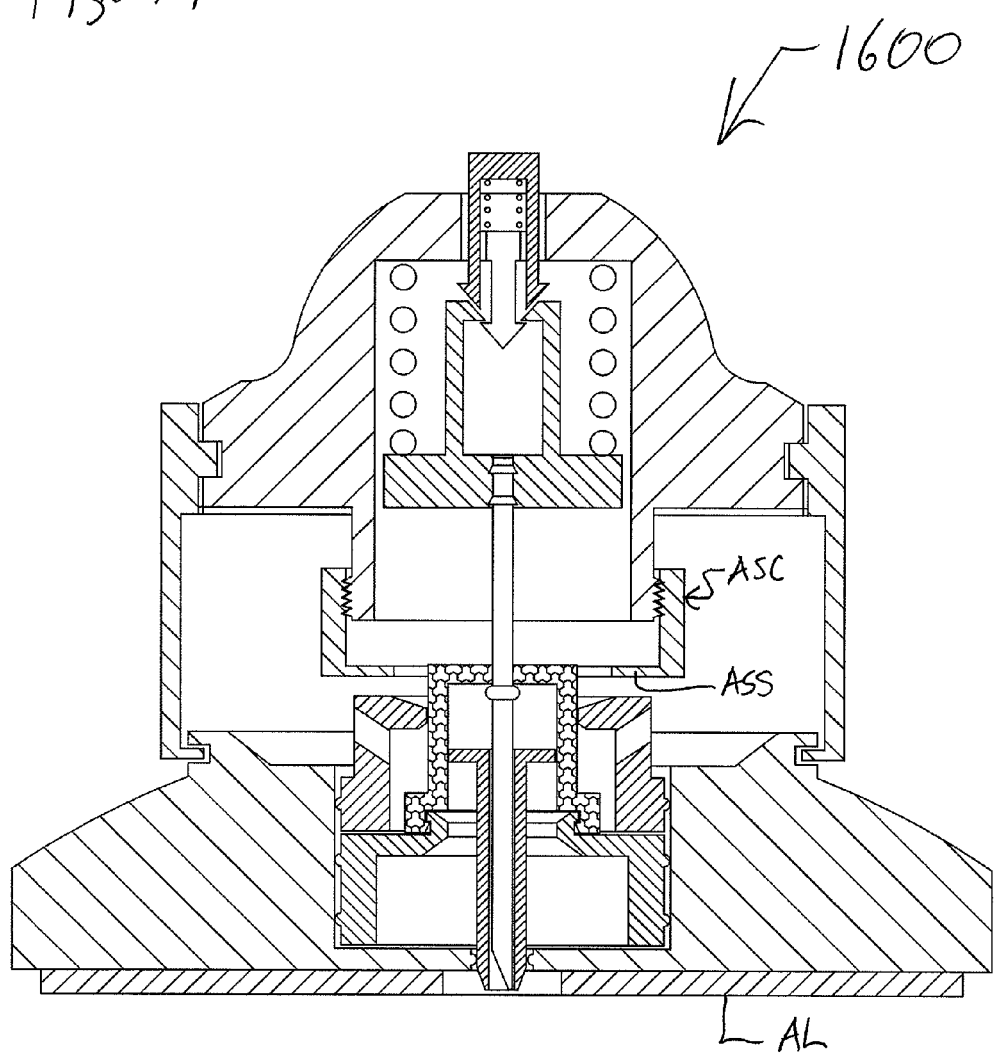
FIG. 79 shows a cross-section view of another non-limiting embodiment of the device. This embodiment is similar to that of FIG. 33 except that it additionally utilizes a user adjustable depth setting system which allows the user to control the insertion depth of the cannula.

FIG. 79 shows another non-limiting embodiment of the device 1600. This embodiment is similar to that of FIG. 33 except that it additionally utilizes a user adjustable depth setting system which allows the user to control the insertion depth of the cannula. The system includes an axially movable adjustable stop cap ASC having the adjustable stop shoulder ASS. The adjustment can take be accomplished in various ways such as a threaded connection which allows the user to rotate member ASC to a desired axial position. Indicia (not shown) can be utilized on the member ASC along with an indicator on the externally threaded portion to which it threads in order to provide the user with an indication of the depth setting position. This can include, e.g., the values, D (for deep depth), M (for medium depth) and S (for shallow depth). Of course, the invention contemplates using such a depth adjustment system on other embodiments such as the embodiments of FIGS. 17, 60, 64 and 68 (by utilizing various thickness shims between the member 421 and body 410, FIG. 23, FIG. 29, and FIGS. 44-48.

Figure 80:
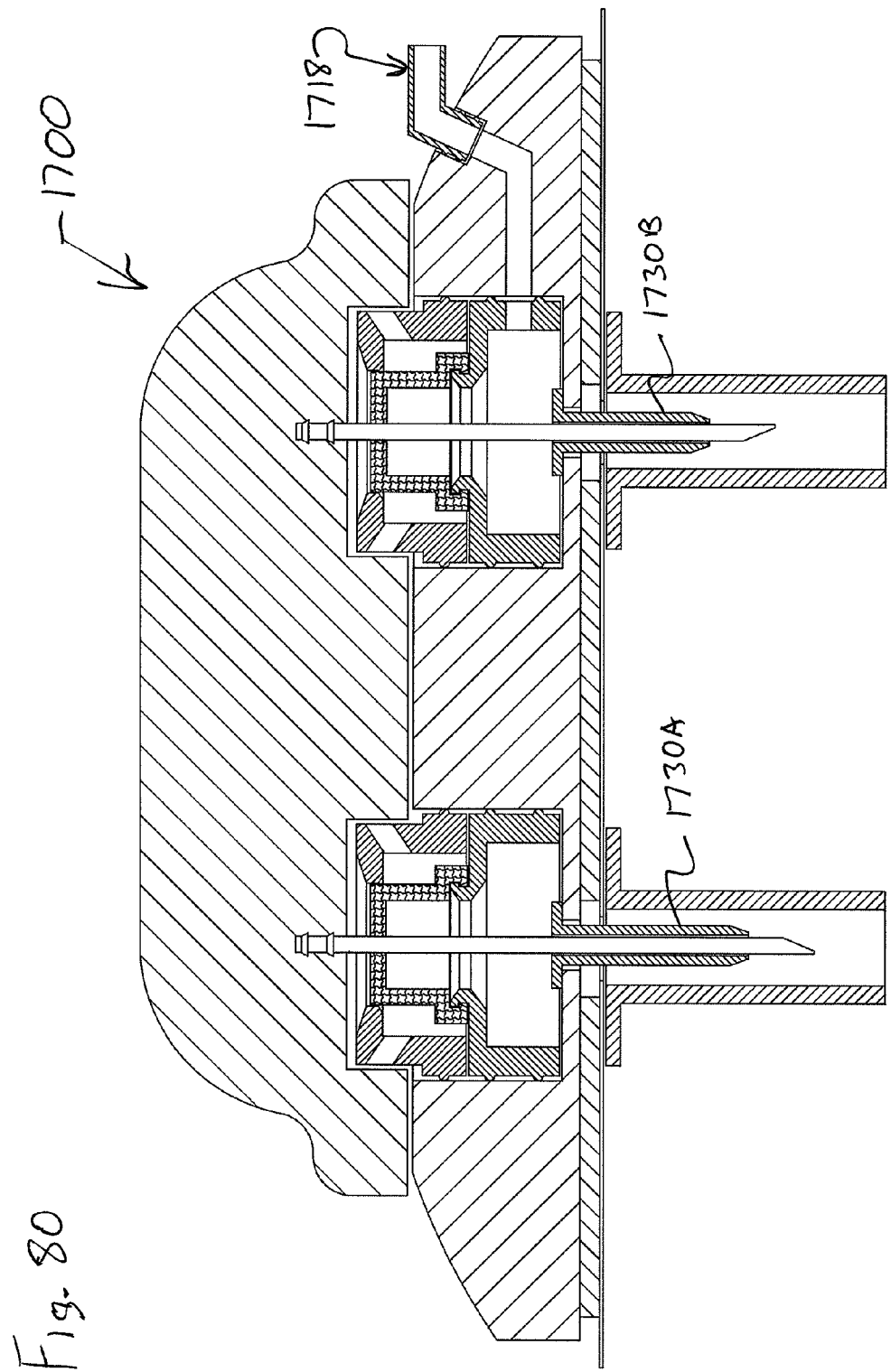
FIG. 80 shows a cross-section view of another non-limiting embodiment of the device. This embodiment is similar to that of FIG. 14 except that it utilizes two injection modules each having a cannula which has a different length.

FIG. 80 shows a cross-section view of another non-limiting embodiment of the device 1700. This embodiment is similar to that of FIG. 14 except that it utilizes two cannulas 1730A and 1730B (i.e., as part of two injection modules) which have different lengths. The injection module which includes cannula 1730B can be dedicated for use as a port which allows equipment, attachable via one or more nipples 1718, to monitor, e.g., in a continuous manner blood glucose levels, while the injection module having cannula 1730A is used for injecting substances into the user's tissue as in the embodiment of FIG. 1. Of course, the cannulas 1730A and 1730B can also be of the same length and/or have different diameters. One or both of the cannulas 1730A/1730B can also be of the rigid type. Preferably, the cannulas 1730A and 1730B are spaced apart by a distance which offers advantages specific to the desired spacing. By way of non-limiting example, the spacing can be between ¼ inch and 1 inch. Of course, the invention contemplates using a depth adjustment system of the type disclosed above and/or a spring insertion system of the type disclosed above on the instant embodiment.

The present fluid delivery systems may include on or more of the present fluid delivery devices that are sterilized (e.g., with ethylene oxide or gamma radiation) and sealed in a package, which may take the form of a pouch, tray, box (such as a box containing multiple trays), tube, or the like. The package may include instructions for use on the outside of the package or on material (e.g., a folded piece of paper) placed in the package. In some embodiments of systems that include a package containing multiple trays for resale, one set of instructions for use may be placed in the package. The systems also may include a vial or vials of fluid to be delivered to the user (such as insulin).

The materials from which the elements of the present fluid delivery devices may be made should be biocompatible. The septa cap or member that may be used with some embodiments of the present fluid delivery devices may be characterized as self-sealing septa, or resealing septa, and may be made from a resilient material. One example of a suitable material for such septa is silicone elastomer, which may be described as an elastomeric material, although other materials may be used. If the injection structure chosen to inject fluid into a given embodiment of the present fluid delivery devices is an injection needle, the injection needle used should be sized such that the septum will reseal when the needle is withdrawn. For example, the needle size should be chosen in light of the septum material and the radial pressure the needle will exert on the septum material it contacts such that the needle does not leave a septum opening when withdrawn that is large enough for fluid to leak upstream through it.

The bodies of the present fluid delivery devices may be made from many different materials, such as any suitable medical grade plastic and/or glass. The insertion hubs (or gripping portion) of the present fluid delivery devices that include them also may be made, for example, from any suitable medical grade plastic. The insertion structures (e.g., insertion needle) of the present fluid delivery devices that include them may be made from any suitable material, such as stainless steel or a suitably rigid polymer. The needle guide (e.g., member 1140 shown in the embodiment of FIG. 56 but usable on any of the herein disclosed embodiments) of the present fluid delivery devices that include them may be made from any suitable material, such as stainless steel, although other materials may be used. The soft cannulas (e.g., cannulas used on embodiments utilizing insertion needles) of the present fluid delivery devices that include them may be made from many different materials, such as any suitable medical grade plastic. The upper and lower support, as well as the septum support used on various embodiments, may be made from many different materials, such as any suitable medical grade plastic. Those that are not made from metal may be characterized as non-rigid cannulas or non-metal cannulas.

The needle guards NG, which can be used on all of the herein disclosed fluid delivery devices, may be made from many different materials, such as any suitable medical grade plastic. The adhesive layers or pads, which can be used on all of the herein disclosed fluid delivery devices, may be made from any suitable material, and any adhesive that is used may include an anti-bacterial and/or healing promotion substance (such as dexamethasone, or the like) that reduces the risk of infection and speeds the healing process once the fluid delivery device is removed from the user. The rigid cannulas, which are preferably used on devices which do not utilize an insertion needle, may be made from any suitable material—such as stainless steel, any suitable alloy or any suitably rigid polymer. Versions of the present rigid cannulas that are made from metal may (in such embodiments) be characterized as metal cannulas.

If a medical grade plastic or glass is used for one of the elements discussed above, such as, e.g., the body, the material chosen may, be translucent, transparent, semi-transparent, or opaque in different embodiments.

Embodiments of the present fluid delivery devices that use a soft cannula may be inserted using any well-known and appropriately configured insertion device, such as the insertion devices disclosed herein. Inserting one of the present fluid delivery devices into a user using only such an insertion device may be characterized as non-spring driven insertion, or insertion using force applied directly by hand. Other devices can be triggered by releasing the potential force built up in a compressed spring. Insertion using a spring-driven device may be characterized as spring-driven insertion. Still other insertion devices could be computer-controlled. Other forces that may be used to insert one of the present fluid delivery device into a user include pneumatic and hydraulic forces. In general, insertion of the embodiments of the present insertion devices that include non-rigid cannulas without any reinforcing coating should be relatively quick and forceful to reduce the chance of the cannula crimping or bending during insertion. The insertion of embodiments that include a rigid cannula or a non-rigid cannula that has been reinforced in some manner may be achieved more slowly and, in some cases, with less force.

As an alternative to the use of insertion devices with needles for inserting embodiments of the present fluid delivery devices that have a non-rigid cannula, an outer surface of the exposed portion of the cannula may be coated with a fluid soluble coating that provides a sharp tip, or point, at the end of the cannula, but that dissolves in the bodily fluids of the user after insertion. Such a coating is described in U.S. Patent Application Pub. No. 2002/0072720, the entire disclosure of which is hereby expressly incorporated by reference.

Different injection devices may be used to facilitate the delivery of fluid to, for example, the subcutaneous tissue of a user. For example, a standard syringe and syringe needle may be used. The syringe needle may be sharp and open at its end, sharp and open somewhere along its shaft other than at its end, blunt and open at its end, or blunt and open somewhere along its shaft other than at its end. Other suitable injection devices include pen-like devices having some sort of needle that is generally concealed. Injection of fluid into a patient using one of these injection devices may be characterized as delivering fluid to a user from a non-pump source, or delivering fluid to a user from a source that is not connected to a pump. In other embodiments of the present devices, systems and methods, a pump may be used in the fluid delivery process. For example, this is true of the fluid delivery devices that include an inlet fitting such as inlet fitting 218. Such fittings can also be utilized on any other of the herein disclosed embodiments.

While the target tissue of a patient may be pinched and/or pulled outwardly from the body slightly to isolate it, insertion of one of the present fluid delivery devices into the tissue of a user still may, in some embodiments, be characterized as being at a substantially perpendicular angle to a target skin location of a user/living being because the rigid cannula or non-rigid cannula and insertion structure will enter the user's tissue at an angle that is substantially perpendicular to the plane in which the target tissue lies.

As another example, in some embodiments of the present fluid delivery systems, the package containing one or more of the present fluid delivery devices also may include one or more capsules, or vials, or injection devices containing a prescribed amount of fluid. The package also may include a pump and associated tubing for coupling to a fitting such an inlet fitting.

The claims are not to be interpreted as including means-plus- or step-plus-function limitations, unless such a limitation is explicitly recited in a given claim using the phrase(s) "means for" or "step for," respectively.

What is claimed is:

1. A fluid delivery device comprising:
   a body;
   at least one cannula adapted to extend into subcutaneous tissue;
   a septum member adapted to allow a needle to puncture the septum member and to reseal the puncture once the needle is withdrawn from the puncture;
   the septum member comprising at least one of:
      a member having a puncturable section, a puncturable sidewall section, and an internal space that is in fluid communication with the cannula;
      a cap-shaped member comprising an internal space that is in fluid communication with the cannula;
      a cap-shaped member defining an internal space that can receive therein a tip portion of a needle when injected from plural different directions;
      a member having at least two non-parallel walls that can each be punctured by a needle and defining an internal space that can receive therein a tip portion of a needle when injected from plural different directions; and
      a member having a generally planar wall and a generally cylindrical wall which can each be punctured by a needle and defining an internal space that can receive therein a tip portion of a needle when injected from plural different directions; and
   another internal space that is each of:
      different from the internal space of the septum member;
      arranged between an upper end of the cannula and the internal space of the septum member; and
      in fluid communication with the internal space of the septum member.

2. The device of claim 1, wherein the body comprises an adhesive layer structured and arranged to at least temporarily secure the device to a user's skin.

3. The device of claim 1, further comprising a removable needle insertion mechanism having a portion which extends through the cannula and another portion which can be gripped by a user.

4. The device of claim 1, further comprising a support member comprising a first opening arranged over a one portion of the septum member and at least one second opening arranged over a different portion of the septum member.

5. The device of claim 4, wherein at least one of:
   the first opening comprises an axial opening and the at least one second opening comprises a generally circumferential opening or slot;

the first opening comprises an axial opening and the at least one second opening comprises a opening whose center axis is oriented at an angle between an axis of the first opening and a radial plane perpendicular to the axis of the first opening; and the first opening comprises an axial opening and the at least one second opening comprises at least two equally angularly spaced openings.

6. The device of claim 1, wherein the cannula comprises a center axis that is oriented at an angle between a vertical center axis of the body and a radial plane perpendicular to the vertical center axis of the body.

7. The device of claim 1, wherein the cannula is oriented at an angle that is not perpendicular to a bottom surface of the body.

8. The device of claim 1, further comprising a needle insertion mechanism configured to cause movement of the cannula from a first position to a second position.

9. The device of claim 1, wherein the cannula is movable from an initial retracted position to a puncturing position.

10. The device of claim 1, wherein the cannula is movable from an initial retracted position within the body to an extended position wherein a puncturing portion of the cannula is arranged outside the body.

11. The device of claim 1, further comprising a removable safety device structured and arranged to prevent movement of the cannula from a first position to a second position.

12. The device of claim 1, further comprising a manually activated needle insertion mechanism configured to cause movement of the cannula from a first position to a second position.

13. The device of claim 1, further comprising a trigger activated needle insertion mechanism configured to cause movement of the cannula from a first position to a second position.

14. The device of claim 1, further comprising a needle insertion mechanism configured to automatically cause movement of the cannula from a first position to a second position.

15. The device of claim 1, further comprising at least one of
a needle insertion mechanism comprising a biasing mechanism for causing movement of the cannula from a first position to a second position; and
an arrangement for adjusting a cannula penetrating depth.

16. The device of claim 1, wherein the device is adapted to function with a removable needle insertion mechanism and a tool comprising a biasing mechanism for causing movement of the cannula from a first position to a second position.

17. The device of claim 1, wherein the device is adapted to function with a removable needle insertion mechanism and a trigger activated tool comprising a biasing mechanism and a movable member for causing movement of the cannula from a first position to a second position.

18. The device of claim 1, further comprising at least one of:
a system for causing movement of the cannula from a first position to a second position; and
a system for causing movement of the cannula from an extended position to a retracted position.

19. The device of claim 1, wherein the device is a single-use device.

20. The device of claim 1, further comprising a removable cannula insertion mechanism adapted to move the cannula to a puncturing position.

21. The device of claim 1, further comprising at least one of:
an adjustable septum support member adapted to move the septum between at least two angular positions; and
a swivel mounted septum support member adapted to move the septum between at least two angular positions.

22. A fluid delivery device comprising:
a body;
at least one cannula adapted to extend into subcutaneous tissue;
an insertion mechanism adapted to be gripped by a user and adapted to facilitate insertion of the cannula into the subcutaneous tissue;
a septum member adapted to allow a needle to puncture the septum member and to reseal the puncture once the needle is withdrawn from the puncture;
the septum member comprising at least one of:
a one-piece member having a puncturable wall, a puncturable sidewall, and an internal space that is in fluid communication with the cannula;
a cap-shaped member defining an internal space that is in fluid communication with the cannula;
a member having at least two non-parallel walls that can each be punctured by a needle and defining an internal space that is in fluid communication with the cannula; and
a member having a generally planar wall and a generally cylindrical wall which can each be punctured by a needle, and defining an internal space that is in fluid communication with the cannula; and
another internal space that is each of:
different from the internal space of the septum member;
arranged between an upper end of the cannula and the internal space of the septum member; and
in fluid communication with the internal space of the septum member.

23. A fluid delivery device comprising:
a body;
at least one cannula adapted to extend into subcutaneous tissue;
an insertion mechanism adapted to be gripped by a user and comprising a needle portion adapted to facilitate insertion of the cannula into the subcutaneous tissue;
a one-piece septum member adapted to allow a needle to puncture the septum member and to reseal the puncture once the needle is withdrawn from the puncture;
the septum member comprising at least one of:
a member having a puncturable main wall, a puncturable sidewall, and an internal space that is in fluid communication with the cannula;
a cap-shaped member comprising a main puncturable and resealable section, a side puncturable and resealable section, and an internal needle receiving space;
a member having at least two non-parallel walls that can each be punctured by a needle and an internal needle receiving space; and
a member having a generally planar wall, a generally cylindrical wall which can each be punctured by a needle, and an internal needle receiving space; and
another internal space that is each of:
different from the internal space of the septum member;
arranged between an upper end of the cannula and the internal space of the septum member; and
in fluid communication with the internal space of the septum member.

24. A method of making the fluid delivery device of claim 1, the method comprising:
mounting a cannula and a septum to a body.

25. A method of using the fluid delivery device of claim 1, the method comprising:
attaching the device to a user's skin; and
inserting a portion of the cannula into the subcutaneous tissue.

26. A fluid delivery device comprising:
a body;
at least one cannula adapted to extend into subcutaneous tissue;
the at least one cannula being movable relative to the body from an initial retracted position to a puncturing position;
a cap-shaped septum member adapted to allow a needle to puncture the septum member from at least two different directions and to reseal each puncture once the needle is withdrawn from each puncture, and
said at least one cannula
having an upper end spaced from an inner surface of an upper end of the septum member when in the puncturing position,
wherein the upper end of the septum member is arranged over the upper end of the cannula after the cannula is moved to the puncturing position.

27. The device of claim 26, wherein the cap-shaped septum member comprises at least one of:
a member having a first section and a side wall section that can each be punctured by a needle and defining an internal space;
a member having a main wall and a side wall that can each be punctured by a needle and defining an internal space;
a member having at least two non-parallel walls that can each be punctured by a needle and defining an internal space; and
a member having a generally planar wall and a generally cylindrical wall which can each be punctured by a needle and defining an internal space.

28. The device of claim 26, wherein the cap-shaped septum member comprises:
a first puncturable and resealable section that can be punctured by a needle arranged parallel to an axis of the cannula and that can inject a substance which can pass through the cannula; and
a second section that can be punctured by a needle that is not arranged parallel to an axis of the cannula and that can inject a substance which can pass through the cannula.

29. The device of claim 26, wherein the cap-shaped septum member comprises:
a first section that is puncturable and resealable and that can be punctured along a direction parallel to an axis of the cannula; and
a second section that can be punctured along a different direction that is not arranged parallel to an axis of the cannula,
wherein the first section and the second section define an internal space which can receive a substance injected through the main section and the other section.

30. The device of claim 29, further comprising a support member comprising:
a main opening allowing insertion of a needle along a direction parallel to an axis of the cannula; and
another opening allowing insertion of a needle along a different direction that is not arranged parallel to an axis of the cannula.

31. The device of claim 26, further comprising a support member covering the septum member and comprising:
a main opening allowing insertion of a needle along a main direction; and
at least one other opening allowing insertion of a needle along a direction different from the main direction.

32. The device of claim 31, wherein the cap-shaped septum member is a one-piece member that comprises:
a main section that can be punctured along a direction parallel to an axis of the cannula; and
another section that can be punctured along a different direction that is not arranged parallel to an axis of the cannula.

33. A fluid delivery device comprising:
a body;
at least one cannula adapted to extend into subcutaneous tissue;
the at least one cannula being movable relative to the body from an initial retracted position to a puncturing position;
a septum member adapted to allow a needle to puncture the septum member from at least two different directions and to reseal each puncture once the needle is withdrawn from each puncture;
said at least one cannula being at least one of:
movable relative to the septum when the septum is coupled to the body; and
movable away from the septum when moved from the initial retracted position to the puncturing position; and
a support member comprising:
a first opening allowing insertion of a needle along a direction parallel to an axis of the cannula and configured to allow puncturing of the septum; and
at least one second opening allowing insertion of a needle along a different direction that is not arranged parallel to an axis of the cannula and configured to allow puncturing of the septum,
wherein, in the retracted position, an upper end of the cannula is arranged between an upper end of the septum member and a skin attaching surface of the body.

* * * * *